US012325866B2

(12) United States Patent
Nahmias

(10) Patent No.: US 12,325,866 B2
(45) Date of Patent: Jun. 10, 2025

(54) SYSTEMS AND METHODS FOR GROWING CELLS IN VITRO

(71) Applicant: Yissum Research Development Company of the Hebrew University of Jerusalem Ltd., Jerusalem (IL)

(72) Inventor: Yaakov Nahmias, Mevaseret Zion (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 1172 days.

(21) Appl. No.: 16/316,667

(22) PCT Filed: Jul. 11, 2017

(86) PCT No.: PCT/IL2017/050790
§ 371 (c)(1),
(2) Date: Jan. 10, 2019

(87) PCT Pub. No.: WO2018/011805
PCT Pub. Date: Jan. 18, 2018

(65) Prior Publication Data

US 2020/0080050 A1 Mar. 12, 2020

Related U.S. Application Data

(60) Provisional application No. 62/360,495, filed on Jul. 11, 2016.

(51) Int. Cl.
*C12N 5/00* (2006.01)
*C12M 1/00* (2006.01)

(52) U.S. Cl.
CPC ........... *C12N 5/0062* (2013.01); *C12M 21/00* (2013.01); *C12M 29/04* (2013.01); *C12M 29/10* (2013.01); *C12N 2506/1307* (2013.01)

(58) Field of Classification Search
CPC ......... C12N 5/0062; C12N 2506/1307; C12M 21/00; C12M 29/04; C12M 29/10; C12M 29/18; A01N 1/00
See application file for complete search history.

(56) References Cited

U.S. PATENT DOCUMENTS 3,418,208 A * 12/1968 Coty ........................ C12N 1/30 435/244
3,721,569 A 3/1973 Steinkraus
(Continued)

FOREIGN PATENT DOCUMENTS

CN 104096232 10/2014
JP 2001-039740 2/2001
(Continued)

OTHER PUBLICATIONS

Office Action dated Dec. 2, 2020 From the Israel Patent Office Re. Application No. 264193 and Its Translation Into English. (7 Pages).
(Continued)

*Primary Examiner* — Michael L Hobbs
(74) *Attorney, Agent, or Firm* — Stephen Wellard; Polsinelli PC

(57) ABSTRACT

A system for growing cells comprising a bioreactor chamber for growing the cells, a delivery system delivering a perfusion solution to the bioreactor chamber for perfusion of the perfusion solution through the cells, a dialysis system having a dialyzer, a dialysate for performing a dialysis and a filter for reducing ammonia content in said dialysate, and a controller that circulates the perfusion solution through the dialyzer and the dialysate through the filter.

29 Claims, 14 Drawing Sheets
(11 of 14 Drawing Sheet(s) Filed in Color)
Specification includes a Sequence Listing.

(56) References Cited

U.S. PATENT DOCUMENTS

| | | | | |
|---|---|---|---|---|
| 3,791,932 | A | 2/1974 | Schuurs et al. | |
| 3,839,153 | A | 10/1974 | Schuurs et al. | |
| 3,850,578 | A | 11/1974 | McConnell | |
| 3,850,752 | A | 11/1974 | Schuurs et al. | |
| 3,853,987 | A | 12/1974 | Dreyer | |
| 3,867,517 | A | 2/1975 | Ling | |
| 3,879,262 | A | 4/1975 | Schuurs et al. | |
| 3,901,654 | A | 8/1975 | Gross | |
| 3,935,074 | A | 1/1976 | Rubenstein et al. | |
| 3,984,533 | A | 10/1976 | Uzgiris | |
| 3,996,345 | A | 12/1976 | Ullman et al. | |
| 4,034,074 | A | 7/1977 | Miles | |
| 4,098,876 | A | 7/1978 | Piasio et al. | |
| 4,666,828 | A | 5/1987 | Gusella | |
| 4,683,202 | A | 7/1987 | Mullis | |
| 4,801,531 | A | 1/1989 | Frossard | |
| 4,879,219 | A | 11/1989 | Wands et al. | |
| 5,011,771 | A | 4/1991 | Bellet et al. | |
| 5,192,659 | A | 3/1993 | Simons | |
| 5,272,057 | A | 12/1993 | Smulson et al. | |
| 5,281,521 | A | 1/1994 | Trojanowski et al. | |
| 5,464,764 | A | 11/1995 | Capecchi et al. | |
| 5,487,992 | A | 1/1996 | Capecchi et al. | |
| 5,906,743 | A | 5/1999 | Cohen et al. | |
| 6,265,024 | B1 | 7/2001 | England | |
| 6,398,039 | B1 | 6/2002 | Xue et al. | |
| 6,835,390 | B1 | 12/2004 | Vein | |
| 7,270,829 | B2 | 9/2007 | Van Eelen | |
| 8,703,216 | B2 | 4/2014 | Forgacs et al. | |
| 8,802,361 | B2 | 8/2014 | Lee et al. | |
| 9,302,038 | B2 | 5/2016 | Stange | |
| 2003/0054544 | A1 | 3/2003 | Gruenberg | |
| 2006/0019385 | A1* | 1/2006 | Smith | C12M 41/32 435/348 |
| 2010/0197007 | A1 | 8/2010 | Cailleret et al. | |
| 2011/0091604 | A1 | 4/2011 | Miller | |
| 2011/0301249 | A1 | 12/2011 | Challakere | |
| 2012/0093994 | A1 | 4/2012 | Hsieh et al. | |
| 2013/0323708 | A1* | 12/2013 | Yarmush | C12N 5/067 435/1.2 |
| 2015/0289541 | A1 | 10/2015 | Brown et al. | |
| 2015/0305390 | A1 | 10/2015 | Vrljie et al. | |
| 2016/0339377 | A1 | 11/2016 | Arakawa et al. | |
| 2020/0080050 | A1 | 3/2020 | Nahmias | |

FOREIGN PATENT DOCUMENTS

| | | |
|---|---|---|
| JP | 2018-166466 | 11/2018 |
| WO | WO 00/46354 | 8/2000 |
| WO | WO 2011/002926 | 1/2011 |
| WO | WO 2014/078579 | 5/2014 |
| WO | WO 2015/066377 | 5/2015 |
| WO | WO 2015/118148 | 8/2015 |
| WO | WO 2018/011805 | 1/2018 |
| WO | WO 2018/011805 A9 | 1/2018 |

OTHER PUBLICATIONS

Translation Dated Dec. 11, 2020 of Notification of Office Action dated Nov. 23, 2020 From the State Intellectual Property Office of the People's Republic of China Re. Application No. 201780055183.9. (10 Pages).

Come et al., "Improvement of Culture Conditions of Human Embryoid Bodies Using a Controlled Perfused and Dialyzed Bioreactor System," Tissue Engineering: Part C, vol. 14, No. 4, 2008.

Liu et al., "Oleate induces transdifferentiation of chicken fibroblasts into adipocyte-like cells," *Comparative Biochemistry and Physiology*, Part A, 154 (2009) 135-141.

Green et al., "An Established Pre-Adipose Cell Line and its Differentiation in Culture," *Cell*, vol. 3, 127-133, Oct. 1974.

Yin et al., "In vitro myogenic and adipogenic differentiation model of genetically engineered bovine embryonic fibroblast cell lines," *Biotechnol Lett* (2010) 32:195-202.

Edelman et al., "In Vitro-Cultured Meat Production," *Tissue Engineering*, vol. 11, No. 5/6, 2005, 659-662.

May, "In vitro meat: protein for twelve billion?" University of Otago, Dec. 2012, 141 pages.

Encyclopedia Britannica, "Adipose Cell", accessed Apr. 27, 2022, 3 pages.

Kokta et al., "Regulation of lipid accumulation in 3T3-L1 cells: insulin-independent and combined effects of fatty acids and insulin," *Animal*, 2008, 2:1, pp. 92-99.

ATCC (3T3-L1, pp. 1-7; 2022).

Communication Relating to the Results of the Partial International Search and Provisional Opinion dated Oct. 20, 2017 From the International Searching Authority Re. Application No. PCT/IL2017/050790. (17 Pages).

Corrected International Search Report and the Written Opinion dated Mar. 22, 2018 From the International Searching Authority Re. Application No. PCT/IL2017/050790. (18 Pages).

International Preliminary Report on Patentability dated Jan. 24, 2019 From the International Bureau of WIPO Re. Application No. PCT/IL2017/050790. (12 Pages).

International Search Report and the Written Opinion dated Jan. 15, 2018 From the International Searching Authority Re. Application No. PCT/IL2017/050790. (18 Pages).

Ezra et al. "Microprocessor-Based Integration of Microfluidic Control for the Implementation of Automated Sensor Monitoring and Multithreaded Optimization Algorithms", Biomedical Microdevices, XP035527019, 17(4): 1-9, Published Online Jul. 31, 2015. p. 82, col. 2, Para 2, Figs.1-3.

Hallenborg et al. "PPAR[Gamma] Ligand Production Is Tightly Linked to Clonal Expansion During Initiation of Adipocyte Differentiation", Journal of Lipid Research, XP002776649, 55(12): 2491-1500, Published Online Oct. 13, 2014.

Lee et al. "Puerarin Enhances Adipocyte Differentiation, Adiponectin Expression, and Antioxidant Response in 3T3-L1 Cells", Biofactors, XP002776650, 36(6): 459-467, Published Online Aug. 30, 2010.

Shulman et al. "Long-Term Culture and Coculture of Primary Rat and Human Hepatocytes", Methods in Molecular Biology, XP055412339, 945: 287-302, 2013.

Levy et al., "Long-term culture and expansion of primary human hepatocytes," 2015, *Nature Biotechnology*, pp. 1264-1271.

Skelley et al., "An active bubble trap and debubbler for microfluidic systems," *Lab Chip*, 2008, 8, pp. 1733-1737.

Bhavli et al., Real-time monitoring of metabolic function in liver-on-chip microdevices tracks the dynamics of mitochondrial dysfunction, *PNAS*, Apr. 4, 2016, pp. E2231-E2240.

Intarapat et al., "Chick stem cells: current progress and future prospects," *Stem Cell Research*, 2013, 11, pp. 1378-1392.

Lu et al., "Avian-induced pluripotent stem cells derived using human reprogramming factors," *Stem Cells and Development*, vol. 21, No. 3, 2012, pp. 394-403.

Rossello et al., "Mammalian genes induce partially reprogrammed pluripotent stem cells in non-mammalian vertebrate and invertebrate species," *eLi*fe, 2013;2:e00036, 24 pages.

Hou et al., "Pluripotent stem cells induced from mouse somatic cells by small-molecule compounds," *Science*, Jul. 18, 2013, 9 pages.

Shan et al., "Identification of small molecules for human hepatocyte expansion and iPS differentiation," *Nat Chem Biol.*, Aug. 2013, 9(8): 514-520.

Cao et al., "Conversion of human fibroblasts into functional cardiomyocytes by small molecules," *Science*, Apr. 28, 2016, 11 pages.

Fu et al., "Direct reprogramming of mouse fibroblasts into cardiomyocytes with chemical cocktails," *Cell Research*, 2015, 25:1013-1024.

Nahmias et al., "Endothelium-mediated hepatocyte recruitment in the establishment of liver-like tissue in vitro," *Tissue Engineering*, vol. 12, No. 6, 2006, pp. 1627-1638.

Tolboom et al., "Recovery of warm ischemic rat liver grafts by normothermic extracorporeal perfusion," *Transplantation*, Jan. 27, 2009; 87(2): 170-177.

(56) References Cited

OTHER PUBLICATIONS

Prill et al., "Real-time monitoring of oxygen uptake in hepatic bioreactor shows CYP450-independent mitochondrial toxicity of acetaminophen and amiodarone," *Arch Toxicol*, Jun. 14, 2015, 11 pages.
Mujaj et al., "Serum-free primary human fibroblast and keratinocyte coculture," *Tissue Engineering: Part A*, vol. 16, No. 4, 2010, pp. 1407-1420.
Mitchell et al., "Insulin-like growth factor I stimulates myoblast expansion and myofiber development in the limb," *Developmental Dynamics*, 2002, 223:12-23.
Sakanyan et al. "Screening and discovery of nitro-benzoxadiazole compounds activating epidermal growth factor receptor (EGFR) in cancer cells," *Scientific Reports*, Feb. 5, 2014, 4:3977, 11 pages.
Chal et al., "Differentiation of pluripotent stem cells to muscle fiber to model Duchenne muscular dystrophy," *Nature Biotechnology*, 2015, 33(9), pp. 962-969.
Choi et al., "MyoD converts primary dermal fibroblasts, chondroblasts, smooth muscle, and retinal pigmented epithelial cells into striated mononucleated myoblasts and multinucleated myotubes," *Proc. Natl. Acad. Sci. USA*, Oct. 1990, vol. 87, pp. 7988-7992.
Watanabe et al., "Tet-on inducible system combined with in ovo electroporation dissects multiple roles of genes in somitogenesis of chicken embryos," *Developmental Biology* 305 (2007) pp. 625-636.
Niwa et al., "Efficient selection for high-expression transfectants with a novel eukaryotic vector," *Gene*, 108 (1991) 193-200.
Xu et al., "A zebrafish embryo culture system defines factors that promote vertebrate myogenesis across species," *Cell* 155, Nov. 7, 2013, pp. 909-921.
Zheng et al., "Skeletal myogenesis by human embryonic stem cells," *Cell Research* (2006): 713-722.
Pain et al., "Long-term in vitro culture and characterization of avian embryonic stem cells with multiple morphogenetic potentialities," *Development* 122, 2339-2348 (1996).
Lee et al., "Identification of Small Molecules Which Induce Skeletal Muscle Differentiation in Embryonic Stem Cells via Activation of the Wnt and Inhibition of Smad2/3 and Sonic Hedgehog Pathways," *Stem Cells* 2016;34:299-310.
Bentzinger et al., "Building muscle: molecular regulation of myogenesis," *Cold Spring Narb Perspect Biol* 2012;4:a008342, 17 pages.
Moussaieff et al., "Glycolysis-mediated changes in acetyl-CoA and histone acetylation control the early differentiation of embryonic stem cells," *Cell Metabolism* 21, 391-402, Mar. 3, 2015.
Nahmias et al., "Micropatterning of living cells by laser-guided direct writing: application to fabrication of hepatic-endothelial sinusoid-like structures," *Nature Protocols*, vol. 1, No. 5, 2006, pp. 2288-2296.
Nahmias et al., "Integration of technologies for hepatic tissue engineering," *Adv Biochem Eng/Biotechnol* (2006) 103: 309-329.
Takebe et al., "Vascularized and functional human liver from an iPSC-derived organ bud transplant," *Nature*, Jul. 25, 2015, vol. 499, pp. 481-484.
Nahmias et al., "A novel formulation of oxygen-carrying matrix enhances liver-specific function of cultured hepatocytes," *The FASEB Journal*, 2006, pp. 2531-2533.
Bitter et al., "Expression and Secretion Vectors for Yeast," *Methods in Enzymology*, 1987, vol. 153, pp. 516-544.
Studier et al., "Use of T7 RNA Polymerase to Direct Expression of Cloned Genes," *Methods in Enzymology*, 1990, vol. 185, pp. 60-89.
Brisson et al., "Expression of a bacterial gene in plants by using a viral vector," *Nature*, Aug. 1984, vol. 310, pp. 211-514.
Takamatsu et al., "Expression of bacterial chloramphenicol acetyltransferase gene in tobacco plants mediated by TMV-RNA," *The EMBO Journal*, 1987, vol. 6, No. 2, pp. 307-311.
Coruzzi et al., "Tissue-specific and light-regulated expression of a pea nuclear gene encoding the small subunit of ribulose-1,5-bisphosphate carboxylase," *The EMBO Journal*, 1984, vol. 3, No. 8, pp. 1671-1679.
Broglie et al., Light-Regulated Expression of a Pea Ribulose-1,5-Bisphosphate Carboxylase Small Subunit Gene in Transformed Plant Cells, *Science*, 1984, vol. 224, pp. 838-843.
Gurley et al., "Upstream Sequences Required for Efficient Expression of a Soybean Heat Shock Gene," *Molecular and Cellular Biology*, Feb. 1986, vol. 6, No. 2, pp. 559-565.
Zabala et al., "Optimization of the Tet-on System to Regulate Interleukin 12 Expression in the Liver for the Treatment of Hepatic Tumors," *Cancer Research* 64, Apr. 15, 2004, pp. 2799-2804.
Liang et al., "High efficiency gene transfer into mammalian kidney cells using baculovirus vectors," *Arch Virol* (2004) 149: 51-60.
Tonkinson et al., "Antisense Oligodeoxynucleotides as Clinical Therapeutic Agents," *Cancer Investigation*, 1996, 14(1), 54-65.
Booth et al., "The use of a 'universal' yeast expression vector to produce an antigenic protein of *Mycobacterium leprae,*" *Immunology Letters*, 1998, 19, pp. 65-70.
Gardella et al., "Expression of Human Parathyroid Hormone-(1-84) in *Eschericia coli* as a Factor X-cleavable Fusion Protein," *The Journal of Biological Chemistry*, vol. 265, No. 26, Sep. 15, 1990, pp. 15851-15859.
Nayve Jr. et al., "Selective removal of ammonia from animal cell culture broth," *Cytotechnology* 6: 121-130, 1991.
Nachman et al., "Roxarsone, inorganic arsenic, and other arsenic species in chicken: a U.S.-based market basket sample," Environmental Health Perspectives, Jul. 2013, vol. 121, No. 7, 818-824.
Waters et al., "Multidrug-Resistant *Staphylococcus aureus* in US Meat and Poultry," Clinical Infectious Diseases, 2011:52 pp. 1227-1230.
Easy Biology Class, "Animal Fats vs Plant Fats," www.easybiologyclass.com, pp. 1-3.
Notification of Office Action dated Nov. 23, 2020 From the State Intellectual Property Office of the People's Republic of China Re. Application No. 201780055183.9. (9 Pages).
Cao et al., "Differentiation of embryonic stem cells into hepatocytes that coexpress coagulation factors VIII and IX," Acta Pharmacologica Sinica (2010) 31: 1478-1486.
Nayve, Jr. et al., "HBs-MAB production in perfusion culture with selective ammonia removal system," Journal of Biotechnology 34 (1994), 217-225.
Nayve, Jr. et al., "Effects of ammonium ion removal on growth and MAb production of hybridoma cells," Cytotechnology (1995) vol. 18, pp. 35-50.
Portner et al., "Dialysis Cultures," Appl Microbiol Biotechnol (1998) 50, 403-414.
Tolboom et al., "A model for Normothermic Preservation of the Rat Liver," Tissue Engineering, vol. 13, Nov. 8, 2007, 2143-2151.
Frahm et al., "Improvement of a mammalian cell culture process by adaptive, model-based dialysis fed-batch cultivation and suppression of apoptosis," Bioprocess Bisyst Eng (2003) 26: 1-10.
Agar, "Review: Understanding sorbent dialysis systems," Nephrology 15 (2010) 406-411.
Kim et al., "Control of struvite precipitation by selective removal of NH(4)+ with dialyzer/zeolite in an anaerobic membrane bioreactor," Appl Microbiol Biotechnol (2007) 75: 187-193.
Small et al., "Chemistry in the Kitchen: Making Ground Meat More Helpful," NEJM 1991, vol. 324, No. 2, pp. 73-77.
Merriam Webster Dictionary—Definition of Extruded, https://www.merriam-webster.com/dictionary/extruded?utm_campaign=sd&utm_medium=serp&utm_source=jsonld, accessed Jul. 5, 2023.
J Aubert et al., "Determination of the differentially expressed genes in microarray experiments using local FDR", BMC Bioinformatics (2004), 5:125.
John P. Didion et al., "SNP array profiling of mouse cell lines identifies their strains of origin and reveals cross contamination and widespread aneuploidy", Didion et al. BMC Genomics 2014, 15:847.
Pranjal Mehar, "A web based platform to create Human Cell Atlas", https://www.techexplorist.com/web-based-platform-create-human-cell-atlas/13698/ (2018), accessed Jan. 30, 2024.
Verena Passerini et al., "The presence of extra chromosomes leads to genomic instability", Nature Communications, pp. 1-12, 2016.
Wikipedia, "Adipocyte," retrieved from https://en.wikipedia.org/w/index.php?0 title=Adipocyte&oldid=1190135332, downloaded Jun. 20, 2024. 5.

(56) References Cited

OTHER PUBLICATIONS

Colleluori, G. et al., "Mammary gland adipocytes in lactation cycle, obesity and breast cancer", Reviews in Endocrine and Metabolic Disorders, Mar. 22, 2021, pp. 22:241-255. 2.

Giordano, A. et al. "Mechanisms in endocrinology: white, brown and pink adipocytes: the extraordinary plasticicity of the adipose organ," European journal of Endocrinology, vol. 170, Issue 5, May 1, 2014, pp. R159-R171.

Pastika, L. et al., "Spontaneous immortalization of chicken fibroblasts generates stable, high-yield cell lines for serum-free production of cultured meat," Nature Food, vol. 4, Dec. 22, 2022, plus Supplementary Data, pp. 35-50. 1.

Ye, R. Z. et al., "Fat Cell Size: Measurement Methods, Pathophysiological Origins, and Relationship With Metabolic Dysregulations", Endocrine Reviews, vol. 43, Issue 1, Feb. 2022, pp. 35-60.

* cited by examiner

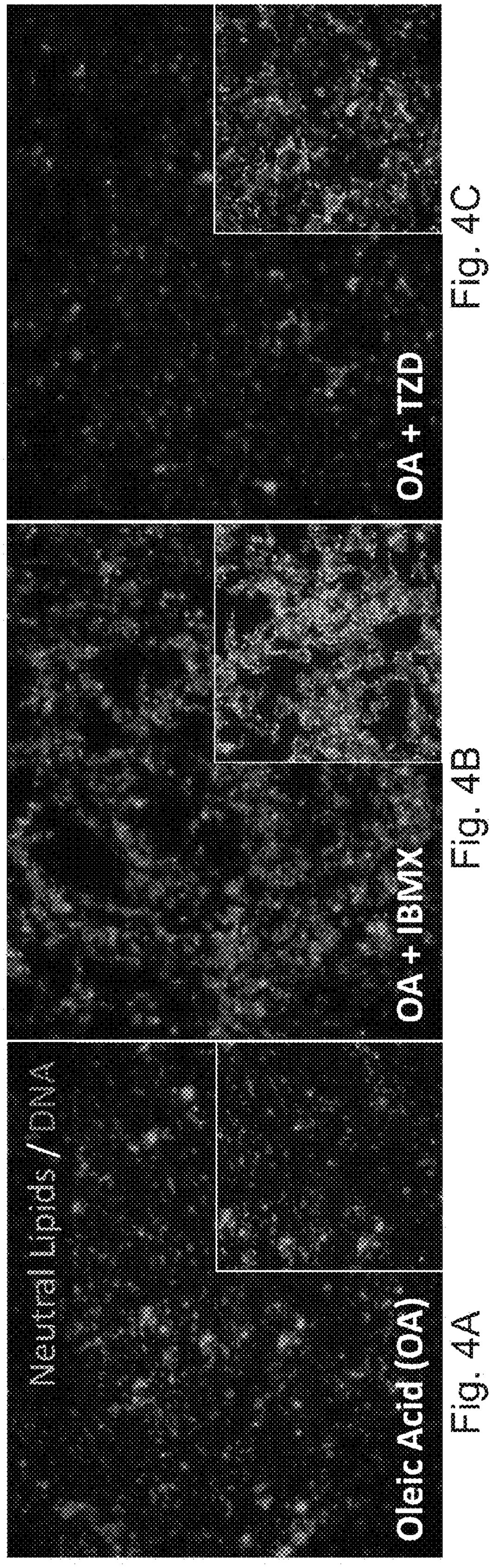
Fig. 4A
Fig. 4B
Fig. 4C
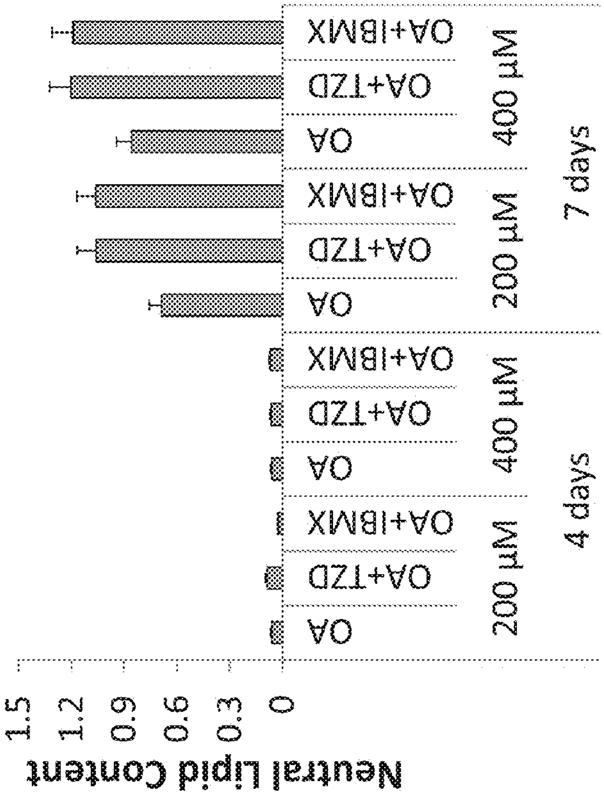
Fig. 4D

SYSTEMS AND METHODS FOR GROWING CELLS IN VITRO

RELATED APPLICATIONS

This application is a National Phase of PCT Patent Application No. PCT/IL2017/050790 having International filing date of Jul. 11, 2017, which claims the benefit of priority under 35 USC § 119(e) of U.S. Provisional Patent Application No. 62/360,495 filed on Jul. 11, 2016. The contents of the above applications are all incorporated by reference as if fully set forth herein in their entirety.

SEQUENCE LISTING STATEMENT

The ASCII file, entitled 76441_ST25.txt, created on Jan. 10, 2019 comprising 29,718,555 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to cell growth and, more particularly, but not exclusively, to a system and a method for growing cells in vitro.

The current world population is over 7 billion and still rapidly growing. In order to support the nutritional requirement of this growing population, increasing amount of land is dedicated for food production. The natural sources are insufficient to fulfill the demand. This has led to famine in some parts of the world. In other parts of the world the problem is being addressed by large-scale production of animals in dense factory farms under harsh conditions. This large-scale production is not only causing great suffering to animals, but in addition, organoarsenic compounds and antibiotics are used to increase food efficiency and control infection, increasing arsenic levels and drug-resistance bacteria in meat products. It can also increase the number of diseases and the consequences thereof for both animals and humans. Large scale slaughtering is currently required to fulfill the current food requirements and as a consequence of large-scale disease outbreaks such as the occurrence of porcine pestivirus and mad cows disease. These diseases also result in loss of the meat for human consumption thus completely denying the purpose for which the animals were being bred in the first place. In addition the large-scale production is reducing the flavor of the finished product. A preference exists among those that can afford it for non-battery laid eggs and non-battery produced meat. Not only it is a matter of taste but also a healthier choice thereby avoiding consumption of various feed additives such as growth hormones. Another problem associated with mass animal production is the environmental problem caused by the vast amounts of fecal mater the animals produce and which the environment subsequently has to deal with. Also the large amount of land currently required for animal production or the production of feed for the animals which cannot be used for alternative purposes such as growth of other crop, housing, recreation, wild nature and forests.

Several approaches have been disclosed to address these problems.

U.S. Pat. No. 685,390 discloses a non-human tissue engineered meat product and a method for producing same. The meat product comprises muscle cells that are grown ex-vivo and is used for food consumption. The muscle cells may be grown and attached to a support structure and may be derived from any non-human cells. The meat product may also comprise other cells such as fat cells or cartilage cells, or both, that are grown ex-vivo together with the muscle cells.

U.S. Pat. No. 7,270,829 discloses a meat product containing in-vitro produced animal cells in a three dimensional form and a method for producing the meat product. The method comprises the culturing in-vitro of animal cells in medium free of hazardous substances for humans on an industrial scale thereby providing three dimensional animal tissue suited for human consumption, wherein the cells are muscle cells, somite cells or stem cells.

U.S. Pat. No. 8,703,216 discloses methods and engineered meat products formed as a plurality of at least partially fused layers, wherein each layer comprises at least partially fused multicellular bodies comprising non-human myocytes and wherein the engineered meat is comestible, and wherein the non-human myocytes are adhered and/or cohered to one another; and the multicellular bodies are arranged adjacently on a nutrient-permeable support substrate and maintained in culture to allow the multicellular bodies to at least partially fuse to form a substantially planar layer for use in formation of engineered meat.

U.S. Patent application US2011/0091604 discloses examples of methods, systems and computer accessible mediums related to producing synthetic meat, with a substrate configured to support cell growth, which can be seeded with cells. The seeded substrate may be rolled through a bioreactor having a roll-to-roll mechanism, thereby allowing nutrients and growth factors to interact with the cells. The seeded substrate may be stretched to simulate muscle action. The seeded substrate may be monitored for uniformity of cell growth as it is rolled through the bioreactor. A film of synthetic meat is obtained from the substrate.

U.S. Patent application US2011/0301249 discloses methods for producing in-vitro cultured protein products that are enhanced with stem cells, providing nutrients to an animal by feeding the animal with the in-vitro cultured protein products.

WO 2015/066377 discloses methods for enhancing cultured meat production, such as livestock-autonomous meat production, wherein the meat can be any metazoan tissue or cell-derived comestible product intended for use as a comestible food or nutritional component by humans, companion animals, domesticated or captive animals whose carcasses are intended for comestible use, service animals, conserved animal species, animals used for experimental purposes, or cell cultures.

U.S. Pat. No. 8,802,361 discloses a perfusion solution comprising specific metabolic agents, antioxidant agents, and membrane stabilizer agents that can help improve preservation, organ viability, and in some cases recover organs that would otherwise being unusable for transplantation, wherein the perfusion solution can be used in combination with hypothermic machine perfusion. It has been found that combination of the perfusion solution and hypothermic machine perfusion can help prevent or reduce further damage to the organ and restore the organ's antioxidant system, stabilize the cellular cytoskeleton and cellular membranes, inhibit arachidonic acid pathway, provide oncotic support, reduce interstitial edema formation, and help restore energy stores within the organ.

One of the main problems of the aforementioned techniques is the relation between cost, time and quality of the product, with a long time to produce, at extremely high costs with a mediocre quality that cannot and will not replace the current meat derived from livestock.

SUMMARY OF THE INVENTION

According to an aspect of some embodiments of the present invention there is provided a system for growing cells, the system comprising:

- a bioreactor chamber for growing the cells;
- a delivery system configured to deliver a perfusion solution to the bioreactor chamber for perfusion of the perfusion solution through the cells at a perfusion rate;
- a dialysis system having a dialyzer and a dialysate for performing a dialysis and a filter for reducing ammonia content in the dialysate; and
- a controller configured to circulate the perfusion solution out of the bioreactor chamber through the dialyzer and back into the bioreactor chamber, and to circulate the dialysate out of the dialyzer through the filter and back into the dialyzer.

According to an aspect of some embodiments of the present invention there is provided a method of growing cells, the method comprising:

- growing the cells in a bioreactor chamber;
- delivering a perfusion solution to the bioreactor chamber for perfusion of the perfusion solution through the cells;
- circulating the perfusion solution out of the bioreactor chamber through a dialyzer having a dialyzer therein and back into the bioreactor chamber; and
- circulating the dialysate out of the dialyzer, through a filter selected for reducing ammonia content in the dialysate, and back into the dialyzer.

According to an aspect of some embodiments of the present invention there is provided a system for growing cells, the system comprising:

- a bioreactor chamber for growing the cells;
- a delivery system configured to deliver a perfusion solution to the bioreactor chamber for perfusion of the perfusion solution through the cells at a perfusion rate;
- a dialysis system having a dialyzer for performing a dialysis; and
- a controller configured to increase the perfusion rate with time, and to circulate the perfusion solution out of the bioreactor chamber, separately through the dialyzer and the delivery system, and back into the bioreactor chamber;
- wherein at least 90% of a volume of the perfusion solution that exits the bioreactor chamber is circulated back into the bioreactor chamber during an entire growth period of the cells.

According to an aspect of some embodiments of the present invention there is provided a method of growing cells, the method comprising:

- growing the cells in a bioreactor chamber;
- delivering by a delivery system a perfusion solution to the bioreactor chamber for perfusion of the perfusion solution through the cells at a perfusion rate that increases with time; and
- circulating the perfusion solution out of the bioreactor chamber separately through a dialyzer and the delivery system, and back into the bioreactor chamber;
- wherein at least 90% of a volume of the perfusion solution that exits the bioreactor chamber is circulated back into the bioreactor chamber during an entire growth period of the cells.

According to an aspect of some embodiments of the present invention there is provided a system for growing a suspension cell culture, the system comprising:

- a bioreactor chamber for growing the suspension cell culture;
- a delivery system configured to deliver a perfusion solution to the bioreactor chamber for perfusion of the perfusion solution through the suspension cell culture at a perfusion rate;
- a dialysis system having a dialyzer for performing a dialysis; and
- a controller configured to circulate the perfusion solution out of the bioreactor chamber through the dialyzer and back into the bioreactor chamber, while maintaining at least 95% of cells forming the suspension cell culture in the bioreactor chamber during the circulation.

According to an aspect of some embodiments of the present invention there is provided a method of growing a suspension cell culture, the method comprising:

- growing the suspension cell culture in a bioreactor chamber;
- delivering a perfusion solution to the bioreactor chamber for perfusion of the perfusion solution through the suspension cell culture; and
- circulating the perfusion solution out of the bioreactor chamber through a dialyzer and back into the bioreactor chamber, while maintaining at least 95% of cells forming the suspension cell culture in the bioreactor chamber during the circulation.

According to an aspect of some embodiments of the present invention there is provided an adipocyte obtainable according to the methods of some embodiments of the invention.

According to an aspect of some embodiments of the present invention there is provided a method of generating a cultured fat on a protein matrix, comprising generating the adipocyte cell from the fibroblast according to the method of some embodiments of the invention, wherein the culturing is performed on a plant-derived protein matrix, thereby generating the cultured fat on the protein matrix.

According to an aspect of some embodiments of the present invention there is provided an in-vitro method of generating an adipocyte cell from a fibroblast, comprising culturing a spontaneously immortalized fibroblast in a serum-free medium comprising oleic acid and a PPAR-gamma agonist or activator, thereby generating the adipocyte cell.

According to an aspect of some embodiments of the present invention there is provided a cultured fat in a plant-derived protein matrix.

According to an aspect of some embodiments of the present invention there is provided an in-vitro method of generating a myocyte from a fibroblast, comprising upregulating expression within a spontaneously immortalized fibroblast of a polypeptide selected from the group consisting of myoD1 and myogenin.

According to an aspect of some embodiments of the present invention there is provided a myocyte obtainable according to the methods described herein.

According to an aspect of some embodiments of the present invention there is provided an in-vitro method of screening for a small molecule capable of producing a myocyte, comprising:

(a) transfecting a spontaneously immortalized fibroblast with a nucleic acid construct comprising a nucleic acid sequence encoding a reporter polypeptide under a transcriptional control of a promoter specifically active in myocytes,
(b) contacting a transfected fibroblast resultant of step (a) with at least one small molecule of a plurality of small molecules, and
(c) detecting activity of the reporter polypeptide above a pre-determined threshold in the transfected fibroblast following step (b), wherein presence of the activity above the pre-determined threshold is indicative that the at least one small molecule is capable of converting the spontaneously immortalized fibroblast into the myocyte.

According to an aspect of some embodiments of the present invention there is provided an in-vitro method of generating an edible meat, comprising culturing:
(a) a spontaneously immortalized fibroblast in a serum-free medium under conditions suitable for converting the fibroblast into an adipocyte, and/or
(b) a spontaneously immortalized fibroblast in a serum-free medium under conditions suitable for converting the fibroblast into a myocyte, thereby generating the edible meat.

According to an aspect of some embodiments of the present invention there is provided an in-vitro method of generating an edible meat, comprising culturing:
(a) a spontaneously immortalized fibroblast in a serum-free medium under conditions suitable for converting the fibroblast into an adipocyte, and/or
(b) a spontaneously immortalized fibroblast in a serum-free medium under conditions suitable for converting the fibroblast into a myocyte,
(c) an endothelial cell, thereby generating the edible meat.

According to an aspect of some embodiments of the present invention there is provided an edible meat obtainable from the methods described herein.

According to an aspect of some embodiments of the present invention there is provided a method of generating a spontaneously immortalized fibroblast, comprising:
(a) culturing avian embryo cells in the presence of a serum-containing medium under adherent culture conditions to thereby obtain chicken embryonic fibroblasts,
(b) passaging the avian embryonic fibroblasts for at least 10-12 passages in the serum-containing medium under the adherent conditions until culture collapse, wherein the culture collapse is characterized by senescence and/or death of at least 90% of the avian embryonic fibroblasts,
(c) isolating at least one colony which survived the culture collapse in the serum-containing medium for at least additional 20 passages, thereby generating the spontaneously immortalized fibroblast.

According to an aspect of some embodiments of the present invention there is provided a spontaneously immortalized chicken fibroblast obtainable by the method of some embodiments of the invention.

According to some embodiments of the invention, at least 90% of a volume of the perfusion solution that exits the bioreactor chamber is circulated back into the bioreactor chamber during an entire growth period of the cells According to some embodiments of the invention, the cells form a tissue.

According to some embodiments of the invention, the cells form a cultured meat product.

According to some embodiments of the invention, the dialyzer comprises a filter selected to reduce ammonia content of the perfusion solution.

According to some embodiments of the invention, the perfusion rate increases over time.

According to some embodiments of the invention, the increment is exponential.

According to some embodiments of the invention, there is a plurality of bioreactor chambers, all being in fluid communication with the same dialyzer, and wherein the dialyzer applies the dialysis to perfusion solutions circulated out of each of the bioreactor chambers.

According to some embodiments of the invention, the dialyzer is configured to ensure that at least one protein exiting the bioreactor chamber with the perfusion solution is circulated back into the bioreactor chamber.

According to some embodiments of the invention, the at least one protein is albumin.

According to some embodiments of the invention, there is from about 0.1 liters to about 10 liters of the perfusion solution per one kilogram of cells in the bioreactor chamber.

According to some embodiments of the invention, there is from about 0.1 liters to about one liter of the perfusion solution per one kilogram of cells in the bioreactor chamber.

According to some embodiments of the invention, the delivery of the perfusion solution is via a fluidic circuit constituted to enrich the perfusion solution by a culture medium and oxygen.

According to some embodiments of the invention, the fluidic circuit is constituted to enrich the perfusion solution also by carbon dioxide.

According to some embodiments of the invention, the fluidic circuit is constituted to trap or remove bubbles present in the perfusion solution.

According to some embodiments of the invention, the fluidic circuit is constituted to heat the perfusion solution.

According to some embodiments of the invention, the delivery and the circulation is without discarding the perfusion solution throughout the cell growth.

According to some embodiments of the invention, the cells form a cultured meat product and wherein the bioreactor chamber is at most 5 liters in volume.

According to some embodiments of the invention, the bioreactor chamber is at most 5 liters in volume.

According to some embodiments of the invention, the fibroblast is an avian fibroblast.

According to some embodiments of the invention, the avian is selected from the group consisting of: chicken, duck, goose, and quail.

According to some embodiments of the invention, the fibroblast is a chicken embryonic fibroblast.

According to some embodiments of the invention, the spontaneously immortalized fibroblast is non-genetically modified.

According to some embodiments of the invention, the PPAR-gamma agonist or activator is a small molecule.

According to some embodiments of the invention, the small molecule is selected from the group consisting of Thiazolidinedione, 3-Isobutyl-1-methylxanthine (IBMX), phenamil, GW7845, RG14620, and Harmine.

According to some embodiments of the invention, the small molecule is rosiglitazone.

According to some embodiments of the invention, the serum-free medium is devoid of animal contaminants.

According to some embodiments of the invention, the serum-free medium is devoid of human contaminants.

According to some embodiments of the invention, the serum-free medium comprises insulin or a substitute thereof, and basic fibroblast growth factor (bFGF) or a substitute thereof, and at least one additional agent selected from the group consisting of dexamethasone, transferrin, selenium, EGF or a substitute thereof, and PGE2.

According to some embodiments of the invention, the substitute of the insulin comprises IGF-1 or a stabilized Long R3 IGF-1

According to some embodiments of the invention, the substitute of the EGF comprises an EGF-R agonist.

According to some embodiments of the invention, the EGF-R agonist comprises NSC-228155 at a concentration of 5-50 ng/ml.

According to some embodiments of the invention, the substitute of the bFGF is a small molecule or a synthetic agonist of the FGF-signaling pathway.

According to some embodiments of the invention, the synthetic agonist is C19-jun at a concentration of 10-20 ng/ml.

According to some embodiments of the invention, the dexamethasone is provided at a concentration range of 0.01 nM-10 μM.

According to some embodiments of the invention, the bFGF is provided at a concentration range of 0.1-30 ng/ml.

According to some embodiments of the invention, the EGF is provided at a concentration range of 0.1-30 ng/ml.

According to some embodiments of the invention, the PGE2 is provided at a concentration range of 0.01 nM-10 μM.

According to some embodiments of the invention, the plant-derived protein matrix is from the legume (Fabaceae) family, from the cereal family or from the pseudocereal family.

According to some embodiments of the invention, the plant-derived protein matrix comprises a soy protein or a pea protein.

According to some embodiments of the invention, the cultured fat of some embodiments of the invention is obtainable by the method of some embodiments of the invention.

According to some embodiments of the invention, the upregulation is of the myoD1 and myogenin polypeptides.

According to some embodiments of the invention, the chicken myoD1 polypeptide is encoded by a polynucleotide comprising the nucleic acid sequence set forth by SEQ ID NO:5.

According to some embodiments of the invention, the chicken myogenin polypeptide is encoded by a polynucleotide comprising the nucleic acid sequence set forth by SEQ ID NO:7.

According to some embodiments of the invention, the chicken myoD1 polypeptide is encoded by the nucleic acid construct set forth by SEQ ID NO: 1 or 3.

According to some embodiments of the invention, the chicken myogenin polypeptide is encoded by the nucleic acid construct set forth by SEQ ID NO: 2.

According to some embodiments of the invention, the serum-free medium comprises oleic acid and a PPAR-gamma agonist.

According to some embodiments of the invention, the endothelial cell is a spontaneously immortalized endothelial cell.

According to some embodiments of the invention, the endothelial cell is non-genetically modified.

According to some embodiments of the invention, step (a) and step (b) are effected simultaneously in the same culture system.

According to some embodiments of the invention, step (a) and step (b) are effected in two distinct culture systems.

According to some embodiments of the invention, steps (a), (b) and (c) are effected simultaneously in the same culture system.

According to some embodiments of the invention, the culturing is performed on a scaffold.

According to some embodiments of the invention, the culturing is performed in a perfusion system.

According to some embodiments of the invention, the culturing is performed on an edible hollow fiber cartridge.

According to some embodiments of the invention, the culturing is performed on a vegetable-derived matrix.

According to some embodiments of the invention, the vegetable-derived matrix is from a cereal family, legume (Fabaceae) family or a pseudocereal family.

According to some embodiments of the invention, the legume is soy or pea.

According to some embodiments of the invention, the culturing is performed in a suspension culture devoid of substrate adherence.

According to some embodiments of the invention, the culturing is performed in the system of some embodiments of the invention.

According to some embodiments of the invention, the edible meat of some embodiments of the invention is in a form of a patty or nugget with a density of about $200 \times 10^6$ cells/gram.

According to some embodiments of the invention, the serum-containing medium is a DMEM/F12 based medium.

According to some embodiments of the invention, the serum in the medium comprises about 15% fetal bovine serum (FBS).

According to some embodiments of the invention, the chicken embryo is obtained from a fertilized broiler chicken egg grown for 10-12 days.

According to some embodiments of the invention, the spontaneously immortalized chicken fibroblast of some embodiments of the invention being capable of a continuous passaging for at least 30 passages.

According to some embodiments of the invention, the spontaneously immortalized chicken fibroblast of some embodiments of the invention being capable of at least 90 population doublings.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 2A—Broiler chicken embryo extracted from fertilized egg on day 11. FIG. 2B—morphology of primary chicken embryonic fibroblasts (CEF) after 1 population doubling ("PD 1"). FIG. 2C—Morphology of spontaneously immortalized chicken fibroblasts (CSIF) post crisis (after 90 population doublings ("PD 90"). FIG. 2D—Growth kinetics of CSIF cultured in 15% serum (FBS, black curve), serum-free medium as described in Example 5 of the Examples section which follows ("SFM", red curve) and commercially available TheraPEAK™ (LONZA WALKERSVILLE, INC. Walkersville, MD, 217930127) medium ("T-PEAK", green curve). FIG. 2E—Doubling time of CSIF cultured in 15% serum (FBS, black column), serum-free medium as described in Example 6 of the Examples section which follows ("SFM", red column) and commercially available TheraPEAK™ (LONZA WALKERSVILLE, INC. Walkersville, MD, 217930127) medium ("T-PEAK", green column). Note that the immortalized chicken fibroblast cell line (CSIF) exhibit the same growth kinetics and doubling time in the presence of serum-free medium formulation uncovered by the present inventor (as described in Example 6 of the Examples section which follows) when compared to the serum-containing medium. Also note that the commercially available TheraPEAK™ (LONZA WALKERSVILLE, INC. Walkersville, MD, 217930127) failed to support the expansion of the CSIF cells (FIG. 2D), and the cells cultured therein exhibit an elongated doubling time of 40 hours as compared to less than 20 hours in either the serum-containing medium of the SFM of some embodiments of the invention.

FIGS. 4A-D depict conversion of CSIF to adipocytes in serum-free medium. FIGS. 4A-C. LipidTOX™ (Thermo Fisher Scientific) neutral lipid stain of serum-free cultures of CSIF exposed to either 400 μM oleic acid (OA) alone (FIG. 4A) or with 0.5 mM IBMX (OA+IBMX, FIG. 4B), or 10 μM Rosiglitazone (OA+TZD, FIG. 4C) for 7 days. Both small molecules show strong adipogenesis in the presence of OA. FIG. 4D—Normalized intracellular lipid content (in arbitrary fluorescent units) of CSIF cultures treated for 4 and 7 days as prescribed above. 400 μM OA with small molecules IBMX or TZD show optimal results.

FIG. 5A—Phase image of CSIF expressing Dox-inducible MyoD1 and Myogenin (MYOG) for 6 days ("d6"). FIGS. 5B-C—CSIF expressing rat myosin light chain COP-GFP reporter (rMLC3-GFP) following Dox-induced MyoD1+MYOG expression for 11 days (FIG. 5B) or 30 days (FIG. 5C). About 2-4% of the cultures become positive for MLC3 (Green). MLC3 positive myoblasts maintain elongated fiber morphology for over 30 days in vitro (FIG. 5C). FIG. 5D—Fluorescence staining using phalloidin (F-Actin probe, green) showing multinucleated cells (syncytia) as well as some striation following 7 days in culture. Nuclei are stained with Hoechst (blue). FIG. 5E—Immunofluorescence staining for α1-skeletal muscle actin (ACTA1, green) and Troponin T (red) showing a clear muscle phenotype by day 7 of induction. Nuclei are stained with Hoechst (blue).

FIG. 11A—Sulforhodamine B stain of 3D collagen scaffolds loaded with $150\times10^6$ spontaneously immortalized chicken fibroblasts (CSIF) and $15\times10^6$ spontaneously immortalized rat microvascular endothelial cells (RCEC) per millimeter of volume. FIG. 11B—Phase image of 3D scaffolds loaded with high density of CSIF and RCEC co-culture following 11 days of perfusion in a bioreactor. FIG. 11C—Confocal cross-section of 3D scaffolds loaded with RCEC (red label) and iPS-derived cells (green) showing vascular network formation and close cell-cell interactions following 11 days of perfusion in a bioreactor.

DESCRIPTION OF SPECIFIC EMBODIMENTS OF THE INVENTION

Figure 1A:
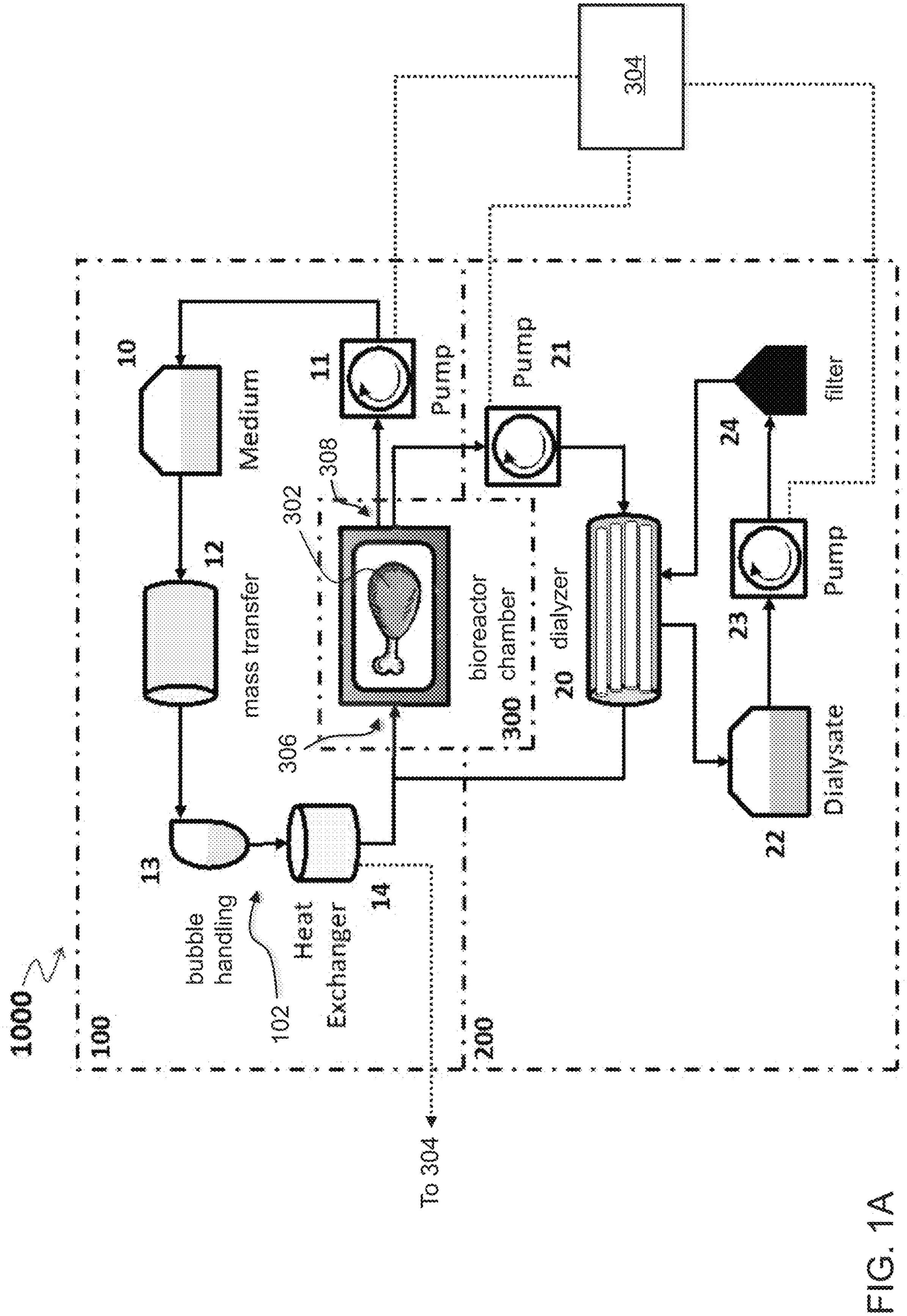
FIGS. 1A and 1B are schematic illustrations of a system suitable for growing cells according to some embodiments of the present invention.

The present invention, in some embodiments thereof, relates to cell growth and, more particularly, but not exclusively, to a system and a method for growing cells in vitro.

The present inventor has described a system for culturing cells which can be used, in some embodiments of the present invention, for generating edible meat.

Chicken meat has been a major source of dietary protein since the dawn of the agricultural revolution. Production has traditionally been local, with families and later small villages growing their own grain-fed animals. However, rapid urbanization and population growth driven by the industrial revolution led to the development of intensive farming methods. Factory farms now produce close to 9 billion chickens each year in the United States, with animal growth and transportation producing 18% of current greenhouse emissions. It was recognized by the present inventor that large amount of chicken meat (e.g., over 70% in the United States) contains unsafe levels of arsenic, and antibiotic resistant bacteria. It was also recognized by the present inventor that transportation and animal density lead to widespread fecal contamination of chicken meat leading to increased *salmonella* infection.

Laboratory-grown meat allows growing meat from animal cells under sterile conditions. It was find by the present inventor that it is possible to produce a sufficient amount of cells per unit mass of meat product (e.g., from about 500 to about $200\times10^6$ cells per gram), without the use of animal products, such as fetal bovine serum. However, while many cell culture techniques have been developed over the past 50 years for biological research, the present inventor found that such culture techniques are incredibly wasteful, requiring a large volume of culture medium to produce a small mass of laboratory-grown meat. For example, known techniques require a volume of about 230 liter of to produce about 1 Kg of meat, translating to a cost of at least $4,600 per Kg due to medium costs alone.

For purposes of better understanding some embodiments of the present invention, the construction and operation of industrial scale cell manufacturing techniques will be described.

Known in the art are several industrial scale cell manufacturing techniques. These include a 10,000 liter fed-batch process, and a 1,000 liter concentrated perfusion process. Typical media cost at current prices is estimated at about $20 per liter L for fed-batch processes and about $5 per liter for concentrated perfusion processes. For ideal CHO cells, the fed-batch processes allow achieving cell densities of about $25\times10^6$ cells/ml, and the concentrated perfusion processes allow achieving cell densities of about $100\times10^6$ cells/ml. These cell densities mean that a 10,000 liter fed batch reactor can produce 1,250 kg mass every 19 days, while a 1,000 liter perfusion reactor can produce 500 kg mass every 30 days. The fed batch process consumes 12,500 liter medium including the seed train, while the perfusion process consumes 2,120 liters medium. These numbers translate to $200 per kg mass for fed batch process and $21 per kg mass for perfusion process for the culture medium costs alone.

It is recognized that consumable costs are often less than a third of the cost of good. One parameter is the capital costs. 10,000 liter fed batch facilities are known to cost of $50 million or more, and 1,000 perfusion facilities are known to cost $30 million or more. Assuming a liberal 10% annual depreciation and maintenance costs, an industrial scale 10,000 fed batch facility can produce 24,000 kg per year at an annual maintenance cost of about $5,000,000, resulting in a capital cost of $200 per kg mass produced. An industrial scale 1,000 perfusion facility can produce 6,000 kg per year at an annual maintenance cost of about $3,000,000, resulting in a capital cost of about $500 per kg mass produced.

The present inventor devised a cell growing technique that outperforms these conventional processes.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
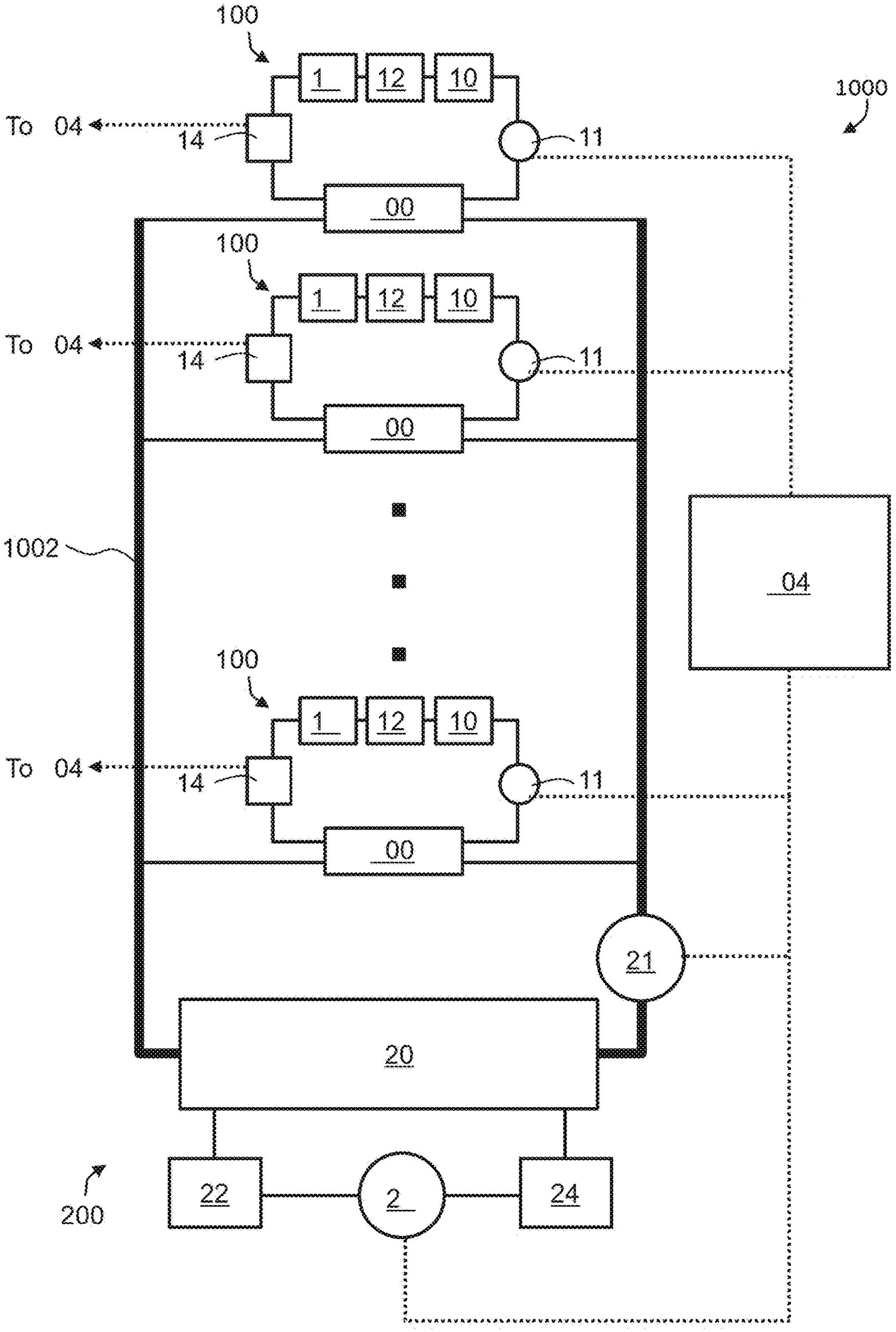

FIGS. 1A and 1B are schematic illustrations of a system 1000 suitable for growing cells 302 according to some embodiments of the present invention. System 1000 can be used form growing many types of cells. In some embodiments of the present invention cells 302 form a suspension culture, useful, for example, for cellular therapy or for protein or vaccine production, in some embodiments of the present invention cells 302 form a tissue, useful, for example, for tissue transplantation, and in some embodiments of the present invention cells form a cultured meat.

System 1000 preferably comprises a bioreactor chamber 300 for growing the cells 302 therein, a delivery system 100 configured to deliver a perfusion solution to bioreactor chamber 300 for perfusion of the perfusion solution through the cells, and a dialysis system 200 having a dialyzer 20 and a dialysate 22 for performing a dialysis to exchange nutrient and byproduct. Bioreactor chamber 300 can employ any technique for growing cells, including, without limitation, a hollow fiber cartridge, a packed bed, or a vascularized embedded tissue configuration. The perfusion of the perfusion solution through the cells is optionally and preferably continuous. In some embodiments of the present invention, at the end of the growth cycle there are from about 0.1 liters to about 10 liters, e.g., 1 liter, of perfusion solution per one kilogram of cells in the bioreactor chamber. Bioreactor chamber 300 can have any size but in preferred embodiments of the present invention bioreactor chamber 300 is at most 5 liters, e.g., from about 1 liter to about 5 liters, in volume. These embodiments are particularly useful when system 1000 comprises a plurality of bioreactor chambers as further detailed hereinbelow. Bioreactor chamber 300 can typically facilitate growth of muscle tissue, from an initial amount of about 20 mg to a consumable amount of at least 500 grams, e.g., 1000 grams or more.

System 1000 preferably operates in a generally closed loop fluidic mode, wherein the perfusion solution exits bioreactor chamber 300 through one or more outlet ports 308 into delivery system 100 and dialysis system 200, treated in these systems and then returns back into bioreactor chamber 300 through one or more inlet ports 306. The operation is referred to as "a close loop operation" in the sense that the perfusion solution itself is not discarded. Thus, system 1000 is optionally and preferably devoid of any mechanism for removing the perfusion solution out of system 1000 into an external waste removal device, and devoid of any mechanism that increases the amount of perfusion solution during the operation. It is to be understood, however, that the contents of the perfusion solution are changed during operation by interacting with systems 100 and 200. In various exemplary embodiments of the invention wherein at least 90% or at least 92% or at least 94% or at least 96% or at least 98% of a volume of the perfusion solution that exits bioreactor chamber 300 (either to system 100 or to system 200) is circulated back into bioreactor chamber 300 at all times over a period of at least 4 days or at least 5 days or at least 6 days or at least 7 days or at least 8 days or at least 9 days or at least 10 days or at least 12 days or at least 14 days or at least 16 days or at least 18 days or at least 20 days, or during the entire growth cycle of cells 302.

System 1000 optionally and preferably comprises a controller 304 for controlling delivery system 100, dialysis system 200 and/or bioreactor chamber 300. Controller 304 optionally and preferably comprises a circuit configured for performing the various operations described herein. In some embodiments of the present invention controller 304 is a computerized controller. Representative control lines from controller are shown as dotted lines. One of ordinary skills in the art, provided with the details described herein would know how to construct control lines between controller 304 and other controllable components of system 1000.

In some embodiments of the present invention controller 304 circulates the perfusion solution out of bioreactor chamber 300 through dialyzer 20 and back into bioreactor chamber 300. This can be achieved by means of a pump 21 which is controlled by controller 304. In various exemplary embodiments of the invention the circulation is executed while maintaining at least 95% or at least 96% or at least 97% of the cells 302 in bioreactor chamber 300 during the circulation. Preferably, dialyzer 20 is configured to ensure that at least one protein (e.g., albumin), more preferably all proteins, exiting bioreactor chamber 300 with the perfusion solution is circulated back into bioreactor chamber 300. This can be done for example, by providing a membrane dialyzer with a membrane that ensures that the respective protein (such as, but not limited to, albumin, with a molecular weight of about 66.5 kDa) is circulated back to bioreactor chamber 300 without entering the dialysate 22 of dialysis system 200. The advantage of this embodiment is that albumin is a carrier protein of growth factors, hormones, and fatty acids, and can therefore facilitate growth of cells 302 for at least a period that equals its characteristic half-life (about 20 days). This significantly reduces the production cost of the cells since albumin, hormones, and growth factors are the main cost driver of culture media.

In various exemplary embodiments of the invention a filter is employed in dialysis system 200 to remove ammonia from the portion of the perfusion solution that enters dialysis system 200. This can be achieved by providing dialysis system 200 with a filter 24 selected for reducing ammonia content in dialysate 22. In these embodiments, controller 304 optionally and preferably circulates dialysate 22 out of dialyzer 20 through filter 24 and back into dialyzer 22, for example, by controlling a pump 23 in dialysis system 200. Ammonia is a product of peptide degradation and glutamine breakdown. Ammonia become toxic and limits cell growth when it reaches 5 mM concentration. The close loop operation of the present embodiments preferably separates the protein-containing medium from the protein-free dialysate that can be scrubbed of ammonia without losing protein to non-specific absorption. Suitable for the present embodiments are filters such as, but not limited to, packed Zeolites particles or carbon meshes. Zeolite-based oxygen concentrator systems are widely used to produce medical-grade oxygen. The zeolite is used as a molecular sieve to create purified oxygen from air using its ability to trap impurities, in a process involving the adsorption of nitrogen, leaving highly purified oxygen and clearing ammonia from the solution.

System 1000 preferably operates in cycles, wherein the cell growth is initiated at the beginning of the cycle, and the grown cells are taken out of the chamber to provide a cellular product (suspension culture, tissue, cultured meat) at the end of the cycle. Typically, a 10 day cycle is employed but other cycle durations are also contemplated. In some embodiments of the present invention controller 304 ensures that the perfusion rate within bioreactor chamber 300 increases over time during the operation cycle. Preferably, the increment is exponential. The increment of the perfusion rate need not to be continuous, albeit a continuous increment of the perfusion rate is also contemplated. For example, the perfusion rate can be increased intermittently at certain days during the operation cycle. Typically, but not necessarily, the first increment is effected several days after the beginning of the cycle. At the end of the cycle, the perfusion rate is preferably at least 20 ml/s or at least 25 ml/s or at least 30 ml/s or at least 35 ml/s, e.g., 36 ml/s or more.

Referring again to FIGS. 1A-B the delivery of the perfusion solution is optionally and preferably via a fluidic circuit 102, which is optionally and preferably controlled by controller 304, for example, by means of a pump 11 in delivery system 100, and is constituted to enrich the perfusion solution by a culture medium and one or more gaseous media, such as, but not limited to, oxygen, carbon dioxide and nitrogen. This is optionally and preferably achieved by means of a culture medium reservoir 10 that enriches the perfusion solution by the culture medium, and a mass transfer device 12 such as, but not limited to, an oxygenator or the like, that enriches the perfusion solution by one or more gaseous media. Typically, mass transfer device 12 provides a mixture of Oxygen from about 21% to about 95%, Carbon dioxide from about 0% to about 10% and balanced to 100% by Nitrogen. Preferably, mass transfer device 12 maintains a generally constant (e.g., with 10% or less tolerance) pH. In a representative example, which is not to be considered as limiting, mass transfer device 12 provides a mixture of about 80% Oxygen about 5% Carbon dioxide and about 15% Nitrogen.

Optionally, fluidic circuit 102 is constituted to trap or remove bubbles present in the perfusion solution. This can be achieved by means of a bubble handling device 12 that may include a bubble trap and/or a debubbler. The advantage of trapping or removing the bubbles is that bubbles that inadvertently introduced into the bioreactor chamber 300 can negatively affect the operation of system 1000 since bubbles are cytotoxic to cells and can potentially rupture their cell membranes, and so trapping or removing the bubbles can improves the performance of system 1000. In some embodiments of the present invention fluidic circuit 102 is also constituted to heat the perfusion solution, optionally and preferably before the perfusion solution enters the bioreactor chamber 300.

System 1000 can comprise more than one bioreactor chamber 300. This preferred embodiment is illustrated in FIG. 1B. Shown are several bioreactor chambers, each being optionally and preferably similar to bioreactor chamber 300 as described herein, and several delivery systems, each being optionally and preferably similar to delivery system 100 as described herein, wherein each delivery system circulates, for example, by means of pump 11, the perfusion solution through one of the bioreactor chambers.

A portion of the perfusion solution also exits the bioreactor chambers for dialysis as further detailed hereinabove. In the illustrated embodiments, which is not to be considered as limiting, portions of the perfusion solutions from all the bioreactor chambers enter a main circulation channel 1002 circulating the perfusion solutions into the same dialysis system, which is optionally and preferably similar to dialysis system 200 as described herein. Thus, in these embodiments, System 1000 comprises a plurality of bioreactor chambers, a respective plurality of delivery systems, and a shared dialysis system which apply dialysis to perfusion solutions of all the bioreactor chambers.

The bioreactor chambers, delivery systems and dialysis system are optionally and preferably controlled by controller 304 as further detailed hereinabove.

The number of bioreactor chambers (and of respective delivery systems) in system 1000 is preferably selected such that the aggregate volumes of the perfusion solutions in the bioreactor chambers can be dialyzed by the dialysis system. Typically, there are from about 10 to about 500, e.g., about 100 bioreactor chambers in system 1000. For example, when the dialysis system is constructed to dialyze about V liters of perfusion solution, and each of the bioreactor chambers has about v liters of perfusion solution, the number of bioreactor chambers in system 1000 is V/v. As a representative example which is not to be considered as limiting, V can be about 500 and v can be about 5, so that V/v is about 100. The advantage of having a plurality of relatively small bioreactor chambers is that it allows having a relatively high perfusion rate.

Following is a more detailed description of system 1000, according to some embodiments of the present invention.

Dialyzer 20 can be, for example, hollow fiber dialyzer, such as, but not limited to, the hollow fiber dialyzer that is commercially distributed by Rancho Spectrum Labs (Rancho Dominguez, CA). The dialyzer can include membrane having an area of from about 500 to about 1000, e.g., about 790 $cm^2$, and a molecular weight cutoff of from about 20 to about 40, e.g., about 30 kDa. A fraction of the perfusion solution can be diverted using a pump 21, such as, but not limited to, a peristaltic pump, to system 200 through dialyzer 20. The dialyzer 20 dialyzes the perfusion solution by counter-flow exposure to a protein-free dialysate 22, recirculated through a filter 24, such as, but not limited to, an ammonia filter 24, an additional pump 23, such as, but not limited to, a peristaltic pump. Temperature within system 1000 is optionally and preferably maintained at a physiological range selected based on the type of animal cell 302 being grown. For chicken, for example, the temperature can be from about 38 to about 42° C., for beef cow the temperature can be from about 36.7 to about 39° C., for pig the temperature can be from about 38 to about 39° C., etc.

Bioreactor Chamber

In some embodiments of the present invention, the chamber 300 has a volume and internal dimensions that are configured and arranged to receive the growing cells and retain the cells within its volume while a sufficient amount of perfusion solution continuously circulates through the growing cells. The chamber 300 is optionally and preferably specifically adapted to the type of cells in it, in order to provide the adequate environment for the cells to grow and minimize mechanical damage or physical stress that can block vascular supply of oxygen and nutrients to the growing cells.

Peristaltic Pumps

Peristaltic pumps are known in the art. In order to provide any person skilled in the art with the required information to perform the present invention a brief explanation will be provided. A peristaltic pump is a type of positive displacement pump used for pumping a variety of fluids (www(dot)en(dot)wikipedia(dot)org/wiki/Peristaltic_pump, incorporated herein as reference). The fluid is contained within a flexible tube fitted inside a circular pump casing (though linear peristaltic pumps have been made). A rotor with a number of "rollers", "shoes", "wipers", or "lobes" attached to the external circumference of the rotor compresses the flexible tube. As the rotor turns, the part of the tube under compression is pinched closed (or "occludes") thus forcing the fluid to be pumped to move through the tube. Additionally, as the tube opens to its natural state after the passing of the cam ("restitution" or "resilience") fluid flow is induced to the pump. This process is called peristalsis and is used in many biological systems such as the gastrointestinal tract. Typically, there will be two or more rollers, or wipers, occluding the tube, trapping between them a body of fluid. The body of fluid is then transported, at ambient pressure, toward the pump outlet. Peristaltic pumps may run continuously, or they may be indexed through partial revolutions to deliver smaller amounts of fluid.

Peristaltic pumps are typically used to pump clean/sterile or aggressive fluids because cross contamination with exposed pump components cannot occur. Some common applications include pumping IV fluids through an infusion device, aggressive chemicals, high solids slurries and other materials where isolation of the product from the environment, and the environment from the product, are critical. It is also used in heart-lung machines to circulate blood during a bypass surgery as the pump does not cause significant hemolysis.

Peristaltic pumps are also used in a wide variety of industrial applications. Their unique design makes them especially suited to pumping abrasives and viscous fluids.

The minimum gap between the roller and the housing determines the maximum squeeze applied on the tubing. The amount of squeeze applied to the tubing affects pumping performance and the tube life—more squeezing decreases the tubing life dramatically, while less squeezing can cause the pumped medium to slip back, especially in high pressure pumping, and decreases the efficiency of the pump dramatically and the high velocity of the slip back typically causes premature failure of the hose. Therefore, this amount of squeeze becomes an important design parameter.

The term "occlusion" is used to measure the amount of squeeze. It is either expressed as a percentage of twice the wall thickness, or as an absolute amount of the wall that is squeezed.

Let y denote an occlusion, g denote minimum gap between the roller and the housing, and t denote wall thickness of the tubing. Then $y=2t-g$, when expressed as the absolute amount of squeeze, and $y=(2t-g)/(2t)\times 100$, when expressed as a percentage of twice the wall thickness. The occlusion is typically 10 to 20%, with a higher occlusion for a softer tube material and a lower occlusion for a harder tube material.

Thus for a given pump, the most critical tubing dimension becomes the wall thickness. An interesting point here is that the inside diameter of the tubing is not an important design parameter for the suitability of the tubing for the pump. Therefore, it is common for more than one ID be used with a pump, as long as the wall thickness remains the same.

Inside diameter: for a given rpm of the pump, a tube with larger inside diameter (ID) will give higher flow rate than one with a smaller inside diameter. Intuitively the flow rate is a function of the cross section area of the tube bore.

The flow rate in a peristaltic pump is determined by many factors, such as the tube internal diameter (ID), where higher flow rate are obtained with larger ID, the pump head's outer diameter (OD), where higher flow are obtained with larger OD, and the pump head's rotation speed, where higher flow rate are obtained with higher rotation speed. It is recognized that increasing the number of rollers typically does not increase the flow rate. Rather it typically decreases the flow rate by reducing the effective (fluid-pumping) circumference of the head. Increasing rollers typically decreases the amplitude of the fluid pulsing at the outlet by increasing the frequency of the pulsed flow.

The length of tube (measured from initial pinch point near the inlet to the final release point near the outlet) does not affect the flow rate. However, a longer tube implies more pinch points between inlet and outlet, increasing the pressure that the pump can generate.

The present embodiments contemplate any of several variations of peristaltic pumps. Hose pumps can typically operate against up to 16 bar in continuous service, use shoes (rollers only used on low pressure types) and have casings filled with lubricant to prevent abrasion of the exterior of the pump tube and to aid in the dissipation of heat, and use reinforced tubes, often called "hoses". This class of pump is often called a "hose pump". The advantage with the hose pumps over the roller pumps is the high operating pressure of up to 16 bar. With rollers max pressure can arrive up to 12 Bar. Tube pumps are typically lower pressure peristaltic pumps having dry casings and use rollers along with non-reinforced, extruded tubing. This class of pump is sometimes called a "tube pump" or "tubing pump". These pumps employ rollers to squeeze the tube. Except for the 360° eccentric pump design as described below, these pumps have a minimum of 2 rollers 180° apart, and may have as many as 8, or even 12 rollers. Increasing the number of rollers increase the pressure pulse frequency of the pumped fluid at the outlet, thereby decreasing the amplitude of pulsing.

The present embodiments contemplate any of several variations of roller designs. In a fixed occlusion pump, the rollers have a fixed locus as it turns, keeping the occlusion constant as it squeezes the tube. In spring-loaded rollers, the rollers in this pump are mounted on a spring. This design helps overcome the variations in the tube wall thickness over a broader range. Regardless of the variations, the roller imparts the same amount of stress on the tubing that is proportional to the spring constant, making this a constant stress operation. The spring is selected to overcome not only the hoop strength of the tubing, but also the pressure of the pumped fluid.

The operating pressure of these pumps is determined by the tubing and by the motor's ability to overcome the hoop strength of the tubing and the fluid pressure.

While the embodiments above are described with a particular emphasis to peristaltic pumps, it is to be understood that other pumps, such as, but not limited to, positive displacement pumps, impulse pumps, velocity pumps, gravity pumps, steam pumps and valveless pumps, can be employed.

Medium Perfusate

Depending on the type of cell source grown in the device of the present invention a specific medium perfusate is used.

Cell culture medium often contains fetal bovine serum (FBS) that provides attachment factors, fatty acids, growth factors, hormones, and albumin. FBS can usually be replaced with serum replacement (e.g. KO-serum) that is composed of amino acids, vitamins, and trace elements in addition to transferrin, insulin, and lipid-rich bovine serum albumin. While both transferrin and insulin are produced in bacteria using recombinant technology, albumin is usually animal derived. However, plant and bacteria-derived recombinant human albumin (e.g. Cellastim™) are available through several companies, including Sigma-Aldrich (St. Louis, MO).

Chicken embryonic fibroblast (CEF) medium is traditionally composed of M199 or DMEM/F12 medium supplemented with 15% FBS, and glutamine. However, serum-free medium for the growth of mammalian fibroblasts is now readily available. Medium is for mammalian cells (e.g. cow, pig) is composed of M199 supplemented with 0.5 mg/mL albumin, 0.6 μM linoleic acid, 0.6 μg/mL lecithin, 5 ng/mL bFGF, 5 ng/mL EGF, 30 pg/mL TGFβ1, 7.5 mM glutamine, 1 μg/mL hydrocortisone, 50 μg/mL ascorbic acid, and 5 μg/mL insulin. This medium PCS-201-040 is available from ATCC (Manassas, VA) and is reported to support 4-fold faster proliferation of human fibroblasts. Under some conditions, insulin could be replaced with IGF-1, or the stabilized Long R3 IGF-1 (Sigma). EGF can be replaced with the EGF-R agonist NSC-228155 (Sakanyan et al. Sci. Reports. 2014). FGF can similarly be replaced with a small molecule or synthetic agonist such as C19-jun (Ballinger et al. Nature. Biotech. 1999). Chicken hepatocytes are similarly supported by a serum-free culture medium designed for human and mouse hepatocytes. Medium is composed of Williams E basal medium supplemented with albumin, insulin, transferrin, and hydrocortisone (1).

Oxygenator

An oxygenator is a medical device that is capable of exchanging oxygen and carbon dioxide in the blood of human patient during surgical procedures that may necessitate the interruption or cessation of blood flow in the body, a critical organ or great blood vessel. These organs can be the heart, lungs or liver, while the great vessels can be the aorta, pulmonary artery, pulmonary veins or vena cava. An oxygenator is typically utilized by a perfusionist in cardiac surgery in conjunction with the heart-lung machine. However, oxygenators can also be utilized in extracorporeal membrane oxygenation in neonatal intensive care units by nurses (www (dot)en(dot)wikipedia(dot)org/w iki/Oxygenator, incorporated hereinafter as reference). For most cardiac operations such as coronary artery bypass grafting, the cardiopulmonary bypass is performed using a heart-lung machine (or cardiopulmonary bypass machine). The heart-lung machine serves to replace the work of the heart during the open bypass surgery. The machine replaces both the heart's pumping action and the lungs' gas exchange function. Since the heart is stopped during the operation, this permits the surgeon to operate on a bloodless, stationary heart.

One component of the heart-lung machine is the oxygenator. The oxygenator component serves as the lung, and is designed to expose the blood or perfusion medium to oxygen and remove carbon dioxide. It is disposable and contains about 2-4 $m^2$ of a membrane permeable to gas but impermeable to blood, in the form of hollow fibers. Blood flows on the outside of the hollow fibers, while oxygen flows in the opposite direction on the inside of the fibers. As the blood passes through the oxygenator, the blood comes into intimate contact with the fine surfaces of the device itself. Gas containing oxygen and medical air is delivered to the interface between the blood and the device, permitting the blood cells to absorb oxygen molecules directly.

In some embodiments of the present invention, an oxygenator is provided as mass transfer device 12 to exchange of gases in the medium used to grow the cells.

In various embodiments of the present invention the gases are selected from a group consisting of oxygen ($O_2$), carbon dioxide ($CO_2$), nitrogen ($N_2$) and any combination thereof.

In a preferred embodiment of the present invention the ratio:percentage of each gas that need to be maintained is of $O_2$ from about 21% to about 95%, $CO_2$ from about 0% to about 10% and $N_2$ from about 0% to about 80%.

In a preferred embodiment of the present invention the ratio:percentage of each gas that need to be maintained is $O_2$ at about 80%, $CO_2$ at about 5% and $N_2$ at about 15%.

Bubble Trap

Unwanted bubbles inadvertently introduced into a microfluidic system can negatively affect device operation and experimental outcome. This is especially true for microfluidic perfusion culture systems, which typically require sterilization and pre-conditioning of the surface prior to cell seeding, time to allow for cell attachment, and then take several days to observe the growth rate and cell morphologies. Bubbles can form at the connection between the device and tubing or can be introduced when unplugging connections to transfer the device between the microscope and incubator. The bubbles are cytotoxic to the cells and can potentially rupture their cell membranes.

One solution to mitigate bubble-based device failure is to integrate microfluidic features to prevent bubbles from entering critical areas of a device. There are, in general, two different approaches: trapping versus debubbling. A bubble trap is a structure integrated into the flow system that halts further progress of a bubble through a device. It has been demonstrated a simple, easily implemented bubble trap by making a chamber at the connection point between external tubing and their device. This approach has the advantage that device operation is maintained while the bubbles are trapped. The alternative is to actively remove the bubbles from the system. This is advantageous since the bubble trap does not remove bubbles from the system, so that when the bubble trap completely fills with bubbles, any additional bubbles would be sent through the system. Active bubble removal can be achieved based on gas permeability of the material forming the fluidic circuit 102 (e.g., PDMS). In these embodiments, positive pressure is applied to force bubbles out of fluidic circuit 102.

In an embodiment of the present invention, the system comprises a dedicated part for the removal of bubbles selected from the group consisting of: bubble trap, debubbler, and any combination thereof.

Heat Exchanger

A heat exchanger is a device used to transfer heat between one or more fluids. The fluids may be separated by a solid wall, such as plastic or metal tubing, to prevent mixing or they may be in direct contact. They are widely used in space heating, refrigeration, air conditioning, power stations, chemical plants, petrochemical plants, petroleum refineries, natural-gas processing, and sewage treatment. The classic example of a heat exchanger is found in an internal combustion engine in which a circulating fluid known as engine coolant flows through radiator coils and air flows past the coils, which cools the coolant and heats the incoming air (www(dot) en(dot)wikipedia(dot)org/wiki/Heat_exchanger#Fluid_heat_exchangers, incorporated herein as reference).

Flow arrangement: There are three primary classifications of heat exchangers according to their flow arrangement. In parallel-flow heat exchangers, the two fluids enter the exchanger at the same end, and travel in parallel to one another to the other side. In counter-flow heat exchangers the fluids enter the exchanger from opposite ends. The counter current design is the most efficient, in that it can transfer the most heat from the heat (transfer) medium per unit mass due to the fact that the average temperature difference along any unit length is higher. See countercurrent exchange. In a cross-flow heat exchanger, the fluids travel roughly perpendicular to one another through the exchanger.

For efficiency, heat exchangers are designed to maximize the surface area of the wall between the two fluids, while minimizing resistance to fluid flow through the exchanger. The exchanger's performance can also be affected by the addition of fins or corrugations in one or both directions, which increase surface area and may channel fluid flow or induce turbulence.

The driving temperature across the heat transfer surface varies with position, but an appropriate mean temperature can be defined. In most simple systems this is the "log mean temperature difference" (LMTD). Sometimes direct knowledge of the LMTD is not available and the Number of Transfer Units (NTU) method is used.

Types: Double pipe heat exchangers are the simplest exchangers used in industries. On one hand, these heat exchangers are cheap for both design and maintenance, making them a good choice for small industries. On the other hand, their low efficiency coupled with the high space occupied in large scales, has led modern industries to use more efficient heat exchangers like shell and tube or plate. However, since double pipe heat exchangers are simple, they are used to teach heat exchanger design basics to students as the fundamental rules for all heat exchangers are the same. To start the design of a double pipe heat exchanger, the first step is to calculate the heat duty of the heat exchanger. It must be noted that for easier design, it's better to ignore heat loss to the environment for initial design.

Shell and tube heat exchanger: shell and tube heat exchangers consist of series of tubes. One set of these tubes contains the fluid that must be either heated or cooled. The second fluid runs over the tubes that are being heated or cooled so that it can either provide the heat or absorb the heat required. A set of tubes is called the tube bundle and can be made up of several types of tubes: plain, longitudinally finned, etc. Shell and tube heat exchangers are typically used for high-pressure applications (with pressures greater than 30 bar and temperatures greater than 260° C.). This is because the shell and tube heat exchangers are robust due to their shape.

Several thermal design features must be considered when designing the tubes in the shell and tube heat exchangers: There can be many variations on the shell and tube design. Typically, the ends of each tube are connected to plenums (sometimes called water boxes) through holes in tubesheets. The tubes may be straight or bent in the shape of a U, called U-tubes.

Tube diameter: Using a small tube diameter makes the heat exchanger both economical and compact. However, it is more likely for the heat exchanger to foul up faster and the small size makes mechanical cleaning of the fouling difficult. To prevail over the fouling and cleaning problems, larger tube diameters can be used. Thus to determine the tube diameter, the available space, cost and fouling nature of the fluids must be considered.

Tube thickness: The thickness of the wall of the tubes is usually determined to ensure:

There is enough room for corrosion

That flow-induced vibration has resistance

Axial strength

Availability of spare parts

Hoop strength (to withstand internal tube pressure)

Buckling strength (to withstand overpressure in the shell)

Tube length: heat exchangers are usually cheaper when they have a smaller shell diameter and a long tube length. Thus, typically there is an aim to make the heat exchanger as long as physically possible whilst not exceeding production capabilities. However, there are many limitations for this, including space available at the installation site and the need to ensure tubes are available in lengths that are twice the required length (so they can be withdrawn and replaced). Also, long, thin tubes are difficult to take out and replace.

Tube pitch: when designing the tubes, it is practical to ensure that the tube pitch (i.e., the centre-centre distance of adjoining tubes) is not less than 1.25 times the tubes' outside diameter. A larger tube pitch leads to a larger overall shell diameter, which leads to a more expensive heat exchanger.

Tube corrugation: this type of tubes, mainly used for the inner tubes, increases the turbulence of the fluids and the effect is very important in the heat transfer giving a better performance.

Tube Layout: refers to how tubes are positioned within the shell. There are four main types of tube layout, which are, triangular (30°), rotated triangular (60°), square (90°) and rotated square (45°). The triangular patterns are employed to give greater heat transfer as they force the fluid to flow in a more turbulent fashion around the piping. Square patterns are employed where high fouling is experienced and cleaning is more regular.

Baffle Design: baffles are used in shell and tube heat exchangers to direct fluid across the tube bundle. They run perpendicularly to the shell and hold the bundle, preventing the tubes from sagging over a long length. They can also prevent the tubes from vibrating. The most common type of baffle is the segmental baffle. The semicircular segmental baffles are oriented at 180 degrees to the adjacent baffles forcing the fluid to flow upward and downwards between the tube bundle. Baffle spacing is of large thermodynamic concern when designing shell and tube heat exchangers. Baffles must be spaced with consideration for the conversion of pressure drop and heat transfer. For thermo economic optimization it is suggested that the baffles be spaced no closer than 20% of the shell's inner diameter. Having baffles spaced too closely causes a greater pressure drop because of flow redirection. Consequently, having the baffles spaced too far apart means that there may be cooler spots in the corners between baffles. It is also important to ensure the baffles are spaced close enough that the tubes do not sag. The other main type of baffle is the disc and doughnut baffle, which consists of two concentric baffles. An outer, wider baffle looks like a doughnut, whilst the inner baffle is shaped like a disk. This type of baffle forces the fluid to pass around each side of the disk then through the doughnut baffle generating a different type of fluid flow. Fixed tube liquid-cooled heat exchangers especially suitable for marine and harsh applications can be assembled with brass shells, copper tubes, brass baffles, and forged brass integral end hubs.

Plate heat exchangers: another type of heat exchanger is the plate heat exchanger. These exchangers are composed of many thin, slightly separated plates that have very large surface areas and small fluid flow passages for heat transfer. Advances in gasket and brazing technology have made the plate-type heat exchanger increasingly practical. In HVAC applications, large heat exchangers of this type are called plate-and-frame; when used in open loops, these heat exchangers are normally of the gasket type to allow periodic disassembly, cleaning, and inspection. There are many types of permanently bonded plate heat exchangers, such as dip-brazed, vacuum-brazed, and welded plate varieties, and they are often specified for closed-loop applications such as refrigeration. Plate heat exchangers also differ in the types of plates that are used, and in the configurations of those plates. Some plates may be stamped with "chevron", dimpled, or other patterns, where others may have machined fins and/or grooves. When compared to shell and tube exchangers, the stacked-plate arrangement typically has lower volume and cost. Another difference between the two is that plate exchangers typically serve low to medium pressure fluids, compared to medium and high pressures of shell and tube. A third and important difference is that plate exchangers employ more countercurrent flow rather than cross current flow, which allows lower approach temperature differences, high temperature changes, and increased efficiencies.

Plate and shell heat exchanger: A third type of heat exchanger is a plate and shell heat exchanger, which combines plate heat exchanger with shell and tube heat exchanger technologies. The heart of the heat exchanger contains a fully welded circular plate pack made by pressing and cutting round plates and welding them together. Nozzles carry flow in and out of the platepack (the 'Plate side' flowpath). The fully welded platepack is assembled into an outer shell that creates a second flowpath (the 'Shell side'). Plate and shell technology offers high heat transfer, high pressure, high operating temperature, uling and close approach temperature. In particular, it does completely without gaskets, which provides security against leakage at high pressures and temperatures.

Adiabatic wheel heat exchanger: a fourth type of heat exchanger uses an intermediate fluid or solid store to hold heat, which is then moved to the other side of the heat exchanger to be released. Two examples of this are adiabatic wheels, which consist of a large wheel with fine threads rotating through the hot and cold fluids, and fluid heat exchangers.

Plate fin heat exchanger: this type of heat exchanger uses "sandwiched" passages containing fins to increase the effectiveness of the unit. The designs include crossflow and counterflow coupled with various fin configurations such as straight fins, offset fins and wavy fins.

Plate and fin heat exchangers are usually made of aluminum alloys, which provide high heat transfer efficiency. The material enables the system to operate at a lower temperature difference and reduce the weight of the equipment. Plate and fin heat exchangers are mostly used for low temperature services such as natural gas, helium and oxygen liquefaction plants, air separation plants and transport industries such as motor and aircraft engines.

Advantages of plate and fin heat exchangers:

- High heat transfer efficiency especially in gas treatment
- Larger heat transfer area
- Approximately 5 times lighter in weight than that of shell and tube heat exchanger.
- Able to withstand high pressure Disadvantages of plate and fin heat exchangers:

- Might cause clogging as the pathways are very narrow
- Difficult to clean the pathways
- Aluminum alloys are susceptible to Mercury Liquid Embrittlement Failure Pillow plate heat exchanger: a pillow plate exchanger is commonly used in the dairy industry for cooling milk in large direct-expansion stainless steel bulk tanks. The pillow plate allows for cooling across nearly the entire surface area of the tank, without gaps that would occur between pipes welded to the exterior of the tank.

The pillow plate is constructed using a thin sheet of metal spot-welded to the surface of another thicker sheet of metal. The thin plate is welded in a regular pattern of dots or with a serpentine pattern of weld lines. After welding the enclosed space is pressurized with sufficient force to cause the thin metal to bulge out around the welds, providing a space for heat exchanger liquids to flow, and creating a characteristic appearance of a swelled pillow formed out of metal.

Fluid heat exchangers: this is a heat exchanger with a gas passing upwards through a shower of fluid (often water), and the fluid is then taken elsewhere before being cooled. This is commonly used for cooling gases whilst also removing certain impurities, thus solving two problems at once. It is widely used in espresso machines as an energy-saving method of cooling super-heated water to use in the extraction of espresso.

Waste heat recovery units: a Waste Heat Recovery Unit (WHRU) is a heat exchanger that recovers heat from a hot gas stream while transferring it to a working medium, typically water or oils. The hot gas stream can be the exhaust gas from a gas turbine or a diesel engine or a waste gas from industry or refinery.

Big systems with high volume and temperature gas streams, typical in industry, can benefit from Steam Rankine Cycle (SRC) in a WHRU, but these cycles are too expensive for small systems. The recovery of heat from low temperature systems requires different working fluids than steam.

An Organic Rankine Cycle (ORC) WHRU can be more efficient at low temperature range using Refrigerant that boil at lower temperatures than water. Typical organic refrigerants are Ammonia, Pentafluoropropane (R-245fa and R-245ca), and Toluene.

The refrigerant is boiled by the heat source in the Evaporator to produce super-heated vapor. This fluid is expanded in the turbine to convert thermal energy to kinetic energy, which is converted to electricity in the electrical generator. This energy transfer process decreases the temperature of the refrigerant that, in turn, condenses. The cycle is closed and completed using a pump to send the fluid back to the evaporator.

Dynamic scraped surface heat exchanger: another type of heat exchanger is called "(dynamic) scraped surface heat exchanger". This is mainly used for heating or cooling with high-viscosity products, crystallization processes, evaporation and high-fouling applications. Long running times are achieved due to the continuous scraping of the surface, thus avoiding fouling and achieving a sustainable heat transfer rate during the process.

Phase-change heat exchangers: In addition to heating up or cooling down fluids in just a single phase, heat exchangers can be used either to heat a liquid to evaporate (or boil) it or used as condensers to cool a vapor and condense it to a liquid. In chemical plants and refineries, reboilers used to heat incoming feed for distillation towers are often heat exchangers.

Distillation set-ups typically use condensers to condense distillate vapors back into liquid.

Power plants that use steam-driven turbines commonly use heat exchangers to boil water into steam. Heat exchangers or similar units for producing steam from water are often called boilers or steam generators.

In the nuclear power plants called pressurized water reactors, special large heat exchangers pass heat from the primary (reactor plant) system to the secondary (steam plant) system, producing steam from water in the process. These are called steam generators. All fossil-fueled and nuclear power plants using steam-driven turbines have surface condensers to convert the exhaust steam from the turbines into condensate (water) for re-use.

To conserve energy and cooling capacity in chemical and other plants, regenerative heat exchangers can transfer heat from a stream that must be cooled to another stream that must be heated, such as distillate cooling and reboiler feed pre-heating.

This term can also refer to heat exchangers that contain a material within their structure that has a change of phase. This is usually a solid to liquid phase due to the small volume difference between these states. This change of phase effectively acts as a buffer because it occurs at a constant temperature but still allows for the heat exchanger to accept additional heat. One example where this has been investigated is for use in high power aircraft electronics.

Heat exchangers functioning in multiphase flow regimes may be subject to the Ledinegg instability.

Direct contact heat exchangers: Direct contact heat exchangers involve heat transfer between hot and cold streams of two phases in the absence of a separating wall. Thus such heat exchangers can be classified as:

- Gas—liquid
- Immiscible liquid—liquid
- Solid-liquid or solid—gas

Most direct contact heat exchangers fall under the Gas—Liquid category, where heat is transferred between a gas and liquid in the form of drops, films or sprays.

Such types of heat exchangers are used predominantly in air conditioning, humidification, industrial hot water heating, water cooling and condensing plants.

TABLE 1

| Phases | Continuous phase | Driving force | Change of phase | Examples |
|---|---|---|---|---|
| Gas - Liquid | Gas | Gravity | No | Spray columns, packed columns |
| | | | Yes | Cooling towers, falling droplet evaporators |
| | | Forced | No | Spray coolers/quenchers |
| | | Liquid flow | Yes | Spray condensers/ evaporation, jet condensers |

TABLE 1-continued

| Phases | Continuous phase | Driving force | Change of phase | Examples |
|---|---|---|---|---|
| | Liquid | Gravity | No | Bubble columns, perforated tray columns |
| | | | Yes | Bubble column condensers |
| | | Forced | No | Gas spargers |
| | | Gas flow | Yes | Direct contact evaporators, submerged combustion |

Microchannel heat exchangers: Micro heat exchangers, Micro-scale heat exchangers, or microstructured heat exchangers are heat exchangers in which (at least one) fluid flows in lateral confinements with typical dimensions below 1 mm. The most typical such confinement are microchannels, which are channels with a hydraulic diameter below 1 mm. Microchannel heat exchangers can be made from metal, ceramic, and even low-cost plastic. Microchannel heat exchangers can be used for many applications including:

high-performance aircraft gas turbine engines heat pumps air conditioning heat recovery ventilators Helical-coil heat exchangers: Although double-pipe heat exchangers are the simplest to design, the better choice in the following cases would be the helical-coil heat exchanger (HCHE):

The main advantage of the HCHE, like that for the SHE, is its highly efficient use of space, especially when it's limited and not enough straight pipe can be laid.

Under conditions of low flowrates (or laminar flow), such that that the typical shell-and-tube exchangers have low heat-transfer coefficients and becoming uneconomical.

When there is low pressure in one of the fluids, usually from accumulated pressure drops in other process equipment.

When one of the fluids has components in multiple phases (solids, liquids, and gases), which tends to create mechanical problems during operations, such as plugging of small-diameter tubes. Cleaning of helical coils for these multiple-phase fluids can prove to be more difficult than its shell and tube counterpart; however the helical coil unit would require cleaning less often.

These have been used in the nuclear industry as a method for exchanging heat in a sodium system for large liquid metal fast breeder reactors since the early 1970s, using an HCHE device invented by Charles E. Boardman and John H. Germer. There are several simple methods for designing HCHE for all types of manufacturing industries, such as using the Ramachandra K. Patil (et al.) method from India and the Scott S. Haraburda method from the United States.

However, these are based upon assumptions of estimating inside heat transfer coefficient, predicting flow around the outside of the coil, and upon constant heat flux. Yet, recent experimental data revealed that the empirical correlations are quite in agreement for designing circular and square pattern HCHEs. During studies published in 2015, several researchers found that the boundary conditions of the outer wall of exchangers were essentially constant heat flux conditions in power plant boilers, condensers and evaporators; while convective heat transfer conditions were more appropriate in food, automobile and process industries.

In an embodiment of the present invention, the system comprises a dedicated part for the heat conservancy of the medium in a form of a heat exchanger selected from the group consisting of: shell and tube heat exchanger, plate heat exchanger, plate and shell heat exchanger, adiabatic wheel heat exchanger, plate fin heat exchanger, pillow plate heat exchanger, fluid heat exchanger, waste heat recovery units, dynamic scraped surface heat exchanger, phase-change heat exchanger, direct contact heat exchanger, microchannel heat exchanger, helical-coil heat exchanger, spiral heat exchanger, and any combination thereof.

Dialyzer

A dialyzer is a machine equipped with a semipermeable membrane and used for performing dialysis. Dialysis is the process of diffusion of solutes through a semipermeable membrane from a liquid with higher solute concentration on one side of the membrane to a liquid with a lower concentration on the other side. The membranes are semipermeable because they allow some molecules to pass while preventing others from passing. The process has long been used for the molecular separation of small molecules from macromolecules (www(dot)spectrumlabs(dot)com/lit/abc(dot)pdf, incorporated hereinafter as reference) and for extracorporeal support (kidney dialysis, www(dot)en(dot)wikipedia(dot) org/wiki/Dialysis, incorporated hereinafter as reference).

Common dialysis applications utilize tubular forms of membranes and involve placing a "sample" inside the membrane and a "buffer" outside the membrane. The process is run until the desired degree of separation is attained. Molecules smaller than the pores will eventually be equally distributed between the two solutions. Usually, a very large volume of buffer is chosen so that the permeable species are greatly diluted and therefore reduced-to very small concentrations in the remaining sample solution. Commonly, dialysis processes require several hours to complete.

Dialysis Membranes: advances in dialysis membrane development were made as a result of research to provide relief from renal disease by means of hemodialysis, a pressure driven rather than concentration gradient driven process. Greater membrane permeability was achieved through the use of cellulose ester. These solutions could be formulated to yield a wider range of pore sizes. Cellulose ester membranes are now widely used for clinical and laboratory dialysis. Membranes used for dialysis have pore sizes ranging from 100 to 300,000 Daltons (1 to 300 kDa). Sample volumes have also been greatly reduced to allow dialysis of small quantities of precious samples, particularly where maintaining enzyme activity is desired.

Factors that Affect the Rate of Dialysis

Molecular Weight Cut Off and Selectivity: dialysis membranes are characterized by molecular weight cut off (MWCO). MWCO is determined by testing the degree of permeability for several solutes of different molecular weights. The MWCO rating for the membrane is the molecular weight of the smallest solute that is 90% retained in a 17-hour dialysis test. Molecular weight cut off ratings are used as a guide and not an absolute prediction of performance with every type of solute. A membrane MWCO size rating should be chosen as high as possible in order to achieve the maximum dialysis rate while still preventing the loss of the desired solute. Plotting the results of a MWCO test in the form of retention versus the solute molecular weight would ideally produce a sigmoid curve. The steepness of the curve is a measure of the selectivity of the membrane.

Flux and Permeation Rate: the driving force for laboratory dialysis is the concentration difference across the membrane.

The flux (or permeation rate) is directly proportional to the concentration difference, i.e. the greater the difference, the greater the rate. However, the dialysis rate is also influenced by other variables such as:

Diffusion coefficient: different size molecules pass through a membrane at different rates. Larger molecules have a smaller coefficient and a lower rate of diffusion across the membrane.

Molecular shape and charge: linear molecules permeate faster than globular molecules. The pH and ionic strength also affect the rate of dialysis.

Concentration polarization: As molecules diffuse across a membrane, they first move through the bulk of the sample solution to the surface of the membrane. The thin region next to the membrane has a higher concentration of solutes than the bulk solution. This build up is termed "concentration polarization" and is caused by depletion of small molecules at the surface of the membrane. This polarized layer causes resistance to the movement of molecules across the membrane. Finally, after passing through the membrane, the molecule often meets a thin layer of concentration higher than the bulk solution, further slowing the passage. These layers which form on either side of the membrane are called "fluid boundary layers" or "gel layers".

Flow direction and agitation of the solution: sample and buffer that flow perpendicular (or normal) might cause the membrane to plug. Sample and buffer mixing during dialysis can reduce this phenomenon. Mixing can be achieved by either stirring or by passing the sample parallel (or tangential) to the membrane. Parallel flow promotes higher permeation rates. The higher the stirring rate, the higher the dialysis rates (Concentration polarization is reduced by increased stirring rates).

Temperature: higher temperatures promote more rapid molecular movement and therefore increase diffusion rate.

Membrane thickness: membrane properties effect the dialysis rate. Thicker membranes will require a longer time for molecules to pass through.

Membrane surface area: the larger the membrane area, the faster the dialysis rate.

Hydrodynamic properties: viscosity of the fluid and the membrane porosity affect the permeation rate. Low viscosity and high porosity are ideal for higher rates. MWCO Selection: selecting of the correct molecular weight cut off (MWCO) of the membrane is based on the size of the molecular weight of the macromolecules to be retained inside the membrane and the molecular weight of the molecules to be removed. The ratio of the two molecular weights should be a minimum 25 to 1 to achieve the maximum 90% retention.

Tubular Membrane "flat width" Selection: smaller tubing will dialyze more quickly than larger tubing. The latter will dialyze more slowly due to the longer diffusion distances involved.

Albumin is the main carrier protein of growth factors, hormones and fatty acids, and a major cost driver of liquid medium. The system of the present invention is optionally and preferably designed to retain albumin (MW about 66.4 kDa), achievable with a target MWCO of 30 kDa.

In an embodiment of the present invention, the system comprises a dialyzer with surface ranging from 15 to 20,000 $cm^2$ membrane area and a molecular weight cutoff ranging from 10 to 60 kDa.

Dialysate

Dialysate or diffusate is the fluid and solutes in a dialysis process that passes through the membrane in dialysis.

In an embodiment of the present invention, the system comprises a dialysate containing glucose, insulin and growth factors in serum-free medium. Depending on the type of cells being grown in the chamber, a different content of dialysate is prepared in order to respond to the specific needs of the growing cells.

Filtering

Filtering can be effected according to some embodiments of the present invention by any type of filter that can remove contaminants and impurities. Representative examples including, without limitation, carbon filtering and zeolite filtering.

Carbon filtering is a method of filtering that uses a bed of activated carbon to remove contaminants and impurities, using chemical adsorption (www(dot)en(dot)wikipedia(dot)org/wiki/Carbon filtering, incorporated hereinafter as reference).

Each particle/granule of carbon provides a large surface area/pore structure, allowing contaminants the maximum possible exposure to the active sites within the filter media. One pound (454 g) of activated carbon contains a surface area of approximately 100 acres (40 Hectares).

Activated carbon works via a process called adsorption, whereby pollutant molecules in the fluid to be treated are trapped inside the pore structure of the carbon substrate. Carbon filtering is commonly used for water purification, in air purifiers and industrial gas processing, for example the removal of siloxanes and hydrogen sulfide from biogas. It is also used in a number of other applications, including respirator masks, the purification of sugarcane and in the recovery of precious metals, especially gold. Active charcoal carbon filters are most effective at removing chlorine, sediment, volatile organic compounds (VOCs), taste and odor from water. They are not effective at removing minerals, salts, and dissolved inorganic compounds.

Typical particle sizes that can be removed by carbon filters range from 0.5 to 50 micrometres. The particle size will be used as part of the filter description. The efficacy of a carbon filter is also based upon the flow rate regulation. When the water is allowed to flow through the filter at a slower rate, the contaminants are exposed to the filter media for a longer amount of time.

There are 2 predominant types of carbon filters used in the filtration industry: powdered block filters and granular activated filters. In general, carbon block filters are more effective at removing a larger number of contaminants, based upon the increased surface area of carbon. Many carbon filters also use secondary media such as silver to prevent bacteria growth within the filter. Alternatively, the activated carbon itself may be impregnated with silver to provide this bacteriostatic property. Factors that affect the performance of activated carbon are (www(dot) watertreatmentguide(dot)com/activated_carbon_filtration(dot)htm, incorporated hereinafter as reference):

Molecular weight: as the molecular weight increases, the activated carbon adsorbs more effectively because the molecules are lea soluble in water. However, the pore structure of the carbon must be large enough to allow the molecules to migrate within. A mixture of high and low molecular weight molecules should be designed for the removal of the more difficult species.

pH: most organics are less soluble and more readily adsorbed at a lower pH. As the pH increases, removal decreases. A rule of thumb is to increase the size of the carbon bed by twenty percent for every pH unit above neutral (7.0).

Contaminant concentration: the higher the contaminant concentration, the greater the removal capacity of activated carbon. The contaminant molecule is more likely to diffuse into a pore and become adsorbed. As concentrations increase, however, so do effluent leakages. The upper limit for contaminants is a few hundred parts per million. Higher contaminant concentration may require more contact time with the activated carbon. Also, the removal of organics is enhanced by the presence of hardness in the water, so whenever possible, place activated carbon units upstream of the ion removal units. This is usually the case anyway since activated carbon is often used upstream of ion exchange or membranes to remove chlorine.

Particle size: activated carbon is commonly available in 8 by 30 mesh (largest), 12 by 40 mesh (most common), and 20 by 50 mesh (finest). The finer mesh gives the best contact and better removal, but at the expense of higher pressure drop. A rule of thumb here is that the 8 by 30 mesh gives two to three times better removal than the 12 by 40, and 10 to 20 times better kinetic removal than the 8 by 30 mesh.

Flow rate: generally, the lower the flow rate, the more time the contaminant will have to diffuse into a pore and be adsorbed. Adsorption by activated carbon is almost always improved by a longer contact time. Again, in general terms, a carbon bed of 20 by 50 mesh can be run at twice the flow rate of a bed of 12 by 40 mesh, and a carbon bed of 12 by 40 mesh can be run at twice the flow rate of a bed of 8 by 30 mesh.

Temperature: higher water temperatures decrease the solution viscosity and can increase die diffusion rate, thereby increasing adsorption. Higher temperatures can also disrupt the adsorptive bond and slightly decrease adsorption. It depends on the organic compound being removed, but generally, lower temperatures seem to favor adsorption. In an embodiment of the present invention, the system comprises a carbon filter adapted to clean toxins from present in the dialysate.

When zeolite filtering is employed, the portion of the perfusion solution that enters system 200 is passed through zeolite to absorb the ammonia in the solution. Preferably, granular zeolite is employed. The term zeolite is intended to encompass hydrated aluminosilicate minerals that have a micro-porous structure. Natural zeolites are formed where volcanic rocks and ash layers react with alkaline ground water. Granular zeolites suitable for use in the present invention can, for example, be sourced from Zeolite Australia Pty Ltd (PO Box 6 Werris Creek NSW 2341, Australia).

Sensors

Figure 9:
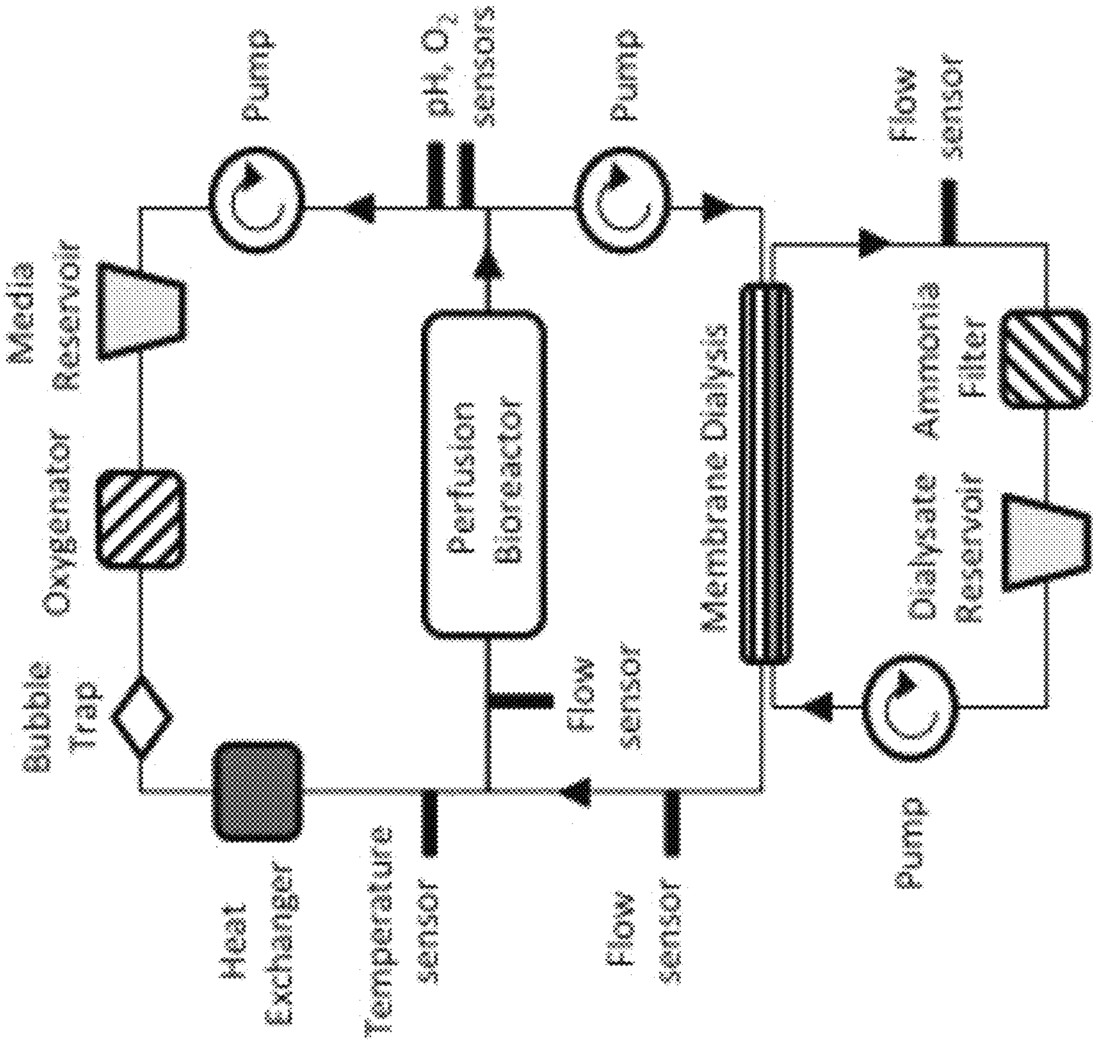
FIG. 9 is a schematic illustration of a system suitable for growing cells as designed in a prototype design, according to some embodiments of the present invention.

In a preferred embodiment of the present invention, system 1000 comprises one or more active sensors (not shown in FIGS. 1A-B, see FIG. 9) that allow continuous monitoring of the cells growing therein. Some examples of sensors comprise, but are not limited to, temperature sensors, pH sensor, volume sensor, video apparatuses, flow sensor, optical sensors, weight sensor, glucose sensor, and protein content sensor.

In a preferred embodiment of the present invention, the system is connected to a main computer, having a non-transitory computer readable medium (CRM), that operates automatically all the daily necessities of the system and provides real-time alarms to dedicated operators. The main computer can be connected and operated remotely via internet/cloud services. In a second embodiment the system is self-contained, with data from sensors analyzed by a local central processing unit (CPU), which changes input parameters such a nutrient, flow, pressure or temperature to adjust cell growth and sensor signal to within desired parameter set, maintaining growth homeostasis.

In a preferred embodiment of the present invention, the system comprises a Closed-loop perfusion circuit composed of a primary perfusion circuit and a secondary dialysis circuit for nutrient and toxin exchange. The primary circuit includes culture medium perfusate that is recirculated using a peristaltic pump through a jacketed cell growth chamber, a membrane oxygenator, a heat exchanger, and a bubble trap. The oxygenator is gassed with a mixture of 80% $O_2$/5% $CO_2$/15% $N_2$ maintaining constant pH. A fraction of the perfusate is diverted to secondary circuit through a dialyzer with a 2200 $cm^2$ membrane area and a 30 kDa molecular weight cutoff at a rate of 3 mL/min/gram cells. The secondary circuit dialyzed the perfusate by counter-current exposure to protein-free dialysate, recirculated through a carbon filter using a third peristaltic pump. Temperature within the system is maintained at 37° C. All the system Cell Types Several types of cells can be grown in the closed-loop perfusion circuit disclosed in the present invention.

Primary Cell Source

Chicken embryonic fibroblasts are widely used for the production of viruses and vaccines. Together with chicken embryonic liver cells they are produced from specific pathogen-free (SPF) embryos and sold by Charles River Laboratories (Wilmington, MA) and other companies. While chicken liver cells show limited proliferation in culture, like their mammalian counterparts, chicken fibroblasts can undergo over 30 population doublings, producing about 2.6 ton of cells before spontaneously immortalizing without becoming tumorigenic. Spontaneously transformed chicken fibroblasts, such as the CSIF cell line generated by the present inventor (e.g., as described in Example 5 of the Examples section which follows), UMNSAH/DF-1 (CRL-12203) can be bought directly from ATTC (Manassas, VA). While the growth potential of fibroblast is excellent, the cells primarily form inedible connective tissue.

Chicken embryonic endothelium can be easily isolated but their growth potential is unknown and can be organ specific. Mouse micro-vascular cells can undergo 30 population doublings, while human cells seldom pass 12 population doublings. Chicken embryonic muscle cells (myocytes) can be similar isolated but have a very limited growth potential. Mouse and human cells seldom pass 12 population doublings. Myogenesis, the formation of new muscle tissue, is uncommon past the neonatal stage of life in most species. Small molecules can conceptually be used to modulate this behavior.

Pluripotent Stem Cell Source

Numerous groups produced chicken embryonic stem cells (cESC) over the last decade (3). Cells are isolated from fertilized chicken eggs and are essentially immortal. Chicken induced pluripotent stem cells (ciPSC) were produced from quail embryonic fibroblasts by reprogramming factors OCT4, NANOG, SOX2, LIN28, KLF4, and C-MYC (4) and more recently chicken fibroblasts using OCT4, KLF4, and C-MYC (5). Cells are essentially immortal but are genetically engineered.

Recently, mouse pluripotent stem cells were induced from fibroblasts using small molecules (6) permitting the differentiation of multiple cell types, including myocytes, hepatocytes, and endothelial cells as well as complex embryoid bodies. Chemical induction of ciPSC offers an alternative approach to convert fibroblasts to other cell types.

Small Molecule-Based Reprogramming

Chemical compounds offer an attractive alternative to growth factors and genetic engineering that are generally used to support cell growth, or to switch one cell type to another through reprogramming or differentiation. Small molecules are less expensive, have lower lot-to-lot variability, are non-immunogenic and are much more stable. In one study, Shan and colleagues used a high content screen to identify FPH1 and FPH2, small molecules that promoted proliferation of primary human hepatocytes (7). This approach is appealing, as small molecules could replace growth factors serum-free medium formulations, dramatically reducing costs while increasing safety.

In a more recent study, Cao and colleagues identified a combination of 9 compounds that induced human fibroblasts to turn into cardiomyocytes (8), while others used a 7 compound combination to transform mouse cells (9). Considering many of the signaling pathways are conserved, a relatively similar combination could be used to transform chicken fibroblasts into myocytes.

Animal Product Free Culture Medium

As mentioned above, cell culture medium often contains fetal bovine serum (FBS) that provides attachment factors, fatty acids, growth factors, hormones, and albumin. FBS can usually be replaced with serum replacement (e.g. KO-serum) that is composed of amino acids, vitamins, and trace elements in addition to transferrin, insulin, and lipid-rich bovine serum albumin. While both transferrin and insulin are produced in bacteria using recombinant technology, albumin is usually animal derived. However, plant and bacteria-derived recombinant human albumin (e.g. Cellastim™) are available through several companies, including Sigma-Aldrich (St. Louis, MO).

Chicken fibroblast medium is traditionally composed of M199 medium supplemented with 10% FBS, tryptose phosphate and glutamine. However, serum-free medium for the growth of mammalian fibroblasts is now readily available. Medium is composed of M199 supplemented with 0.5 mg/mL albumin, 0.6 μM linoleic acid, 0.6 μg/mL lecithin, 5 ng/mL bFGF, 5 ng/mL EGF, 30 pg/mL TGFβ1, 7.5 mM glutamine, 1 μg/mL hydrocortisone, 50 μg/mL ascorbic acid, and 5 μg/mL insulin. This medium PCS-201-040 is available from ATCC (Manassas, VA) and is reported to support 4-fold faster proliferation of human fibroblasts. Chicken hepatocytes are similarly supported by a serum-free culture medium designed for human and mouse hepatocytes. Medium is composed of Williams E basal medium supplemented with albumin, insulin, transferrin, and hydrocortisone.

Perfused culture medium can also include an oxygen carrier. Hemoglobin based oxygen carriers (www(dot)en(dot)wikipedia(dot)org/wiki/Haemoglobin-based oxygen carriers, incorporated hereinafter as reference) include hemoglobin derivatives either recombinant or chemically modified, encapsulated hemoglobin or modified (e.g. cross-linked) red blood cells. Alternatives include Perfluorocarbon based alternatives such as those developed in Nahmias et al. (11) (www(dot)en(dot)wikipedia(dot)or g/wiki/Blood_substitute#Current_therapeutics, incorporated hereinafter as reference)

Figure 8:
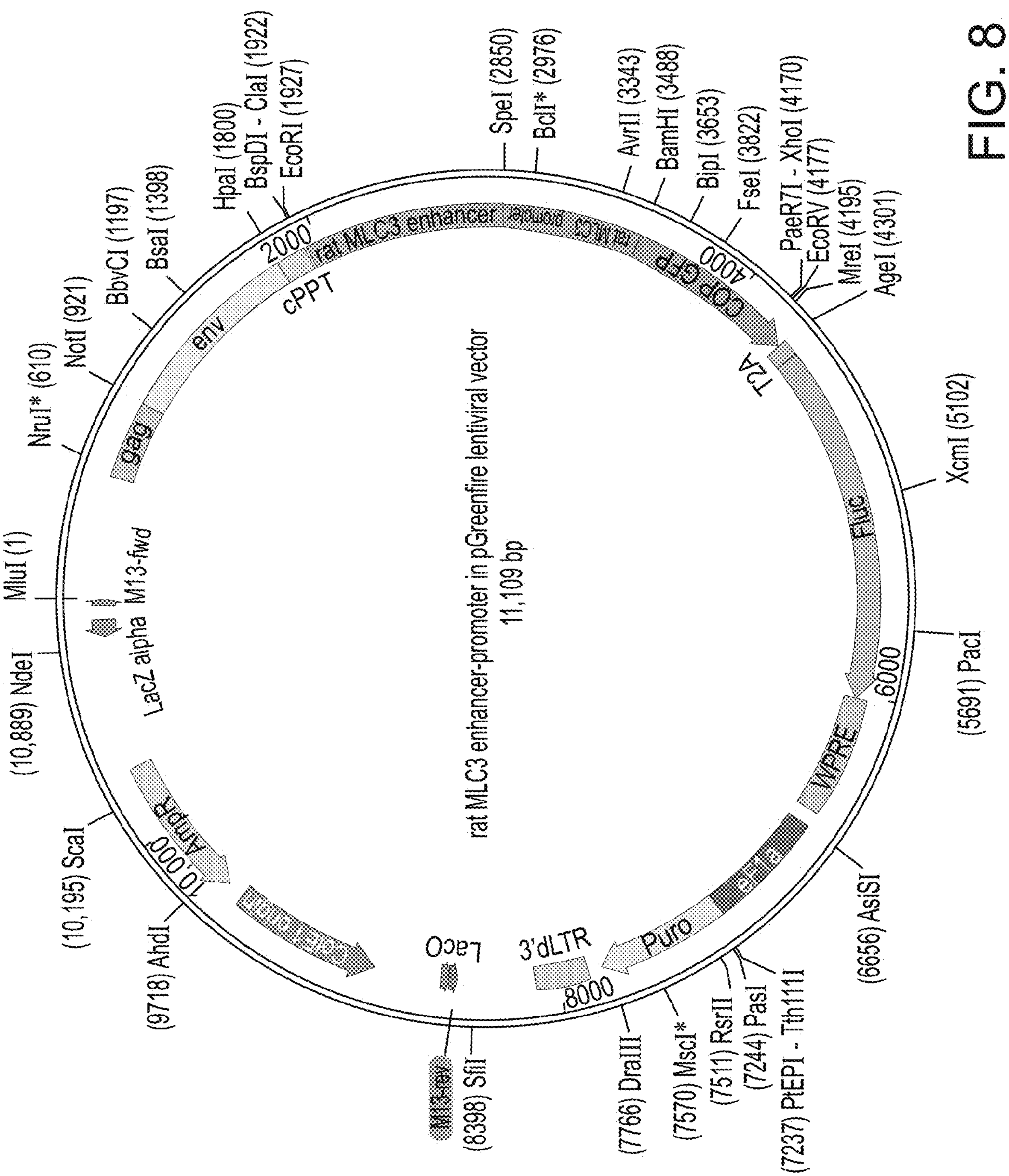
FIG. 8 is a schematic illustration of the rat MLC3 enhancer-promoter in pGreenFire lentiviral vector used to show the conversion of a spontaneously immortalized fibroblast into a myocyte. Shown are the central polypurine tract" (CPPTS) element (in yellow); the rat MLC3 enhancer (in light blue); the rat MLC3 promoter (in orange) and the COP GFP coding sequence (in green). It is noted that this vector can be used to screen for small molecules capable of converting a spontaneously immortalized fibroblast into a myocyte.
Figure 11A:
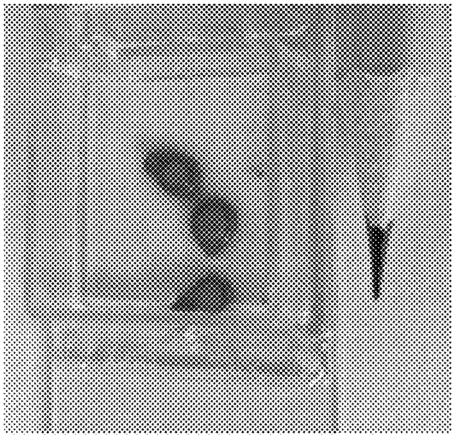
FIGS. 11A-C depict tissue formation and vascularization.
Figure 11B:
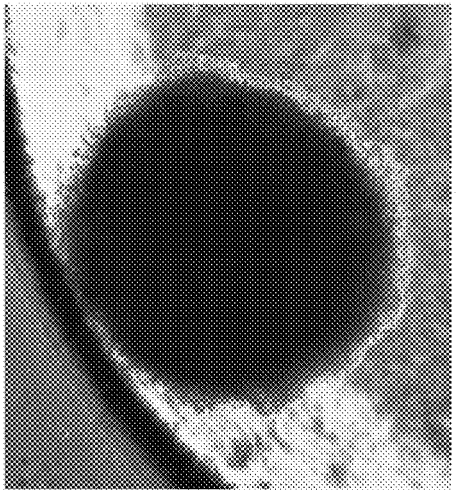
Figure 11C:
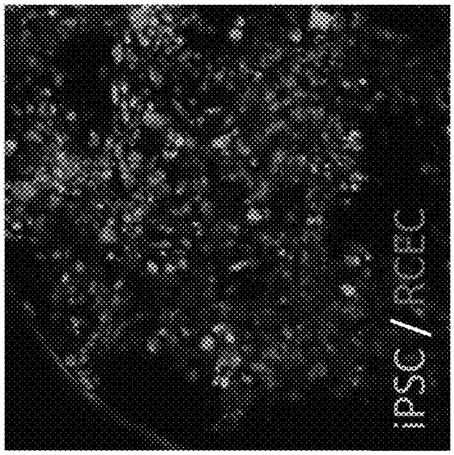
Figure 12:
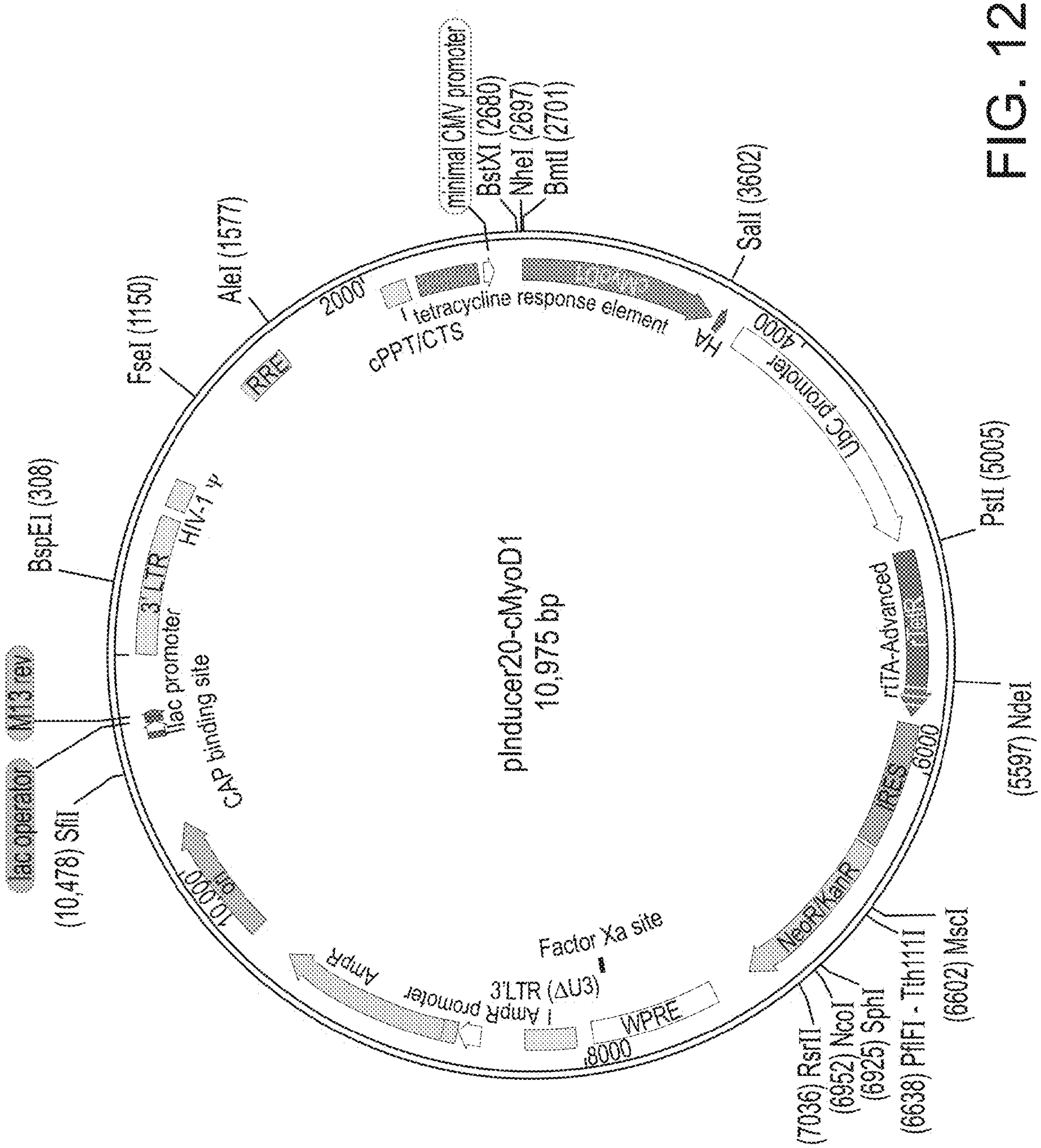
FIG. 12 a schematic illustration of the pInducer20-cMyoD1 nucleic acid construct used to express the chicken MyoD1 in a spontaneously immortalized fibroblast under Dox-induction. Shown are the "central polypurine tract/central termination sequence" (CPPT/CTS) element (in light peach), the tetracycline response element (in Turquoise); the minimal CMV promoter (white arrow head); and the cMyoD1 coding sequence (in orange).

The present inventor has uncovered that a spontaneously immortalized fibroblast, such as chicken fibroblast, can be used to generate fat and muscle cells in-vitro for the generation of edible meat. In addition, the present inventor has uncovered that primary or spontaneously immortalized endothelial cell can be co-cultured with the muscle and fat cells in order to form an edible meat with vascular-like network (tissue vessels) in which the endothelial cells serve as vessels for transfer of nutrients and gasses, such as glucose and oxygen. Example 5 of the Examples section which follows demonstrates the isolation and generation of a spontaneously immortalized chicken embryonic fibroblast cell line having a doubling time of 18±2 hours and at least 90 population doublings (PDs) (FIG. 2E). In addition, as is further described in Example 6 of the Examples section which follows, the present inventor has generated, following laborious experimentations, a serum-free culture medium which can maintain the spontaneously immortalized chicken fibroblast cell line under conditions devoid of any animal and/or human contaminants, while maintaining the fibroblasts in a proliferative state for at least 90 population doublings (FIGS. 3B-F). The present inventor has further envisaged that small molecules can substitute at least some of the components included in the serum-free medium (Examples 2, 3 and 6 of the Examples section which follows). The present inventor was able to successfully generate fully functional adipocyte cells, characterized by a compact (not elongated) shape and the accumulation of neutral lipid content from the spontaneously immortalized chicken embryonic fibroblast cell line in a defined serum-free culture medium which includes oleic acid and a small molecule which activates PPAR-gamma such as IBMX or Rosiglitazone (FIGS. 4A-D, Example 7). The present inventor further generated myocyte cells by upregulating the expression level and activity of the MyoD1 and/or Myogenin polypeptides within the spontaneously immortalized chicken embryonic fibroblast cell line (Examples 3 and 8, FIGS. 6-8, 12 and 5A-E). In addition, as shown in described in Examples 3 and 8 of the Examples section which follows, the present inventor describes a screen for small molecules capable of converting the spontaneously immortalized chicken embryonic fibroblast cell line into myocytes using the rat myosin light chain-3 promoter-enhancer reporter construct (rMLC3-GFP; FIG. 8). Furthermore, the present inventor shows that spontaneously immortalized endothelial cells (e.g., reaching at least 120 population doublings; Example 11), which were co-cultured in serum-free and antibiotic-free culture medium with the spontaneously immortalized fibroblast cell line (Example 12) formed vascular network formation and close cell-cell interactions (FIGS. 11A-C). Furthermore, the present inventor describes a hybrid plant-based meat substitute product with in-vitro generated fat (Example 9), and patty or nuggets from the cultured fibroblasts which were induced towards differentiation into muscle and/or fat cells in a suspension culture devoid of microcarriers (Example 10).

According to an aspect of some embodiments of the invention, there is provided an in-vitro method of generating an adipocyte cell from a fibroblast, comprising culturing a spontaneously immortalized fibroblast in a serum-free medium comprising oleic acid and a peroxisome proliferator-activated receptor gamma (PPAR-gamma) agonist or activator thereof, thereby generating the adipocyte cell.

As used herein the phrase "spontaneously immortalized fibroblast" refers to a fibroblast cell which is capable of undergoing unlimited cell division, and preferably also cell expansion, without being subjected to man-induced mutation e.g., genetic manipulation, causing the immortalization.

It should be noted that normally, primary fibroblast cells are capable of a limited cell division, and thus undergo cellular senescence after about 30 population doublings (e.g., 10 passages). Methods of generating immortalized fibroblastoid cell lines include genetic manipulation by introduction of a telomerase gene, or SV40, or HPVE6/E7 gene using known methods.

According to some embodiments of the invention, the fibroblast is an avian fibroblast.

According to some embodiments of the invention, the avian is selected from the group consisting of: chicken, duck, goose, and quail.

According to some embodiments of the invention, the fibroblast is a chicken embryonic fibroblast.

According to some embodiments of the invention, the spontaneously immortalized fibroblast is non-genetically modified.

As used herein the phrase "non-genetically modified" refers to not being subject to man-made genetic manipulation (e.g., transformation) of the cell.

PPAR is subfamily of the nuclear receptor superfamily of transcription factors, plays important roles in lipid and glucose metabolism, and has been implicated in obesity-related metabolic diseases such as hyperlipidemia, insulin resistance, and coronary artery disease.

PPARγ (peroxisome proliferator-activated receptor gamma) is a fatty acid-activated member of the PPAR subfamily. It is expressed at low levels in most physiological systems, including the central nervous system (CNS), endocrine system, gastrointestinal system, reproductive system, cardiopulmonary system and metabolic tissues, but is most highly expressed in brown and white adipose tissue (Elbrecht A, et al. 1996; "Molecular cloning, expression and characterization of human peroxisome proliferator activated receptors gamma 1 and gamma 2". Biochem. Biophys. Res. Commun. 224 431-7 V).

As used herein the phrase "PPAR-gamma activator" refers to an agent which induces the signaling pathway of PPAR-gamma leading to activation of PPAR-gamma.

According to some embodiments of the invention, an activator of PPAR-gamma does not need to directly bind the ligand-binding domain of PPAR-gamma, but can induce the PPAR-gamma signaling pathway leading to activation of PPAR-gamma by endogenous ligand(s).

For example, a PPAR-gamma activator can be PPAR-gamma agonist.

As used herein the phrase "PPAR-gamma agonist" refers to an agent which binds to the ligand-binding domain of PPAR-gamma.

It should be noted that upon binding of the agonist to the ligand-binding domain of PPAR-gamma, the PPAR-gamma protein undergoes a conformational change resulting in activation of PPAR-gamma.

For example, activation of PPAR-gamma (a transcription factor) can be detected by monitoring expression of PPAR-gamma target genes.

Methods of qualifying agonists or activators of PPAR-gamma include, but are not limited to using a GAL4-PPAR-gamma reporter, a LanthaScreen TR-FRET competitive binding assay (ThermoFisher, PV4894), using a GFP-reporter driven by PPAR response element (PPRE), or by checking the expression of target genes, essentially as described in Goldwasser et al. PLoS One 2010, Volume 5, Issue 8, e12399, which is fully incorporated herein by reference).

Non-limiting examples of PPARγ (gamma) target genes, include genes related to adipogenesis (e.g., ADIPOQ, LPL, NR1H3, and UCP1); genes related to fatty Acid Metabolism (e.g., ACADL, ACADM, ACOX1, ACOX3, ACSL1, ACSL3, ACSL4, ACSL5, CPT1A, CPT1B, CPT2, CYP27A1, CYP4A11, CYP7A1, EHHADH, FADS2, GK, and SCD); genes related to lipid transport (e.g., ADIPOQ, ANGPTL4, APOE, DGAT1, LPL, NR1H3, and OLR1); genes related to cell proliferation (e.g., CLU, ELN, HSPD1, and TXNIP); genes related to insulin signaling (e.g., CPT1A, DGAT1, PCK1, and SORBS1) and other genes such as MMP9 and PCK1.

According to some embodiments of the invention, the PPAR-gamma agonist or activator is a small molecule.

According to some embodiments of the invention, the small molecule is selected from the group consisting of Thiazolidinedione, 3-Isobutyl-1-methylxanthine (IBMX), phenamil, GW7845, RG14620, and Harmine.

Thiazolidinediones (also known as "Glitazones") are a class of medications that act by activating PPARs (peroxisome proliferator-activated receptors), with greatest specificity for PPARγ (PPAR-gamma, PPARG). The endogenous ligands for these receptors are free fatty acids (FFAs) and eicosanoids.

According to some embodiments of the invention, the Thiazolidinedione is provided at a concentration in the range of about 20 nM to about 120 μM, e.g., from 50 nM to 100 μM, e.g., from 100 nM to 50 μM, e.g., from 1 μM to 50 μM, e.g., in the range of 0.5-30 μM, e.g., in the range of 0.5-25 μM, e.g., about 0.5 μM, about 1 μM, about 5 μM, about 10 μM, about 15 μM.

According to some embodiments of the invention, the Thiazolidinedione is selected from the group consisting of Pioglitazone (Actos), Rosiglitazone (Avandia), Lobeglitazone (Dulie), Troglitazone (Rezulin), Ciglitazone, Darglitazone, Englitazone, Netoglitazone, and Rivoglitazone.

According to some embodiments of the invention, the small molecule is rosiglitazone.

According to some embodiments of the invention, the concentration of rosiglitazone is between 1-10 μM, e.g., about 5 μM.

According to some embodiments of the invention, the concentration of troglitazone is between 0.5-10 μM, e.g., about 0.5-5 μM, e.g., about 1 μM.

According to some embodiments of the invention, the PPAR-gamma agonist or activator is selenium.

Oleic acid is a naturally-occurring fatty acid, classified as monounsaturated omega-9 fatty acid, abbreviated with a lipid number of 18:1 cis-9.

According to some embodiments of the invention, the concentration of oleic acid which is used in the serum-free medium of some embodiments of the invention is from about 50 μM to about 1000 μM, e.g., between 200-400 μM.

According to some embodiments of the invention, the culturing of the fibroblast is for at least 4 days, e.g., for at least 5, 6, 7, 8, 9, 10, 15, 20 or more days.

It should be noted that for generation of a cultured edible meat the medium used in the method of generating an adipocyte cell should be well-defined, and serum-free. Well-defined culture medium can be prepared by using recombinant, and/or synthetically and/or purified agents. Since serum is obtained from a living organism, e.g., a human being or an animal, it is subject to batch-to-batch variations, and may further include animal or human contaminants, such as bacterial, viral or fungal infections. Accordingly, it is preferred to use a serum-free medium.

According to some embodiments of the invention, the serum-free medium is devoid of animal contaminants.

According to some embodiments of the invention, the serum-free medium is devoid of human contaminants.

According to some embodiments of the invention, the serum-free medium is devoid any antibiotic drug.

According to some embodiments of the invention, for the adipocyte differentiation the serum-free medium can include insulin, and optionally also bFGF.

According to some embodiments of the invention, for the adipocyte differentiation the serum-free medium can include selenium, and optionally also insulin.

According to some embodiments of the invention, the serum-free medium for culturing the spontaneously immortalized chicken fibroblasts comprises insulin or a substitute thereof, and basic fibroblast growth factor (bFGF) or a substitute thereof, and at least one additional agent selected from the group consisting of dexamethasone, transferrin, selenium, epidermal growth factor (EGF) or a substitute thereof, and Prostaglandin E2 (PGE2).

As used herein the term "insulin" refers to the mature insulin polypeptide having A chain and B chain, which are covalently linked via two disulfide bonds. Also known as CAS Number 11061-68-0; EC Number 234-279-7; MDL number MFCD00131380. The precursor polypeptide preproinsulin is cleaved to remove the precursor signal peptide, and then the proinsulin is post-translationally cleaved into three peptides: the B chain and A chain peptides, which are covalently linked via two disulfide bonds to form insulin, and C-peptide. Binding of insulin to the insulin receptor (INSR) stimulates glucose uptake. There are 4 polypeptide variants, encoding the same protein: variant 1 [GenBank Accession No. NM_000207.2 (SEQ ID NO: 13), GenBank Accession No. NP_000198.1 (SEQ ID NO: 14)], variant 2 [GenBank Accession No. NM_001185097.1 (SEQ ID NO: 15), GenBank Accession No. NP_001172026.1 (SEQ ID NO: 16)]; variant 3 [GenBank Accession No. NM_001185098.1 (SEQ ID NO: 17), GenBank Accession No. NP_001172027.1 (SEQ ID NO: 18)]; and variant 4 [GenBank Accession No. NM_001291897.1 (SEQ ID NO: 19), GenBank Accession No. NP_001278826.1 (SEQ ID NO: 20)]. Insulin can be provided from various suppliers such as Sigma-Aldrich (e.g., recombinant human insulin Catalogue Number 91077C).

According to some embodiments of the invention, the insulin substitute comprises IGF-1 (Sigma 1146) or a stabilized Long R3 IGF-1 (Sigma 11271)

According to some embodiments of the invention, the insulin is provided at a concentration of $2.5\times10^{-5}$ IU/mL to 1 IU/mL, e.g., between 0.1 IU/mL to about 0.5 IU/mL, e.g., about 0.24-0.3 IU/mL. It should be noted that IU/mL is an abbreviation of "International Units Per Millilitre (milliliter)".

Dexamethasone is a corticosteroid medication which can be obtained from various suppliers such as Ark Pharm, Inc., Sigma-Aldrich, Parchem, and AvaChem Scientific.

According to some embodiments of the invention, the dexamethasone is provided at a concentration of about 0.01 nM to about 100 μM, e.g., from about 0.01 nM to about 10 μM, e.g., from 4 nM to about 10 μM, e.g., between 70-120 nM, e.g., about 100 nM (0.1 μM).

According to some embodiments of the invention, the medium includes Basic fibroblast growth factor (bFGF) or a substitute thereof, such as a small molecule or a synthetic agonist of the FGF-signaling pathway.

Basic fibroblast growth factor (also known as bFGF, FGF2 or FGF-β) is a member of the fibroblast growth factor family. BFGF [(e.g., human bFGF polypeptide GenBank Accession No. NP_001997.5 (SEQ ID NO:21); human bFGF polynucleotide GenBank Accession No. NM_002006.4 (SEQ ID NO: 22)] can be obtained from various commercial sources such as Cell Sciences®, Canton, MA, USA (e.g., Catalogue numbers CRF001A and CRF001B), Invitrogen Corporation products, Grand Island NY, USA (e.g., Catalogue numbers: PHG0261, PHG0263, PHG0266 and PHG0264), ProSpec-Tany TechnoGene Ltd. Rehovot, Israel (e.g., Catalogue number: CYT-218), and Sigma, St Louis, MO, USA (e.g., catalogue number: F0291).

According to some embodiments of the invention, the bFGF is provided at a concentration of 0.1-100 ng/ml, e.g., about 0.1-30 ng/ml, e.g., about 0.2-80 ng/ml, e.g., about 0.4-70 ng/ml. e.g., about 0.5-60 ng/ml, e.g., about 0.8-50 ng/ml, e.g., between about 1 ng/ml to about 40 ng/ml, e.g., about 1-20 ng/ml, e.g., about 2-20 ng/ml. e.g., about 3-20 ng/ml, e.g., about 4-15 ng/ml. e.g., about 10 ng/ml.

According to some embodiments of the invention, the synthetic agonist of the FGF signaling is C19-jun.

According to some embodiments of the invention, the C19-jun is provided at a concentration of about 1 ng/ml to about 50 ng/ml, e.g., in the range of 10-20 ng/ml.

According to some embodiments of the invention, the transferrin is provided at a concentration of about 0.1 ng/ml to about 55 μg/ml, e.g., from about 10 ng/ml to about 10 μg/ml, e.g., between 1-10 μg/ml, e.g., 5.5 μg/ml transferrin.

According to some embodiments of the invention, the selenium is provided at a concentration of about 0.1 ng/ml to about 6000 μg/ml. For example, in order to support fibroblast cell growth the selenium can be provided at a concentration of about 1-10 ng/ml (e.g., about 5 ng/ml of selenium to support cell growth). Alternatively, to induce adipogenesis from a fibroblast cell the selenium can be used at higher concentrations such as 200-1000 μg/ml, e.g., about 500-800 μg/ml, e.g., about 600 μg/ml to induce adipogenesis from a fibroblast cell.

The epidermal growth factor superfamily of proteins act as potent mitogenic factors that play an important role in the growth, proliferation and differentiation of numerous cell types. EGF can be purchased from Peprotech (IL, e.g., Catalogue Number AF10015).

According to some embodiments of the invention, the epidermal growth factor (EGF) is provided at a concentration of 0.1-30 ng/ml, e.g., 0.5-20 ng/ml, e.g., 1-10 ng/ml, e.g., about 5 ng/ml.

According to some embodiments of the invention, the substitute of EGF comprises an EGF-R agonist.

According to some embodiments of the invention, the EGF-R agonist comprises NSC-228155.

According to some embodiments of the invention, the NSC-228155 is provided at a concentration of about 1 ng/ml to about 100 ng/ml, e.g., about 5-50 ng/ml.

According to some embodiments of the invention, the Prostaglandin E2 (PGE2) is provided at a concentration of 0.01 nM-10 μM, e.g., from about 0.1 nM to about 1 μM, e.g., from about 10 nM to about 0.5 μM, e.g., from about 50 μM to about 0.5 μM, e.g., about 0.01 μM.

Any of the proteinaceous factors used by the method of some embodiments of the invention (e.g., the insulin, bFGF, EGF, PGE2) can be recombinantly expressed or biochemically synthesized. In addition, naturally occurring proteinaceous factors such as bFGF can be purified from biological samples (e.g., from human serum, cell cultures) using methods well known in the art. It should be noted that for the preparation of an animal contaminant-free culture medium the proteinaceous factor is preferably purified from a human source or is recombinantly expressed.

Biochemical synthesis of the proteinaceous factors of the present invention (e.g., the insulin, bFGF, EGF, PGE2) can be performed using standard solid phase techniques. These methods include exclusive solid phase synthesis, partial solid phase synthesis methods, fragment condensation and classical solution synthesis.

Recombinant expression of the proteinaceous factors of the present invention can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Methods of synthesizing the fatty acids, small molecules such as Thiazolidinediones (TZD) are known in the art.

According to some embodiments of the invention, the method is performed in-vitro.

Thus, the method of some embodiments of the invention result in the conversion of a fibroblast cell to an adipocyte cells.

Without being bound by any theory, the conversion may occur by transdifferentiation.

The adipocyte which is formed by the in-vitro method of some embodiments of the invention, by culturing the spontaneously immortalized fibroblast exhibit the characteristics of a naturally-occurring adipocyte, e.g., having a compact shape (not elongated), stains positive with Oil-O-Red, and exhibits lipid droplets with a neutral lipid stain (e.g., as shown in FIGS. 4A-D).

According to an aspect of some embodiments of the invention there is provided an adipocyte cell which is obtainable according to the method of some embodiments of the invention.

According to an aspect of some embodiments of the invention there is provided a method of generating a cultured fat on a protein matrix, comprising generating the adipocyte cell generated from the fibroblast according to the method of some embodiments of the invention, wherein the culturing is performed on a plant-derived protein matrix, thereby generating the cultured fat on the protein matrix.

According to some embodiments of the invention, the plant-derived protein matrix is from the legume (Fabaceae) family, from the cereal family or from the pseudocereal family.

According to some embodiments of the invention, the plant-derived protein matrix is from the legume, Fabaceae, family such as alfalfa, peas, beans, lentils, carob, soybeans, peanuts.

According to some embodiments of the invention, the plant-derived protein matrix is from the cereal family such as maize, rice, wheat, barley, sorghum, millet, oats, rye, tritcale, fonio.

According to some embodiments of the invention, the plant-derived protein matrix is selected the pseudocereal family including buckwheat, quinoa, or chia According to some embodiments of the invention, the plant-derived protein matrix comprises a soy protein or a pea protein.

According to some embodiments of the invention, the plant-derived protein matrix is from a soy protein or a pea protein.

According to an aspect of some embodiments of the invention there is provided a cultured fat in a plant-derived protein matrix.

According to some embodiments of the invention, the cultured fat in the plant-derived protein matrix includes about 1-1000 million cells per gram.

According to some embodiments of the invention, the cultured fat of some embodiments of the invention is obtainable by the method of some embodiments of the invention.

According to an aspect of some embodiments of the invention there is provided an in-vitro method of generating a myocyte from a fibroblast, comprising upregulating expression within a spontaneously immortalized fibroblast of a polypeptide selected from the group consisting of myoD1 and myogenin.

Methods of upregulating a level of expression and/or activity of a polypeptide are well known in the art and include recombinant DNA techniques and/or genome editing methods as is further described hereinunder.

According to some embodiments of the invention, the upregulation is of the myoD1 and myogenin polypeptides.

According to some embodiments of the invention, the chicken myoD1 polypeptide is encoded by a polynucleotide comprising the nucleic acid sequence set forth by SEQ ID NO:5.

According to some embodiments of the invention, the chicken myogenin polypeptide is encoded by a polynucleotide comprising the nucleic acid sequence set forth by SEQ ID NO:7.

According to some embodiments of the invention, the chicken myoD1 polypeptide is encoded by the nucleic acid construct set forth by SEQ ID NO: 1 or 3.

According to some embodiments of the invention, the chicken myogenin polypeptide is encoded by the nucleic acid construct set forth by SEQ ID NO: 2.

According to an aspect of some embodiments of the invention there is provided a myocyte obtainable according to the methods of some embodiments of the invention.

According to an aspect of some embodiments of the invention there is provided an in-vitro method of screening for a small molecule capable of producing a myocyte, comprising:

(a) transfecting a spontaneously immortalized fibroblast with a nucleic acid construct comprising a nucleic acid sequence encoding a reporter polypeptide under a transcriptional control of a promoter specifically active in myocytes,
(b) contacting a transfected fibroblast resultant of step (a) with at least one small molecule of a plurality of small molecules, and
(c) detecting activity of the reporter polypeptide above a pre-determined threshold in the transfected fibroblast following step (b), wherein presence of the activity above the pre-determined threshold is indicative that the at least one small molecule is capable of converting the spontaneously immortalized fibroblast into the myocyte.

According to some embodiments of the invention, the fibroblast is an avian fibroblast.

According to some embodiments of the invention, the avian is selected from the group consisting of: chicken, duck, goose, and quail.

Non-limiting examples of reporter polypeptides include, the green fluorescent protein (GFP), blue fluorescent protein (BFP), red fluorescent protein (RFP) or yellow fluorescent protein (YFP).

According to some embodiments of the invention the reporter polypeptide is the COP-GFP (e.g., as shown in FIG. 8). For example, the coding sequence of the COP-GFP can be the nucleic acid sequence set forth by SEQ ID NO: 12.

Fluorescence detection methods which can be used to detect the reporter polypeptide include for example, fluorescence activated flow cytometry (FACS), immunofluorescence confocal microscopy, fluorescence in-situ hybridization (FISH) and fluorescence resonance energy transfer (FRET).

It should be noted that the spontaneously immortalized fibroblasts can be also used in screening without genetic modification (e.g., visually for instance), for example with an antibody or a dye.

According to an aspect of some embodiments of the invention there is provided an in-vitro method of generating an edible meat, comprising culturing:

(a) a spontaneously immortalized fibroblast in a serum-free medium under conditions suitable for converting the fibroblast into an adipocyte, and/or (b) a spontaneously immortalized fibroblast in a serum-free medium under conditions suitable for converting the fibroblast into a myocyte, thereby generating the edible meat.

According to an aspect of some embodiments of the invention there is provided an in-vitro method of generating an edible meat, comprising culturing:

(a) a spontaneously immortalized fibroblast in a serum-free medium under conditions suitable for converting the fibroblast into an adipocyte, and/or (b) a spontaneously immortalized fibroblast in a serum-free medium under conditions suitable for converting the fibroblast into a myocyte, (c) an endothelial cell, thereby generating the edible meat.

According to some embodiments of the invention, the step (a) and step (b) are effected simultaneously in the same culture system.

According to some embodiments of the invention, the step (a) and step (b) are effected in two distinct (e.g., separated) culture systems.

According to some embodiments of the invention, the steps (a), (b) and (c) are effected simultaneously in the same culture system.

According to some embodiments of the invention, the serum-free medium comprises oleic acid and a PPAR-gamma agonist.

According to some embodiments of the invention, the endothelial cell is a spontaneously immortalized endothelial cell.

According to some embodiments of the invention, the endothelial cell is non-genetically modified.

According to some embodiments of the invention, the culturing is performed on a scaffold.

According to some embodiments of the invention, the cells attach to the scaffold.

Non-limiting examples of scaffolds include, but are not limited to various sponges, matrices, hydrogels or beads;

Examples of suitable sponges include, but are not limited to, polylactic acid, polyglycolic acid, or poly(lactic-co-glycolic acid) (PLGA, Sigma P2191, P2066, P1941, 430471, 764868, 790214, 900289), Variotis™ (Biometic, AU), Cellusponge™ (hydroxypropyl cellulose. Bio-Byblos Catalogue No. Z741057).

According to some embodiments of the invention, the scaffold is biodegradable.

According to some embodiments of the invention, the culturing is performed in a perfusion system.

According to some embodiments of the invention, the culturing is performed in the perfusion system of some embodiments of the invention.

According to some embodiments of the invention, the culturing is performed on an edible hollow fiber cartridge, where nutrient supply is homogenously distributed in the absence of an integrated vascular network. For example, the fibers of the cartridge are made from edible natural or synthetic polymers, such as cellulose (FiberCell, #C3008), cellulose acetate and the cells form a mass surrounding the fibers. Cellulose is FDA approved as GRAS, and used to control moisture and stabilizer shredded cheese, bread, and various sauces.

According to some embodiments of the invention, the culturing is performed on a vegetable-derived matrix.

According to some embodiments of the invention, the vegetable-derived matrix is from a cereal, gluten, or legume.

According to some embodiments of the invention, the vegetable-derived matrix is selected from the legume, Fabaceae, family, such as alfalfa, peas, beans, lentils, carob, soybeans, peanuts; or from the cereal family, such as maize, rice, wheat, barley, sorghum, millet, oats, rye, tritcale, fonio; and/or from the pseudocereal family including buckwheat, quinoa, or chia.

According to some embodiments of the invention, the legume is soy or pea.

According to some embodiments of the invention, the culturing is performed in a suspension culture devoid of substrate adherence, without any adherence of the cells to the scaffold, matrix, sponge, or any carrier such as micro-carrier beads.

According to an aspect of some embodiments of the invention there is provided an edible meat obtainable from the method of some embodiments of the invention.

According to some embodiments of the invention, the edible meat is in a form of a patty of nugget with a density in the range of about $100\times10^6$ cells/gram to about $500\times10^6$ cells/gram, e.g., about $200\times10^6$ cells/gram.

According to an aspect of some embodiments of the invention there is provided a method of generating a spontaneously immortalized fibroblast, comprising:

(a) culturing avian embryo cells in the presence of a serum-containing medium under adherent culture conditions to thereby obtain chicken embryonic fibroblasts, (b) passaging the avian embryonic fibroblasts for at least 10-12 passages in the serum-containing medium under the adherent conditions until culture collapse, wherein the culture collapse is characterized by senescence and/or death of at least 90% of avian embryonic fibroblasts, (c) isolating at least one colony which survived the culture collapse in the serum-containing medium for at least additional 20 passages, thereby generating the spontaneously immortalized fibroblast.

As used herein the phrase "culture collapse" refers to a cell culture in which the majority of the cells have undergone senescence (i.e., stop cell division) or cell apoptosis/necrosis.

According to some embodiments of the invention, the serum-containing medium is a DMEM/F12 based medium.

According to some embodiments of the invention, the serum in the medium comprises 15% FBS (fetal bovine serum).

According to some embodiments of the invention, the serum-containing medium further comprises L-Analyl-L-Glutamine.

According to some embodiments of the invention, the chicken embryo is obtained from a fertilized broiler chicken egg grown for 10-12 days.

According to an aspect of some embodiments of the invention there is provided a spontaneously immortalized chicken fibroblast obtainable by the method of some embodiments of the invention.

According to some embodiments of the invention, the spontaneously immortalized chicken fibroblast is capable of a continuous passaging for at least about 15, about 20, about 25, about 30, about 35, about 40 passages.

According to some embodiments of the invention, the spontaneously immortalized chicken fibroblast is capable of at least about 40, about 45, about 50, about 55, about 60, about 65, about 70, about 75, about 80, about 85, about 90 or more population doublings.

Upregulation of myoD1 and/or myogenin in a cell (e.g., a spontaneously immortalized fibroblast) can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like).

Following is a list of agents capable of upregulating the expression level and/or activity of myoD1 and/or myogenin.

An agent capable of upregulating expression of a myoD1 and/or myogenin may be an exogenous polynucleotide sequence designed and constructed to express at least a functional portion of the myoD1 and/or myogenin. Accordingly, the exogenous polynucleotide sequence may be a DNA or RNA sequence encoding a myoD1 and/or myogenin molecule, capable of converting the fibroblast to a myocyte cell.

To express exogenous myoD1 and/or myogenin in avian cells, a polynucleotide sequence encoding myoD1 and/or myogenin is preferably ligated into a nucleic acid construct suitable for avian cell expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize myoD1 and/or myogenin homologues which exhibit the desired activity (e.g., capable of converting the fibroblast to a myocyte cell). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:5 or 7, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, NY 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of myoD1 and/or myogenin mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a myoD1 and/or myogenin can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/$A^+$, pMT010/$A^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of myoD1 and/or myogenin since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, MD (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the myoD1 and/or myogenin protein of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the myoD1 and/or myogenin protein and the heterologous protein, the myoD1 and/or myogenin protein can be released from the chromatographic column by treatment with an appropriate enzyme or agent that disrupts the cleavage site

[e.g., see Booth et al. (1988) Immunol. Lett. 19:65-70; and Gardella et al., (1990) J. Biol. Chem. 265:15854-15859].

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Recovery of the recombinant polypeptide is effected following an appropriate time in culture. The phrase "recovering the recombinant polypeptide" refers to collecting the whole fermentation medium containing the polypeptide and need not imply additional steps of separation or purification. Not withstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

An agent capable of upregulating a myoD1 and/or myogenin in a cell may also be any compound which is capable of increasing the transcription and/or translation of an endogenous DNA or mRNA encoding the myoD1 and/or myogenin and thus increasing endogenous myoD1 and/or myogenin activity.

According to some embodiments of the invention, overexpression of the polypeptide of the invention is achieved by means of genome editing using methods well known in the art.

Genome editing is a powerful mean to impact target traits by modifications of the target plant genome sequence. Such modifications can result in new or modified alleles or regulatory elements. Thus, genome editing employs reverse genetics by artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Over expression of a polypeptide by genome editing can be achieved by: (i) replacing an endogenous sequence encoding the polypeptide of interest or a regulatory sequence under the control which it is placed, and/or (ii) inserting a new gene encoding the polypeptide of interest in a targeted region of the genome, and/or (iii) introducing point mutations which result in up-regulation of the gene encoding the polypeptide of interest (e.g., by altering the regulatory sequences such as promoter, enhancers, 5'-UTR and/or 3'-UTR, or mutations in the coding sequence).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Furthermore, "and/or" where used herein is to be taken as specific disclosure of each of the two specified features or components with or without the other. Thus, the term "and/or" as used in a phrase such as "A and/or B" herein is intended to include "A and B", "A or B", "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: 5 is expressed in a DNA sequence format (e.g., reciting T for thymine), but it can refer to either a DNA sequence that corresponds to a MyoD1 nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The system of the present embodiments can be used for other purposes as well. For example, in an embodiment of the present invention, the system can be used to generate human tissue from human cell lines with the scope of transplantations. The cells can be autologous, allologous or heterologous with respect to the patient. The procedures described above can be used in the manufacturing of partial or full organs for transplantation.

Numbered Clauses

Clause 1: Some embodiments of the present invention provide a system for growing cells comprising: a primary tissue perfusion circuit comprising: a tissue growth chamber; at least one first pump; a culture medium perfusate; an oxygenator; and a heating element; a secondary dialysis circuit comprising: at least one second pump; a dialyzer; and a dialysate; where the order of each component in each circuit of the system can be in any order.

Clause 2: Some embodiments of the present invention provide the system where the tissue growth chamber is a jacketed tissue growth chamber.

Clause 3: Some embodiments of the present invention provide the system where the tissue growth chamber is characterized by having a volume and internal dimensions that are configured and arranged to receive the growing tissue and a sufficient amount of the culture medium perfusate to continuously circulate the culture medium perfusate through the growing tissue.

Clause 4: Some embodiments of the present invention provide the system where the first, second or third pump are selected from a group consisting of peristaltic pump, positive displacement pump, impulse pump, velocity pump, gravity pump, steam pump, valveless pumps, and any combination thereof.

Clause 5: Some embodiments of the present invention provide the system where the culture medium perfusate comprises non-animal serum.

Clause 6: Some embodiments of the present invention provide the system where the culture medium perfusate comprises components selected from the group consisting of: amino acids, vitamins, trace elements, transferrin, insulin, plant-derived recombinant albumin, bacteria-derived recombinant albumin, tryptose phosphate, glutamine, glucose, fructose, sucrose, M199, DMEM/F12 medium, KO-serum, linoleic acid, oleic acid, palmate acid, lecithin, bFGF, IGF-1, Insulin, SCF, EGF, TGFβ1, IL-11, PGE, BMP4, activin A, hydrocortisone, ascorbic acid, and any combination thereof.

Clause 7: Some embodiments of the present invention provide the system where the oxygenator is a membrane oxygenator.

Clause 8: Some embodiments of the present invention provide the system where the oxygenator is adapted to provide at least one gas selected from the group consisting of oxygen ($O_2$), carbon dioxide ($CO_2$), nitrogen ($N_2$) and any combination thereof.

Clause 9: Some embodiments of the present invention provide the system where the oxygenator is adapted to maintain a ratio:percentage of each gas of $O_2$ from about 21% to about 95%, $CO_2$ from about 0% to about 10% and $N_2$ from about 0% to about 80%, inside the system.

Clause 10: Some embodiments of the present invention provide the system where the oxygenator is adapted to maintain a ratio:percentage of each gas of $O_2$ at about 80%, $CO_2$ at about 5% and $N_2$ at about 15%, inside the system.

Clause 11: Some embodiments of the present invention provide the system where the system further comprises a bubble trap.

Clause 12: Some embodiments of the present invention provide the system where the bubble trap is equally interchangeable with a debubbler or a hybrid bubble trap/debubbler.

Clause 13: Some embodiments of the present invention provide the system where the heating element is a heat exchanger.

Clause 14: Some embodiments of the present invention provide the system where the heating element is selected from the group consisting of: shell and tube heat exchanger, plate heat exchanger, plate and shell heat exchanger, adiabatic wheel heat exchanger, plate fin heat exchanger, pillow plate heat exchanger, fluid heat exchanger, waste heat recovery units, dynamic scraped surface heat exchanger, phase-change heat exchanger, direct contact heat exchanger, microchannel heat exchanger, helical-coil heat exchanger, spiral heat exchanger, and any combination thereof.

Clause 15: Some embodiments of the present invention provide the system where the oxygenator and the heating element are two distinct components.

Clause 16: Some embodiments of the present invention provide the system where the oxygenator and the heating element are one component.

Clause 17: Some embodiments of the present invention provide the system where the dialyzer comprises a membrane having a pore size selected from a range of 1 to 60 kDa.

Clause 18: Some embodiments of the present invention provide the system where the dialyzer comprises a membrane having an area selected from the range of 10 to 10000 $cm^2$.

Clause 19: Some embodiments of the present invention provide the system where the system further comprises at least one carbon filter.

Clause 20: Some embodiments of the present invention provide the system where the at least one carbon filter is adapted to clean toxins present in the dialysate.

Clause 21: Some embodiments of the present invention provide the system where the at least one ammonia filter is adapted to clean ammonia present in the dialysate.

Clause 22: Some embodiments of the present invention provide the system where toxins and ammonia are removed by the same filter.

Clause 23: Some embodiments of the present invention provide the system where the dialysate comprises glucose, amino acids, insulin, hormones such as cortisone, and growth factors in serum-free medium.

Clause 24: Some embodiments of the present invention provide the system further comprising at least one sensor selected from the group consisting of temperature sensor, pH sensor, volume sensor, flow sensor, optical sensor, glucose sensor, oxygen sensor, weight sensor, protein sensor and any combination thereof.

Clause 25: Some embodiments of the present invention provide the system further comprising at least one computer comprising at least one non-transitory computer readable medium, the non-transitory computer-readable medium storing a program that causes the computer to execute a method using a processor that executes the stored program.

Clause 26: Some embodiments of the present invention provide the system where the computer is connected to at least one remote server allowing to an external remote operator to access the computer.

Clause 27: Some embodiments of the present invention provide the system where the program allows the system to operate automatically without the need of an external operator.

Clause 28: Some embodiments of the present invention provide the system where the tissue growth chamber is adapted to grow tissue originated from cells selected from a group consisting of: primary cells, embryonic/neonatal fibroblasts cells, embryonic/neonatal endothelium cells, embryonic/neonatal muscle cells, pluripotent stem cells, embryonic stem cells, induced pluripotent stem cells (iPSC), mesenchymal stem cells, fibroblasts cells, endothelial cells, myocyte cells, satellite cells, hepatocyte cells, blood cells, neuron cells, fat cells, and any combination thereof.

Clause 29: Some embodiments of the present invention provide the system where the cells are exposed to small molecule-based reprogramming.

Clause 30: Some embodiments of the present invention provide the system where the small molecules are selected but not limited to a group consisting of: CHIR9902, SB431542, RepSox, Parnate, Forskolin, TTNPB, DZnep, VPA, CHIR99021, PD0325901, PD173074, LIF, A83-01, BIX01294, AS8351, SC1, Y27632, OAC2, SU16F, JNJ10198409, LDN193189, NSC 228155, CN 009543V, AG1478, PD 153035, 2-Me-5HT, D4476, RG108, BIO, SMI1, SMI2, 5-azacytidine, phenamil, GW7845, RG14620, or Harmine, thiazolidinediones (i.e. rosiglitazone, pioglitazone, lobeglitazone), IBMX, and any combination thereof.

Clause 31: Some embodiments of the present invention provide the system where the cells may stably comprise an inducible controlled expression transgene system or similar constructs in their genome.

Clause 32: Some embodiments of the present invention provide the system where the inducible controlled expression transgene system is a TET-on or TET-off system.

Clause 33: Some embodiments of the present invention provide the system where the induced controlled transgene expressed is MyoD.

Clause 34: Some embodiments of the present invention provide the system where the inducible controlled expression transgene system is activated or deactivated by Doxycycline or similar activators/deactivators.

Clause 35: Some embodiments of the present invention provide the system where the cells are grown in a biodegradable scaffold contained in the closed-loop perfusion circuit.

Clause 36: Some embodiments of the present invention provide the system where the cells are from a non-human animal source selected from the group consisting of: chicken, turkey, duck, quail, goose, dove, pheasant, ostrich, cow (calf), deer, goat, sheep (lamb), horse, lama, camel, rabbit, kangaroo, alligator, turtle, lobster, salmon, tuna, dolphin, whale and any combination or related species thereof.

Clause 37: Some embodiments of the present invention provide the system where the system is used to grow cells, tissue, partial or full organs from human or animal origin for transplantation purposes.

Clause 38: It is hence a scope of the present invention to provide a method for growing cells comprising: acquiring a primary tissue perfusion circuit comprising: a tissue growth chamber; at least one first pump; a culture medium perfusate; an oxygenator; and a heating element; acquiring a secondary dialysis circuit comprising: at least one second pump; a dialyzer; and a dialysate; connecting the primary tissue perfusion circuit with the secondary dialysis circuit; growing the cells in the tissue growth chamber until reaching the desired quantity.

Clause 39: Some embodiments of the present invention provide the method where the tissue growth chamber is a jacketed tissue growth chamber.

Clause 40: Some embodiments of the present invention provide the method where the tissue growth chamber is characterized by having a volume and internal dimensions that are configured and arranged to receive the growing tissue and a sufficient amount of the culture medium perfusate to continuously circulate the culture medium perfusate through the growing tissue.

Clause 41: Some embodiments of the present invention provide the method where the first, second or third pump are selected from a group consisting of peristaltic pump, positive displacement pump, impulse pump, velocity pump, gravity pump, steam pump, valveless pumps, and any combination thereof.

Clause 42: Some embodiments of the present invention provide the method where the culture medium perfusate comprises non-animal serum.

Clause 43: Some embodiments of the present invention provide the method where the culture medium perfusate comprises components selected from the group consisting of: amino acids, vitamins, trace elements, transferrin, insulin, plant-derived recombinant albumin, bacteria-derived recombinant albumin, tryptose phosphate, glutamine, glucose, fructose, sucrose, M199, DMEM/F12 medium, KO-serum, linoleic acid, oleic acid, palmate acid, lecithin, bFGF, IGF-1, Insulin, SCF, EGF, TGFβ1, IL-11, BMP4, PGE, activin A, hydrocortisone, ascorbic acid, and any combination thereof.

Clause 44: Some embodiments of the present invention provide the method where the oxygenator is a membrane oxygenator.

Clause 45: Some embodiments of the present invention provide the method where the oxygenator is adapted to provide at least one gas selected from the group consisting of oxygen ($O_2$), carbon dioxide ($CO_2$), nitrogen ($N_2$) and any combination thereof.

Clause 46: Some embodiments of the present invention provide the method where the oxygenator is adapted to maintain a ratio:percentage of each gas of $O_2$ from about 21% to about 95%, $CO_2$ from about 0% to about 10% and $N_2$ from about 0% to about 80%, inside the system.

Clause 47: Some embodiments of the present invention provide the method where the oxygenator is adapted to maintain a ratio:percentage of each gas of $O_2$ at about 80%, $CO_2$ at about 5% and $N_2$ at about 15%, inside the system.

Clause 48: Some embodiments of the present invention provide the method where the system further comprises a bubble trap.

Clause 49: Some embodiments of the present invention provide the method where the bubble trap is equally interchangeable with a debubbler or a hybrid bubble trap/debubbler.

Clause 50: Some embodiments of the present invention provide the method where the heating element is a heat exchanger.

Clause 51: Some embodiments of the present invention provide the method where the heating element is selected from the group consisting of: shell and tube heat exchanger, plate heat exchanger, plate and shell heat exchanger, adiabatic wheel heat exchanger, plate fin heat exchanger, pillow plate heat exchanger, fluid heat exchanger, waste heat recovery units, dynamic scraped surface heat exchanger, phase-change heat exchanger, direct contact heat exchanger, microchannel heat exchanger, helical-coil heat exchanger, spiral heat exchanger, and any combination thereof.

Clause 52: Some embodiments of the present invention provide the method where the oxygenator and the heating element are two distinct components.

Clause 53: Some embodiments of the present invention provide the method where the oxygenator and the heating element are one component.

Clause 54: Some embodiments of the present invention provide the method where the dialyzer comprises a membrane having a pore size selected from a range of 1 to 300 kDa.

Clause 55: Some embodiments of the present invention provide the method where the dialyzer comprises a membrane having an area selected from the range of 10 to 10000 $cm^2$.

Clause 56: Some embodiments of the present invention provide the method where the system further comprises at least one carbon filter.

Clause 57: Some embodiments of the present invention provide the method where the at least one carbon filter is adapted to clean toxins present in the dialysate.

Clause 58: Some embodiments of the present invention provide the method where the dialysate comprises glucose, amino acids, insulin, hormones such as cortisone, and growth factors in serum-free medium.

Clause 59: Some embodiments of the present invention provide the method further comprising at least one sensor selected from the group consisting of temperature sensor, pH sensor, volume sensor, flow sensor, optical sensor, glucose sensor, oxygen sensor, weight sensor, protein sensor and any combination thereof.

Clause 60: Some embodiments of the present invention provide the method further comprising at least one computer comprising at least one non-transitory computer readable medium, the non-transitory computer-readable medium storing a program that causes the computer to execute a method using a processor that executes the stored program.

Clause 61: Some embodiments of the present invention provide the method where the computer is connected to at least one remote server allowing to an external remote operator to access the computer.

Clause 62: Some embodiments of the present invention provide the method where the program allows the system to operate automatically without the need of an external operator.

Clause 63: Some embodiments of the present invention provide the method where the tissue growth chamber is adapted to grow tissue originated from cells selected from a group consisting of: primary cells, embryonic/neonatal fibroblasts cells, embryonic/neonatal endothelium cells, embryonic/neonatal muscle cells, pluripotent stem cells, embryonic stem cells, induced pluripotent stem cells (iPSC), mesenchymal stem cells, fibroblasts cells, endothelial cells, myocyte cells, satellite cells, hepatocyte cells, blood cells, neuron cells, fat cells, and any combination thereof.

Clause 64: Some embodiments of the present invention provide the method where the cells are exposed to small molecule-based reprogramming.

Clause 65: Some embodiments of the present invention provide the method where the small molecules are selected but not limited to a group consisting of: CHIR9902, SB431542, RepSox, Parnate, Forskolin, TTNPB, DZnep, VPA, CHIR99021, PD0325901, PD173074, LIF, A83-01, BIX01294, AS8351, SC1, Y27632, OAC2, SU16F, JNJ10198409, LDN193189, NSC 228155, CN 009543V, AG1478, PD 153035, 2-Me-5HT, D4476, RG108, BIO, SMI1, SMI2, 5-azacytidine and any combination thereof.

Clause 66: Some embodiments of the present invention provide the method where the cells may stably comprise an inducible controlled expression transgene system or similar constructs in their genome.

Clause 67: Some embodiments of the present invention provide the method where the inducible controlled expression transgene system is a TET-on or TET-off system.

Clause 68: Some embodiments of the present invention provide the method where the induced controlled transgene expressed is MyoD.

Clause 69: Some embodiments of the present invention provide the method where the inducible controlled expression transgene system is activated or deactivated by Doxycycline or similar activators/deactivators.

Clause 70: Some embodiments of the present invention provide the method where the cells are grown in a biodegradable scaffold contained in the closed-loop perfusion circuit.

Clause 71: Some embodiments of the present invention provide the method where the cells are from a non-human animal source selected from the group consisting of: chicken, turkey, duck, quail, goose, dove, pheasant, ostrich, cow (calf), deer, goat, sheep (lamb), horse, lama, camel, rabbit, kangaroo, alligator, turtle, lobster, salmon, tuna, dolphin, whale and any combination or related species thereof.

Clause 72: It is hence a scope of some embodiments of the present invention to grow cells wherein the cells are grown in a system as described herein.

Clause 73: Some embodiments of the present invention provide the edible in-vitro meat, where the in-vitro meat is grown in the presence of components selected from the group consisting of: amino acids, vitamins, trace elements, transferrin, insulin, plant-derived recombinant albumin, bacteria-derived recombinant albumin, tryptose phosphate, glutamine, glucose, fructose, sucrose, M199 medium, KO-serum, linoleic acid, oleic acid, palmate acid, lecithin, bFGF, IGF-1, SCF, EGF, TGFβ1, IL-11, BMP4, activin A, hydrocortisone, ascorbic acid, and any combination thereof.

Clause 74: Some embodiments of the present invention provide the edible in-vitro meat, where the in-vitro meat is grown in an environment characterized by a ratio:percentage of each gas of $O_2$ from about 21% to about 95%, $CO_2$ from about 0% to about 10% and $N_2$ from about 0% to about 80%, inside the system.

Clause 75: Some embodiments of the present invention provide the edible in-vitro meat, where the in-vitro meat is grown in an environment characterized by a ratio:percentage of each gas of $O_2$ at about 80%, $CO_2$ at about 5% and $N_2$ at about 15%, inside the system.

Clause 76: Some embodiments of the present invention provide the edible in-vitro meat, where the in-vitro meat is originated from cells selected from a group consisting of: primary cells, embryonic/neonatal fibroblasts cells, embryonic/neonatal endothelium cells, embryonic/neonatal muscle cells, pluripotent stem cells, embryonic stem cells, induced pluripotent stem cells (iPSC), mesenchymal stem cells, fibroblasts cells, endothelial cells, myocyte cells, satellite cells, hepatocyte cells, blood cells, neuron cells, fat cells, and any combination thereof.

Clause 77: Some embodiments of the present invention provide the edible in-vitro meat, where the cells are exposed to small molecule-based reprogramming.

Clause 78: Some embodiments of the present invention provide the edible in-vitro meat, where the small molecules are selected but not limited to a group consisting of: CHIR9902, SB431542, RepSox, Parnate, Forskolin, TTNPB, DZnep, VPA, CHIR99021, PD0325901, PD173074, LW, A83-01, BIX01294, AS8351, SC1, Y27632, OAC2, SU16F, JNJ10198409, LDN193189, NSC 228155, CN 009543V, AG1478, PD 153035, 2-Me-5HT, D4476, RG108, BIO, SMI1, SMI2, 5-azacytidine and any combination thereof.

Clause 79: Some embodiments of the present invention provide the edible in-vitro meat, where the cells may stably comprise an inducible controlled expression transgene system or similar constructs in their genome.

Clause 80: Some embodiments of the present invention provide the edible in-vitro meat, where the inducible controlled expression transgene system is a TET-on or TET-off system.

Clause 81: Some embodiments of the present invention provide the edible in-vitro meat, where the induced controlled transgene expressed is MyoD.

Clause 82: Some embodiments of the present invention provide the edible in-vitro meat, where the inducible controlled expression transgene system is activated or deactivated by Doxycycline or similar activators/deactivators.

Clause 83: Some embodiments of the present invention provide the edible in-vitro meat, where the cells are grown in a biodegradable scaffold.

Clause 84: Some embodiments of the present invention provide the edible in-vitro meat, where the cells are from a non-human animal source selected from the group consisting of: chicken, turkey, duck, quail, goose, dove, pheasant, ostrich, cow (calf), deer, goat, sheep (lamb), horse, lama, camel, rabbit, kangaroo, alligator, turtle, lobster, salmon, tuna, dolphin, whale and any combination or related species thereof.

Clause 85: Some embodiments of the present invention provide the edible in-vitro meat, where the cells are grown in a non-animal serum medium.

Clause 86: Some embodiments of the present invention provide the edible in-vitro meat, where the cells are grown in a medium which comprises glucose, amino acids, insulin, hormones such as cortisone, and growth factors in serum-free medium.

Clause 87: It is hence a scope of the present invention to provide a transplantable in-vitro tissue wherein the in-vitro tissue is manufactured in a system as described herein.

Clause 88: Some embodiments of the present invention provide the transplantable in-vitro tissue where the in-vitro tissue is grown in the presence of components selected from the group consisting of: amino acids, vitamins, trace elements, transferrin, insulin, plant-derived recombinant albumin, bacteria-derived recombinant albumin, tryptose phosphate, glutamine, glucose, fructose, sucrose, M199 medium, KO-serum, linoleic acid, oleic acid, palmate acid, lecithin, bFGF, IGF-1, SCF, EGF, TGFβ1, IL-11, BMP4, activin A, hydrocortisone, ascorbic acid, and any combination thereof.

Clause 89: Some embodiments of the present invention provide the transplantable in-vitro tissue where the in-vitro meat is grown in an environment characterized by a ratio:percentage of each gas of $O_2$ from about 21% to about 95%, $CO_2$ from about 0% to about 10% and $N_2$ from about 0% to about 80%, inside the system.

Clause 90: Some embodiments of the present invention provide the transplantable in-vitro tissue where the in-vitro meat is grown in an environment characterized by a ratio:percentage of each gas of $O_2$ at about 80%, $CO_2$ at about 5% and $N_2$ at about 15%, inside the system.

Clause 91: Some embodiments of the present invention provide the transplantable in-vitro tissue where the tissue is originated from cells selected from a group consisting of: primary cells, embryonic/neonatal fibroblasts cells, embryonic/neonatal endothelium cells, embryonic/neonatal muscle cells, pluripotent stem cells, embryonic stem cells, induced pluripotent stem cells (iPSC), mesenchymal stem cells, fibroblasts cells, endothelial cells, myocyte cells, satellite cells, hepatocyte cells, blood cells, neuron cells, fat cells, and any combination thereof.

Clause 92: Some embodiments of the present invention provide the transplantable in-vitro tissue where the cells are exposed to small molecule-based reprogramming.

Clause 93: Some embodiments of the present invention provide the transplantable in-vitro tissue where the small molecules are selected but not limited to a group consisting of: CHIR9902, SB431542, RepSox, Parnate, Forskolin, TTNPB, DZnep, VPA, CHIR99021, PD0325901, PD173074, LIF, A83-01, BIX01294, AS8351, SC1, Y27632, OAC2, SU16F, JNJ10198409, LDN193189, NSC 228155, CN 009543V, AG1478, PD 153035, 2-Me-5HT, D4476, RG108, BIO, SMI1, SMI2, 5-azacytidine and any combination thereof.

Clause 94: Some embodiments of the present invention provide the transplantable in-vitro tissue where the cells may stably comprise an inducible controlled expression transgene system or similar constructs in their genome.

Clause 95: Some embodiments of the present invention provide the transplantable in-vitro tissue where the inducible controlled expression transgene system is a TET-on or TET-off system.

Clause 96: Some embodiments of the present invention provide the transplantable in-vitro tissue where the induced controlled transgene expressed is MyoD.

Clause 97: Some embodiments of the present invention provide the transplantable in-vitro tissue where the inducible controlled expression transgene system is activated or deactivated by Doxycycline or similar activators/deactivators.

Clause 98: Some embodiments of the present invention provide the transplantable in-vitro tissue where the cells are grown in a biodegradable scaffold.

Clause 99: Some embodiments of the present invention provide the transplantable in-vitro tissue where the cells are from a non-human animal source selected from the group consisting of: chicken, turkey, duck, quail, goose, dove, pheasant, ostrich, cow (calf), deer, goat, sheep (lamb), horse, lama, camel, rabbit, kangaroo, alligator, turtle, lobster, salmon, tuna, dolphin, whale and any combination or related species thereof.

Clause 100: Some embodiments of the present invention provide the transplantable in-vitro tissue where the cells are from a human source.

Clause 101: Some embodiments of the present invention provide the transplantable in-vitro tissue where the cells are grown in a non-animal serum medium.

Clause 102: Some embodiments of the present invention provide the transplantable in-vitro tissue where the cells are grown in a medium which comprises glucose, amino acids, insulin, hormones such as cortisone, and growth factors in serum-free medium.

Various embodiments and aspects of the present invention as delineated hereinabove and as claimed in the claims section below find experimental, and/or calculated support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Closed-Loop Perfusion Circuit for Growth of Chicken Liver

Liver is a highly nutritious, high value product, with relatively soft consistency due to the low abundance of fibrillar matrix and hive-like structure. A genetic modification is used to induce the proliferation of chicken hepatocytes and endothelial cells, allowing to optimize the close-loop perfusion circuit for high-density tissue growth. Closed-loop perfusion includes, as mentioned above, a dialysis unit permitting physiological addition of nutrients and removal of toxins, instead of complete media replacement.

1.1 Closed-Loop Perfusion Circuit

The perfusion system is composed of a primary tissue perfusion circuit and a secondary dialysis circuit for nutrient and toxin exchange (10). The primary circuit includes culture medium perfusate that is recirculated using a peristaltic pump through a jacketed tissue growth chamber, a membrane oxygenator, a heat exchanger, and a bubble trap. The oxygenator is gassed with a mixture of 80% $O_2$/5% $CO_2$/15% $N_2$ maintaining constant pH.

A fraction of the perfusate is diverted to secondary circuit through a Spectrum Labs hollow fiber dialyzer (Rancho Dominguez, CA) with a 790 $cm^2$ membrane area and a 30 kDa molecular weight cutoff at a rate of 3 mL/min/gram tissue. The secondary circuit dialyzed the perfusate by counter-current exposure to protein-free dialysate, recirculated through a carbon filter using a third peristaltic pump. Temperature within the system is maintained at 37° C.

The main advantage of dialysis is that albumin, with a molecular weight of 66.5 kDa, is retained in the main perfusion circuit. Albumin has a half-life of 20 days and is a carrier protein of growth factors, peptides (e.g. insulin), and fatty acids. Albumin and growth factors are the main cost driver of culture medium.

1.2 Model Cells and Tissue Growth

Recently, it has been demonstrated that expression of E6/E7 proteins permitted the rapid expiation of functional human hepatocytes, liver endothelial and stellate cells under OSM-stimulation (1). Stably infected E6/E7LOW hepatocytes with GFP, endothelial cells with mCherry, and stellate cells with CFP using lentivirus reporters were used for optimization of the device. These fluorescent markers helped assess tissue organization and proliferation rates before beginning the actual production of the chicken liver. Seeded on a soft hydrogel matrix, this cell mixture rapidly forms a proliferating liver organoid (11).

Cells are mixed in ratio of 1:1:0.1 for hepatocytes, endothelial cells, and stellate cells, respectively, spun down and re-suspended in 0.1 ml hydrogel matrix composed of animal-free synthetic polypeptides with pore size of 50 to 200 nm (Sigma, A6982). Hydrogel-cell suspension are injected into a biodegradable polymer scaffold with pore size of 50 to 1000 μm, and placed in the jacked tissue growth chamber. While the hydrogel polypeptides will be replaced with native extracellular matrix within 5-7 days, the polymer scaffold will support the growing tissue for 14-28 days until it reaches significant mass and the cells cannot be washed away.

1.3 Growth Optimization

To optimize tissue growth and minimization of nutrient addition, tissue uptake rates of glucose, glutamine, fatty acids and albumin were carefully analyzed by present inventor aiming to keep consternations constant. Perfusate and dialysate were automatically sampled using microfluidic switchboard every 4 hours to monitor glucose, lactate, glutamine, fatty acid and albumin content (12). Oxygen content was measured dynamically using optical sensors (13).

Data was used to determine rate and volume of medium supplementation as a function of tissue growth rate.

Tissue morphology and growth rates were quantified daily using confocal microscopy. Human albumin and bile acid production were measured in the perfusate every 24 hours, marking liver-specific function. Finally, the absence of necrosis or apoptosis was assessed using H&E and TUNEL staining following 7, 14 and 28 days of growth.

Example 2

Development of Small Molecule-Based Expansion of Serum-Free Cultures of Chicken Hepatocytes, Endothelial Cells and Fibroblasts Chemical compounds offer an attractive alternative to growth factors that are generally used to stimulate serum-free cell growth. Small molecules are far less expensive than recombinant growth factors, have lower lot-to-lot variability, are non-immunogenic and are much more stable.

2.1 Developing and Optimizing Minimal Growth Medium

Chicken fibroblasts were purchased from Charles River Laboratories (Wilmington, MA) and expanded in serum-free medium composed of M199 supplemented with 0.5 mg/mL plant-derived albumin (Cellastim™), 0.6 μM linoleic and oleic acid, 0.6 μg/mL soy lecithin, 7.5 mM L-Alanyl-L-Glutamine, 0.1 μM dexamethasone, 50 μg/mL ascorbic acid, and 0.5 U/mL insulin (Eli Lilly). This minimal medium was generally further supplemented with 5 ng/mL bFGF, 5 ng/mL EGF, and 30 pg/mL TGFβ1 to support 4-fold faster proliferation of fibroblasts, at considerable expense. Cells were expanded in complete medium up to PD (population doubling) 15 to generate frozen stocks, and were used between PD 15 and 25. To study whether all growth factors were essential for chicken fibroblast expansion, the present inventor assessed proliferation rates as a function of growth factor concentration aiming to find a minimal combination.

Chicken embryonic endothelial cells were isolated from fertilized eggs or purchased from Charles River Laboratories (Wilmington, MA). Cells were expanded in serum-free endothelium medium composed of RPMI1640 supplemented with 3.75 mg/mL plant-derived albumin (Cellastim™), 0.6 μM linoleic and oleic acid, 0.6 μg/mL soy lecithin, 7.5 mM L-Alanyl-L-Glutamine, 0.1 μM dexamethasone, 50 μg/mL ascorbic acid, and 0.5 U/mL insulin (Eli Lilly). This minimal medium was further supplemented with 5 ng/mL bFGF, 5 ng/mL EGF, and 10 ng/mL VEGF. Cells were expanded in complete medium up to PD 5 to generate frozen stocks, and are used between PD 5 and 10. To study whether all growth factors were essential for chicken endothelial cell expansion, the present inventor assessed proliferation rates as a function of growth factor concentration aiming to find a minimal combination.

Chicken embryonic muscle cells were isolated from fertilized eggs or purchased from Charles River Laboratories (Wilmington, MA). Cells were expanded in serum-free medium composed of M199 supplemented with 0.5 mg/mL plant-derived albumin (Cellastim™), 0.6 μM linoleic and oleic acid, 0.6 μg/mL soy lecithin, 7.5 mM L-Alanyl-L-Glutamine, 0.1 μM dexamethasone, 50 μg/mL ascorbic acid, and 0.5 U/mL insulin (Eli Lilly). This minimal medium was generally further supplemented with 5 ng/mL bFGF, 5 ng/mL EGF, and 30 pg/mL IGF-1. Cells were expanded in complete medium up to PD 15 to generate frozen stocks, and were used between PD 5 and 10. To study whether all growth factors were essential for chicken myocytes expansion, the present inventor assessed proliferation rates as a function of growth factor concentration aiming to find a minimal combination.

Chicken hepatocytes were purchased from Charles River Laboratories (Wilmington, MA) and seeded in serum-free formulation composed of Williams E medium supplemented with 3.75 mg/mL plant-derived albumin (Cellastim™), 0.2 μM linoleic and oleic acids, 2 mM L-Alanyl-L-Glutamine, 0.1 μM dexamethasone, 5 μg/mL transferrin, and 0.5 U/mL insulin (Eli Lilly). It has been shown that this serum-free medium supports the robust expansion of genetically modified human hepatocytes (1). Cells were exposed to FPH1 (BRD-6125), FPH2 (BRD-9424), and FH1 (BRD-K4477) small molecules identified to enhance proliferation of unmodified human hepatocytes (7). The present inventor expected that limited proliferation would be achieved due to evolutionary conservation of liver regeneration signaling pathways. High throughput screen of chicken hepatocytes without small-molecule driven expansion is still possible, but it is simply more expensive.

2.2 Identification of Small Molecule Growth Enhancers in a High Throughput Screen High content screening of small molecules is carried out at the Broad Institute of MIT and Harvard or an equivalent robotic screening facility. A separate screening for chicken fibroblasts, endothelial cells, myocytes and hepatocytes is carried out. Cells are seeded in 384-well screening plates (Corning) at a density of 10,000 cells/cm$^2$ in the appropriate minimal growth medium without supplements. Plates are incubated at 37° C. and 5% $CO_2$ and medium is replaced daily. A library of 12,480 compounds is added at concentration of 15 μM and incubated for 48 hours. The present inventor carries out a standard MTT analysis; acquired phase images of the treated cells, and Hoechst analysis for total DNA. To identify functional proliferation hits, the positive MTT and DNA increase are integrated based on p-value.

Chemicals producing functional proliferation hits were combined in a smaller screening profile aiming to identify minimal functional combinations that produce the greatest fold increase in proliferation. Based on earlier reports (7), the present inventor expected 2 to 3 small molecules to be identified in each screen. For example, NSC-228155 was recently shown to be an EGF-R agonist (16). Once small molecules cocktails were identified, the present inventor attempted to add back growth factors at lower concentrations to see if greater proliferation enhancement can be achieved in a cost-efficient manner.

Example 3

Development of Small-Molecule Based Differentiation of Chicken Muscle Cells

Myocyte expansion is usually limited to 15 population doublings, producing 16-gram tissue from each isolate. However, myocytes can be differentiated from pluripotent stem cells in a multistep process mimicking myogenesis (17). Alternatively, fibroblasts can be converted to myocytes using MyoD expression (18) or a cocktail of small molecules (8).

Pluripotent stem cells double every 44±13 hours and their serum free medium costs about $540/liter. In contrast, fibroblasts double every 21±3 hours and their serum free medium costs about $272/liter. This means that using current techniques, pluripotent stem cells will produce 1 kg tissue after 39 days, at $100,000/kg, while fibroblasts will do so after 18 days, at $50,000/kg. Therefore, the present inventor' approach primarily focused on genetic and chemical differentiation of fibroblasts to myocytes, with pluripotent stem cells studied to mitigate risk.

3.1 Generation of Tetracycline-Dependent MyoD Expressing Chicken Fibroblasts

Doxycycline (Dox) is an analog of tetracycline that can be used to rapidly activate gene expression by binding a reverse tetracycline-controlled advanced transactivator (rtTA2$^s$-M2) that acts on a tetracycline responsive element (TRE). Dox shows no apparent toxicity, is inexpensive and can be readily washed out of the cells following activation. The system has been shown to reliably work on chicken embryos (19).

The present inventor has generated a stable line of chicken fibroblasts expressing Dox-inducible chicken MyoD, by introducing pCAGGS-rtTA2$^s$-M2 and pTRE-MyoD plasmids under puromycin selection. Chicken fibroblasts were exposed to 0.5 ng/μl Dox for 48 hour and MyoD expression was evaluated by qRT-PCR. Conversion to myocytes was evaluated 7 and 12 days after Dox induction by staining for myosin heavy chain (MyHC) and titin (18). Dox-induced muscle cells served as positive control and a genetically engineered (GE) alternative to small molecule-induced conversion of fibroblasts to myocytes.

3.2 Identification of Small-Molecule Cocktail for Conversion of Myocytes

Recently mouse fibroblasts were converted to cardiomyocytes by a two-step combination of small molecules promoting reprogramming; including CHIR9902, RepSox, Forskolin, and VPA followed by 2i (CHIR99021 and PD0325901) conditions promoting myocardium development; including CHIR99021, PD0325901, and LIF (9). Human fibroblasts were similarly converted using a combination of reprogramming and differentiation-inducing factors CHIR99021, A83-01, BIX01294, AS8351, SC1, Y27632, OAC2, SU16F and JNJ10198409 (8). Conversion was slow, taking 20 to 30 days and producing about 6% cardiomyocytes.

In a screen of zebrafish, mouse, and human cells, Xu (Xu et al. Cell 155, 909-921, 2013) and colleagues identified 6 small molecules that expanded muscle progenitors, including the adenylyl cyclase activator, forskolin. A combination of bFGF, forskolin, and the GSK3b inhibitor BIO induced skeletal muscle differentiation of human induced pluripotent stem cells (21). In a different screen, a group identified SMI1 and SMI2 to robustly induce skeletal muscle differentiation from pluripotent stem cells, while others showed 5-azacytidine can similarly promote myogenesis (22). These results suggest that a two-step procedure to trans-differentiate skeletal muscle using a reprogramming cocktail (6), followed factors that promote skeletal muscle myogenesis in pluripotent stem cells, can produce promising results.

The present inventor' approach was to stably transfect chicken fibroblasts with EGFP reporter for MyHC for high throughput screening (8). Cells were exposed to varying cocktails of reprogramming and myogenic factors discussed above, as well as those identified in example 2.2. Cells were evaluated based on EGFP fluorescence and myofiber morphology after 20 days of induction. To identify functional hits, the present inventor integrated positive MyHC and morphology hits based on p-value.

3.3. Developing Direct Differentiation of Chicken Pluripotent Stem Cells

The avian embryo spends only 20 hours in utero as it descends down the oviduct. By the time the egg is laid, the epiblast is a single layer comprised of 20,000-50,000 cells. Chicken embryonic stem cells are derived from this blastodisc and can be perpetuated in culture, producing all somatic lineages but not the germline (3). Like mouse embryonic stem cells, they require LIF to remain undifferentiated. Culture medium includes bFGF, IGF-1, SCF, and IL-11, in addition to LIF (23).

Recently, serum-free protocols for differentiation of muscle fibers were published for mouse and human pluripotent stem cells (17). Mouse stem cells were induced toward a mesoderm phenotype in N2B27 medium containing 10 ng/ml BMP4 for 2 days, DMEM medium containing 15% knockout serum, 0.5% DMSO, 0.1 μM LDN193189, and 1 μM CHIR99021 for 4 days. Then mesodermal cells differentiated to skeletal muscle in DMEM medium containing 15% knockout serum, 10 ng/ml HGF, 2 ng/ml IGF-1, 20 ng/ml bFGF, and 0.1 μM LDN193189 for 8 days. The protocol is robust, generating 30-60% muscle cells in 14 days.

As noted above, other groups identified additional small molecules that drive the differentiation of pluripotent stem cells toward skeletal muscle cells. These include the combination of bFGF, forskolin and BIO (21), SMI1 and SMI2 (24), and finally 5-azacytidine (22).

The present inventor' approach was to translate existing serum-free mouse protocols to chicken embryonic stem cells taking into account differences in avian development pathways (25). Small molecules identified in previous studies were used to augment differentiation and increase muscle fiber density.

Example 4

Establishing Closed-Loop Perfusion Circuit for Growth and Differentiation of Chicken Muscle Muscle tissue is highly packed myofiber cluster nourished by endothelial capillaries. Fibrillar collagen, secreted by the mesenchyme plays a significant role in tissue consistency. The present inventor's approach was to grow a high density of chicken fibroblasts and endothelial cells in a biodegradable scaffold contained in a closed-loop perfusion circuit optimized in example 1. Shear forces helped align collagen fibers deposited by the growing fibroblasts. Once sufficient mass was reached, small molecules were introduced in differentiation medium converting fibroblasts to skeletal muscle cells (example 3) and allowing the myofiber to align along to shear-aligned fibers.

Closed-loop perfusion included a dialysis unit permitting physiological addition of nutrients and removal of toxins, instead of complete media replacement. The main advantage of dialysis was that albumin, with a molecular weight of 66.5 kDa, was retained in the main perfusion circuit. Albumin has a half-life of 20 days and is a carrier protein of growth factors and fatty acids. Albumin and growth factors are the main cost drivers of culture medium.

4.1 Closed-Loop Perfusion Circuit

The perfusion system that was optimized in example 1.1 was used here. Briefly, the primary circuit included culture medium perfusate that was recirculated using a peristaltic pump through a jacketed tissue growth chamber, a membrane oxygenator (80% 02, 5% $CO_2$, and 15% $N_2$), a heat exchanger (37° C.), and a bubble trap. A fraction of the perfusate was diverted to a hollow fiber dialyzer with a 2200 $cm^2$ membrane area and a 30 kDa molecular weight cutoff at a rate of 3 mL/min/gram tissue. The secondary circuit dialyzed the perfusate by counter-current exposure to protein-free dialysate and recirculated through a carbon filter using a second peristaltic pump.

4.2 Model Cells and Tissue Growth

Cell seeding that was optimized in example 1.2 was used here. The experiment used a mixture of Dox-MyoD chicken fibroblasts developed in example 3.1 and endothelial cells at 10:1 ratio. Briefly, cells were suspended in 0.1 ml hydrogel matrix composed of animal-free synthetic polypeptides with pore size of 50 to 200 nm (Beaver Labs). Hydrogel-cell suspension was injected into a biodegradable polymer scaffold with pore size of 50 to 1000 μm, and placed in the jacked tissue growth chamber. While the hydrogel polypeptides were replaced with native extracellular matrix within 5-7 days, the polymer scaffold supported the growing tissue for 14 days until it reached significant mass and the cells could not be washed away. Scaffold was removed at 5 and 10 days fixed and sectioned for analysis. The present inventor stained for collagen type-I deposition and alignment, and analyzed connective tissue density and health using H&E staining.

The present inventor introduced 0.5 ng/μl Dox for 4 days, inducing conversion of fibroblasts to muscle cells. Then Dox was washed out for 4 days, replaced with IFG-1 to promote cell fusion to muscle fibers. Tissue was removed at day 14 and 18 fixed and sections for analysis. The present inventor stained for MyHC, desmin and titin, and analyzed the resulting muscle tissue density and health using H&E staining. Comparing desmin and MyHC positive cells, as well as qRT-PCR assessed the degree of muscle formation.

4.3 Growth Optimization

Tissue growth was optimized to adjust the feeding parameters to the growing cells and the differentiation method used. Tissue uptake rates of glucose, glutamine, fatty acids and albumin were analyzed aiming to keep consternations constant. Perfusate and dialysate were automatically sampled using microfluidic switchboard every 4 hours to monitor glucose, lactate, glutamine, fatty acid and albumin content (12). Oxygen content was measured dynamically using optical sensors (13). Data was used to determine rate and volume of medium supplementation as a function of tissue growth rate.

Tissue growth rates were quantified using AlamarBlue® (Thermo Fisher Sci.) a non-toxic, secreted, cell viability indicator. Finally, the absence of necrosis or apoptosis was assessed using H&E and TUNEL staining following 6, 12 and 18 days of growth.

4.4 Cell-Specific Approach

Some embodiments of the present intention are to reach 150 grams of chicken muscle tissue in each circuit, equivalent to a large drumstick or chicken breast. This represents a mass of $3\times10^{10}$ cells achieved in about 18 population doublings. For fibroblasts, it represents 16 to 18 days of growth. MyoD-induced conversion is rapid (18) allowing to grow fibroblasts for 10 days and differentiate them for 8 days in culture. In contrast, small molecule based reprogramming approaches (8) (9) are reported to take between 24 to 30 days, at least for cardiomyocytes. While the developmentally simpler skeletal muscle differentiation will undoubtedly be shorter, insights from example 3.2 played a critical role in deciding the initial seeding densities and the timing of conversion.

Importantly, this cell density represents 33 to 35 days of growth for embryonic stem cells. The current serum-free differentiation protocol (17) requires only 14 days of differentiation. Therefore, chicken embryonic stem cells can be seeded at higher densities and grown in pluripotency medium for 19 days. The main challenge for embryonic stem cells growth is that the tissue cannot be endothelialized as endothelial cells would promote differentiation. This means that individual embryonic stem cell clusters must be smaller than 0.5 mm in diameter, or suffer necrosis at the core. One solution was to seed embryonic stem cells on biodegradable alginate microparticles (Quad Technologies) allowing the suspension to grow separately within the tissue growth chamber. The present inventor has previously been successful in growing human embryonic stem cells in a similar high-density suspension cultures (26).

Example 5

Chicken-Based Laboratory Grown Meat: Generation of Spontaneously Immortalized Chicken Fibroblast Cell Line The following Example illustrates non-limiting cells, which can be used for culturing meat in-vitro.

Animal-Free, High-Density Expansion of Chicken Cells—

Various independent cell sources can be used for growing meat in-vitro.

(1) Chicken embryonic fibroblasts were isolated and expanded until spontaneous immortalization occurred.

(2) An immortal chicken iPSC line is generated using non-integrating vectors or small molecules from which fibroblasts can be obtained by routine differentiation.

(3) Several established ATCC cell lines can be used. These include DF1 (chicken), QM7 (quail), and DE (duck).

(4) Integrating vectors are used to establish chicken iPSC lines as described in literature (Intarapat & Stern 2013).

Derivation of a Spontaneously Immortalized Line of Chicken Embryonic Fibroblasts

Experimental Methods

Fertilized broiler chicken eggs were grown at 38.5° C. for 10-12 days in a humidified incubator. Eggs were opened between day 10 to 12 and embryos removed. Heads, limbs and internal organs were removed, and cells were mechanically extracted and plated on tissue culture treated plastic in DMEM/F12 medium supplemented with 15% FBS (fetal bovine serum), and 2 mM of L-Analyl-L-Glutamine.

Experimental Results

Figure 2A:
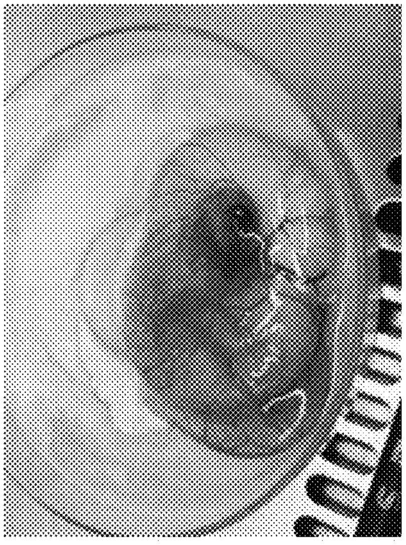
FIGS. 2A-E demonstrate the derivation of a spontaneously immortalized line of chicken embryonic fibroblasts.
Figure 2B:
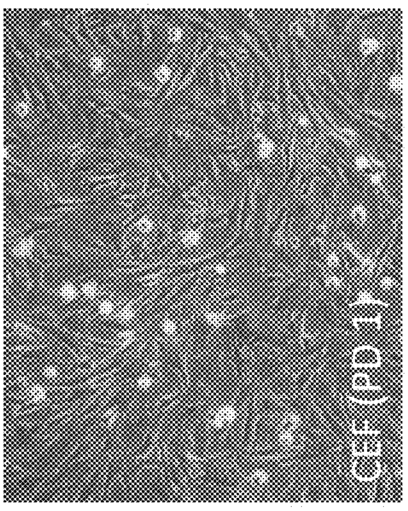
Figure 2C:
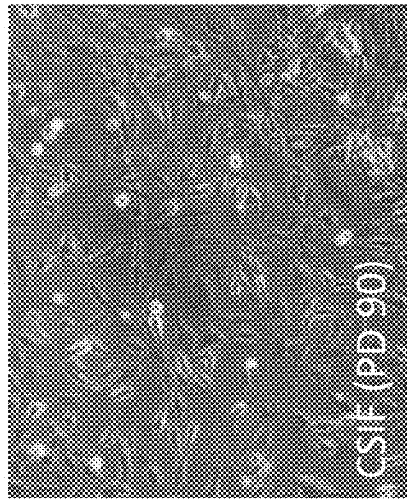

Under these conditions, in the absence of any other growth factors, fibroblasts outgrow the culture resulting in homogenous populations of primary chicken embryonic fibroblasts (CEFs) (FIGS. 2A-B). Roughly $2\times10^7$ cells were isolated per embryo, with multiple populations cultured in parallel. Initial CEF morphology was elongated, becoming more compact with increasing passage number (FIG. 2B and data not shown). Most CEF cultures became senescent by population doubling (PD) 30-40 (data not shown); with 2-3 colonies surviving the crisis becoming spontaneously immortalized chicken fibroblasts (CSIFs; FIG. 2C). CSIF show fibroblast morphology and exhibit a doubling time of 18±2 hours by PD 90 (FIG. 2E).

Example 6

Chicken-Based Laboratory Grown Meat: Identification of a Serum-Free Medium for Propagating Spontaneously Immortalized Chicken Fibroblast Cell Line Development of Serum-Free Medium for CSIF Propagation—

Figure 2D:
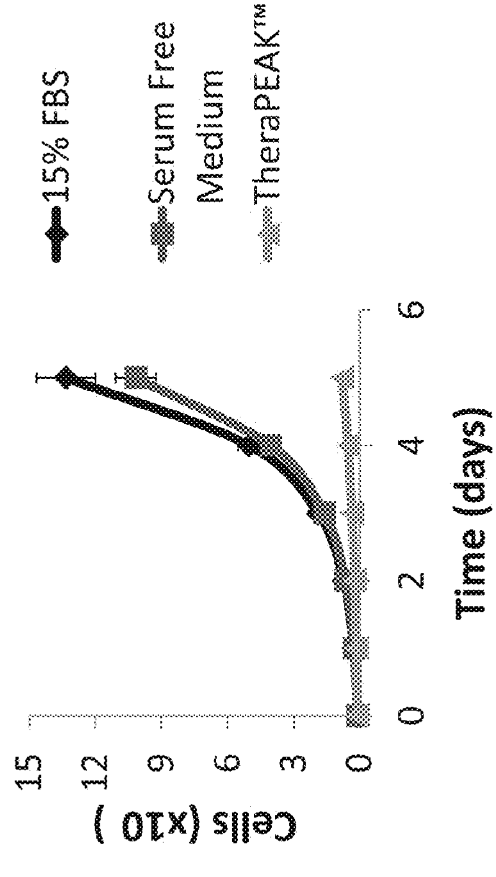
Figure 2E:
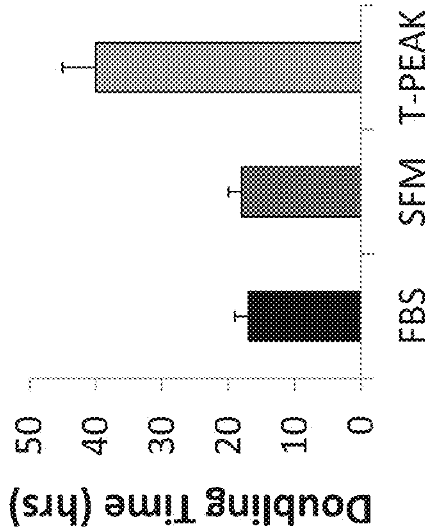

The CSIFs readily grow on tissue culture plastic in DMEM/F12 medium supplemented with 15% FBS, and 2 mM of L-Analyl-L-Glutamine (FIG. 2D). There are several serum-free medium formulations for the growth of human and mouse fibroblasts, including PCS-201-040 (ATCC) and TheraPEAK (Lonza), both failed to support the proliferation of primary CEF or the novel CSIF line obtained by the present inventor (FIGS. 2D, 2E and data not shown).

Figure 3A:
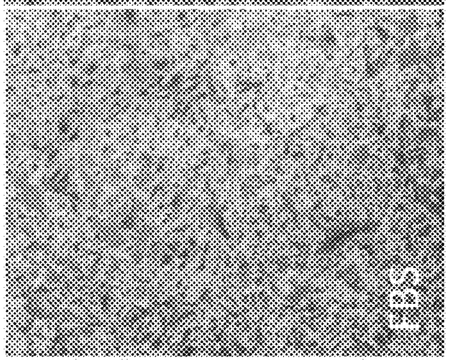
FIGS. 3A-F depict the development and identification of serum-free medium for CSIF propagation. Shown are sulforhodamine B stain (FIGS. 3A-E) and protein content quantification (FIG. 3F) following 72 hours of culture with 15% serum ("FBS"), minimal serum-free medium (MIN) alone (FIG. 3B) or with 10 ng/ml basic Fibroblast Growth Factor (bFGF, FIG. 3C), 5 ng/ml Epidermal Growth Factor (EGF, FIG. 3D), 0.01 μM Prostaglandin E2 (PGE2, FIG. 3E), or 10 ng/ml Growth Hormone. Serum-free medium (SFM) contained MIN medium supplemented with bFGF (10 ng/ml), EGF (5 ng/ml), and PGE2 (0.01 M). "MIN" medium included: DMEM/F12, 0.1 μM dexamethasone, insulin, transferrin, and selenium (ITS), 12 μM linoleic and oleic acids, and L-Analyl-L-Glutamine.(GlutaMAX); Note that the cells cultured in the SFM exhibit a similar cell mass (as determined by protein content) as the cells cultured in a medium supplemented with 15% FBS.
Figure 3B:
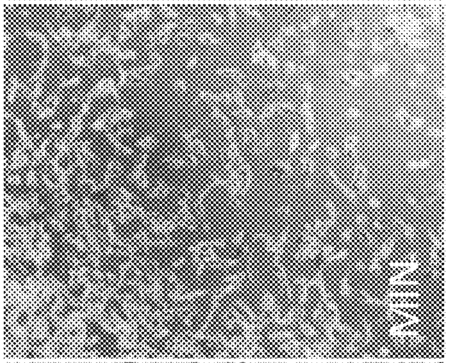
Figure 3C:
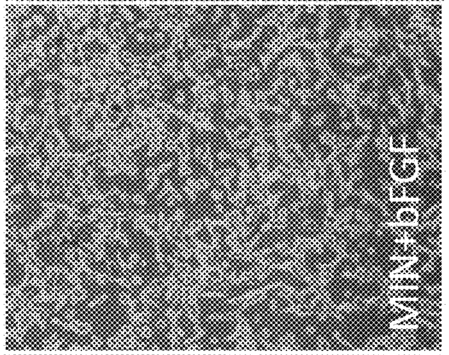
Figure 3D:
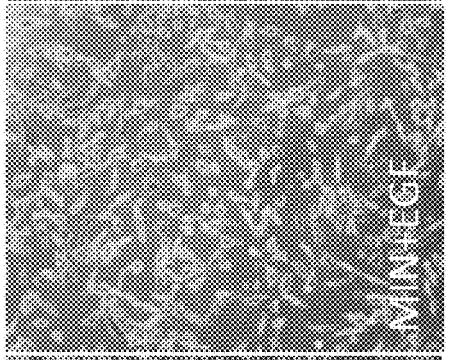
Figure 3E:
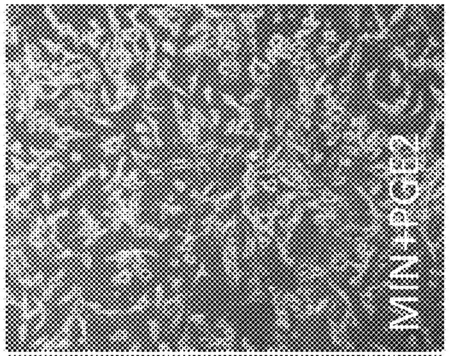
Figure 3F:
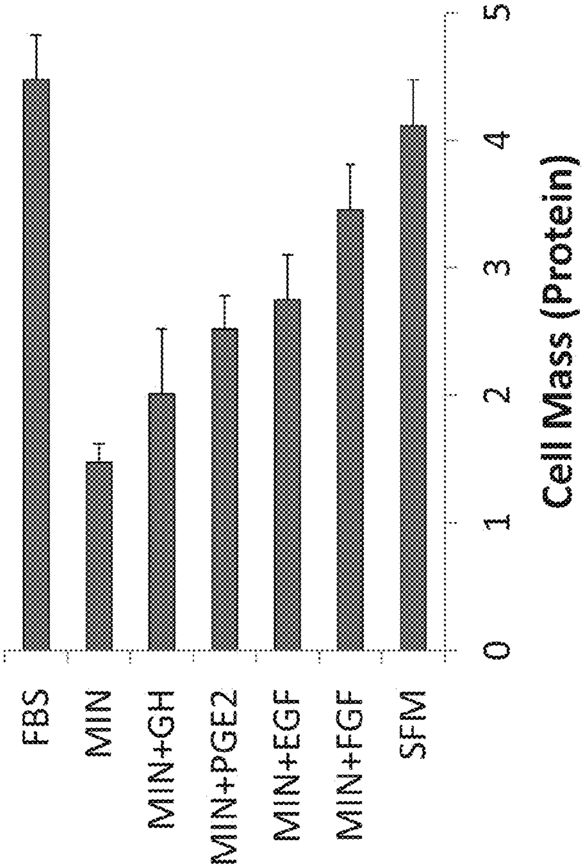

To develop a serum-free medium that supports the culture of CEF and CS IF, the present inventor formulated a minimal medium composed of DMEM/F12 supplemented with 0.1 μM dexamethasone, 10 μg/ml insulin, 5.5 μg/ml transferrin, and 5 ng/ml selenium (ITS), 12 μM linoleic and 12 μM oleic acids, and 2 mM of L-Analyl-L-Glutamine. Cells were plated in FBS containing medium, and transferred to minimal medium after overnight attachment. Basal medium was supplemented with growth factors and hormones showing that while heparin and T3 had little effect of CSIF growth (data not shown), the addition of basic Fibroblast Growth Factor (bFGF, 10 ng/ml) was essential (FIGS. 3C and 3F), showing 20±2 hours doubling time (data not shown). In addition, Epidermal Growth Factor (EGF, 5 ng/ml), Prostaglandin E2 (PGE2, 0.01 μM) and Growth Hormone (GH, 10 ng/ml) supported the proliferation of CEF and CSIF (FIGS. 3D, 3E, 3F and data not shown).

The optimal growth medium tested by the present inventor was composed of DMEM/F12 supplemented with dexamethasone (0.1 μM), 1×ITS+3 (Sigma, 12771), bFGF (10 ng/ml), EGF (5 ng/ml), and PGE2 (0.01 μM) resulting in similar growth rates to a culture medium containing 15% FBS.

Under some conditions, insulin could be replaced with IGF-1 (5 ng/ml), or the stabilized Long R3 IGF-1 [Sigma (5 ng/ml)]. EGF can be replaced with the EGF-R agonist [NSC-228155 (Sakanyan et al. Sci. Reports. 2014] at a concentration of 5-50 ng/ml. FGF can similarly be replaced with a small molecule or synthetic agonist such as C19-jun (Ballinger et al. Nature. Biotech. 1999) at a concentration of 10-20 ng/ml.

A screen for small molecules is carried out essentially as described in Example 2 above. The first small molecule screen attempts to identify molecules that can replace growth factors and hormones in the culture medium (e.g. insulin, FGF, EGF, TGFβ). Thus, a sequential removal of one growth factor or hormone at a time is performed, aiming to reach the same growth rate with a small molecule replacement.

The co-culture of endothelial cells with the fibroblasts allows the present inventor to remove some growth factors that are naturally produced by the endothelium.

Additionally or alternatively, cells are engineered to specifically produce these growth factors, thereby reducing overall cost.

It should be noted that the lack of attachment factors (e.g. vitronectin, fibronectin) in serum-free medium makes it difficult to serially passage CEF or CSIF. Since animal or human derived extracellular matrix proteins must be avoided other natural, recombinant proteins and/or synthetic polymers such as Poly-D-Lysine can be used to propagate cells in the absence of serum.

Example 7

Chicken-Based Laboratory Grown Meat: Conversion of a Spontaneously Immortalized Chicken Fibroblast Cell Line into Adipocute in a Serum-Free Medium Conversion of CSIF to Adipocytes in Serum Free Medium—

In mammalian species, preadipocytes can be readily differentiated into adipocytes using 3-isobutyl-1-methylxanthine (IBMX) in the presence of insulin, and cortisone (e.g. dexamethasone). Preadipocytes are seeded at 70% confluence in serum-containing medium supplemented with 0.5 mM IBMX, 0.1 μM dexamethasone, and 10 μg/ml insulin for 3 days, followed by 3-day treatment with insulin alone, which is then removed at day 6 to finalize differentiation. The protocol works on primary preadipocyte and preadipocyte cell lines such as 3T3-L1 and 3T3-F442A, but not on fibroblasts. Recent work identified multiple small molecules that can enhance the differentiation of preadipocytes to adipocytes in serum-containing medium, including PPARg activators: phenamil, GW7845, RG14620, or Harmine (Park et al. *J. Lipid Research.* 2010; Waki et al. *Cell Met.* 2007). Clinically approved drugs of the thiazolidinedione family (i.e. rosiglitazone, pioglitazone, lobeglitazone) that target PPARg could potentially have similar effects on preadipocytes.

Chicken preadipocyte have yet to be identified, leading most groups to use stromal-vascular cells derived from chicken adipose tissues (Matsubara et al. *Comp. Bio. & Phys* 2008). However, IBMX and dexamethasone have no affect on these chicken preadipocytes, while exposure to 200-400 μM oleic acid induces their differentiation to adipocytes in the presence of serum (Zhouchun et al. *Biosci. Rep.* 2014; Matsubara et al. Comp. Bio. & Phys 2008).

Efforts to differentiate primary CEF to adipocytes showed that exposure to 400 μM oleic acid and 20% serum induced lipid accumulation in the elongated primary cells (Liu et al. *Comp. Bio. & Phys* 2009). The master's thesis of Aishlin Elizabeth Lee (Ohio State U. 2013) showed a similar effect in response to 100-300 μg/l of selenium and 2% serum. Both works used primary chicken cells, cultured in the presence of serum.

To develop a protocol for conversion of the spontaneously immortalized chicken fibroblasts (CSIF line) under serum-free conditions, the present inventor seeded the CSIF at 70% confluence in the optimized serum-free DMEM/F12 medium supplemented with dexamethasone (0.1 μM), 1×ITS+3 (Sigma, 12771), and bFGF (10 ng/ml). The CSIF cells were treated for 4 or 7 days with 200 to 400 μM oleic acid alone, or in combination with 0.5 mM IBMX, or 10 μM of the FDA-approved small molecule Rosiglitazone. While all oleic acid treatments increased lipid accumulation, only the addition of IBMX or Rosiglitazone supported a rounded adipogenic phenotype (FIGS. 4A-D).

Stimulation of Mitochondria Proliferation in Myocytes—

Additionally or alternatively, a dual-PPARα/γ agonist such as naringenin (Goldwasser et al. PLoS One 2010) is used to stimulate mitochondria proliferation in myocytes, expanding their protein content, and adipogenic differentiation of the remaining fibroblasts to fat.

Example 8

Chicken-Based Laboratory Grown Meat: Conversion of a Spontaneously Immortalized Chicken Fibroblast Cell Line into Myocytes Generation of Dox-Inducible MyoD1 and PPARγ Vectors—

Dox-inducible MyoD1 and PPARγ vectors were generated. These vectors are capable of transforming chicken fibroblasts (primary or immortalized) toward myocytes and adipocytes with high efficiency, respectively (data not shown).

Previous work showed that expression of the MyoD1 gene is sufficient to induce myogenesis of human and mouse fibroblasts. A parallel but connected myogenesis pathway goes through Myogenin (MYOG) in mammals.

Experimental Results

Genetic Conversion of CSIF to Myocytes—

To examine if similar conversion of chicken cells to myocytes is possible, the present inventor generated several nucleic acid constructs (vectors) as is schematically illustrated in FIGS. 6-8 and 12. The first construct [FIG. 6, "pInducer-VP64-cMyoD1", SEQ ID NO:3] included the chicken MyoD1 gene (SEQ ID NO:5) cloned into a Dox-inducible lentiviral vector (pInducer20) being fused to the VP64 transcriptional activator (SEQ ID NO: 6) that has been shown to improve MyoD1 induced differentiation in mouse cells (Kabadi et al. *ACS Synthetic Biology.* 2015). A second lentiviral vector (SEQ ID NO:2, FIG. 7) was created for Dox-inducible chicken MYOG expression included the cMyogenin coding sequence (SEQ ID NO: 7) under the control of the minimal CMV promoter (SEQ ID NO: 8). A third lentiviral vector (SEQ ID NO:1, FIG. 12) was created for Dox-inducible chicken MYOD1 expression included the cMyoD1 coding sequence (SEQ ID NO: 5) under the control of the minimal CMV promoter (SEQ ID NO: 8). All three vectors were sequenced and were found to be mutation free (data not shown).

To rapidly detect myogenesis in culture the present inventor created a GFP reporter construct (lentiviral reporter construct; SEQ ID NO: 4, FIG. 8) for the rat myosin light chain-3 promoter-enhancer (rMLC3-GFP), including the rat MLC3 enhancer (SEQ ID NO: 10; 1.5 kb enhancer sequence from the rat MLC3 gene), the rat MLC3 promoter (SEQ ID NO: 11; 628 bp promoter sequence) and the COP-GFP coding sequence (SEQ ID NO: 12). In this lentiviral reporter construct the rat MCL3 enhancer and promoter driving expression of the COP-GFP. This reporter has been shown to be specific and effective in chicken embryos and cells (McGrew et al. *BMC Developmental Biology* 2010). The various constructs were introduced into 293T cells in order to generate lentivirus.

Figure 5A:
FIGS. 5A-E depict conversion of CSIF to myocytes.
Figure 5B:
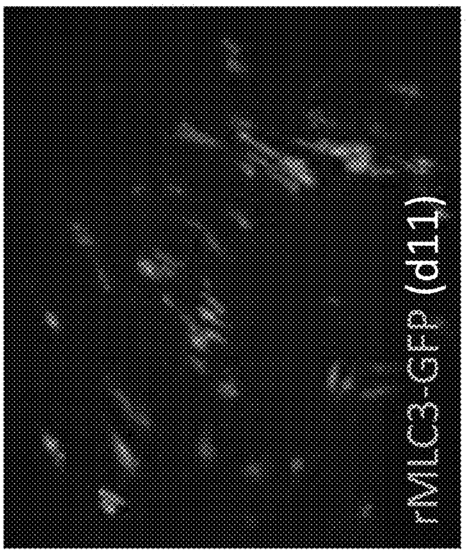
Figure 5C:
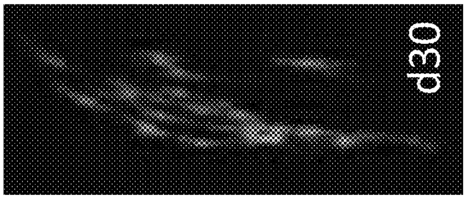
Figure 5D:
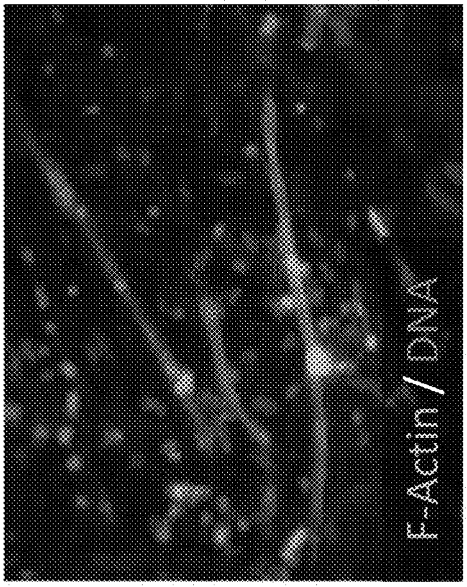
Figure 5E:
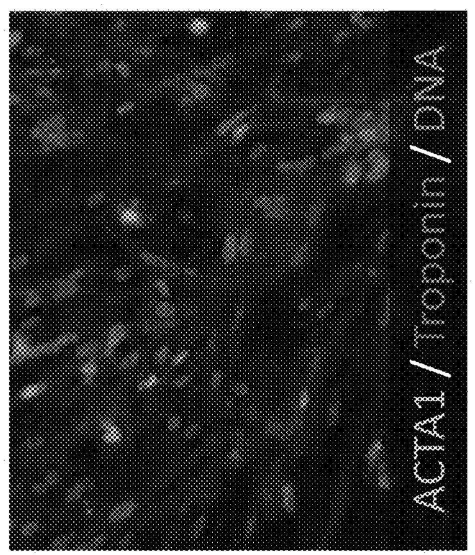
Figure 6:
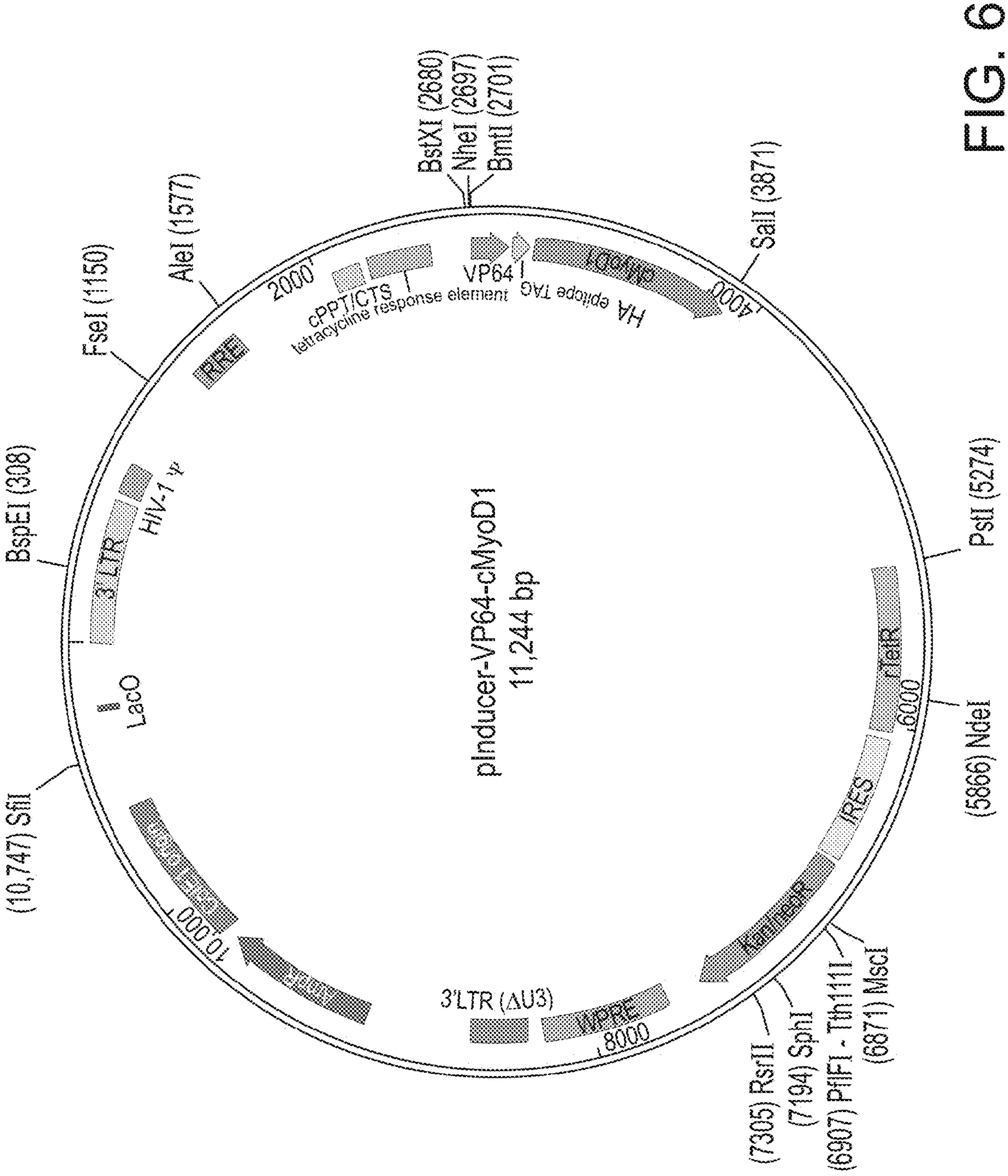
FIG. 6 is a schematic illustration of the pInducer-VP64-cMyoD1 nucleic acid construct used to express chicken MyoD1 in a spontaneously immortalized fibroblast under Dox-induction. Shown are the "central polypurine tract/central termination sequence" (CPPT/CTS) element (in orange), which creates a "DNA flap" that increases nuclear importation of the viral genome during target cell infection and improves vector integration and transduction efficiency); the tetracycline response element (in pink); the VP64 transcriptional activator (in peach); the HA epitope tag (in yellow); and the cMYOD1 coding sequence (in light blue).
Figure 7:
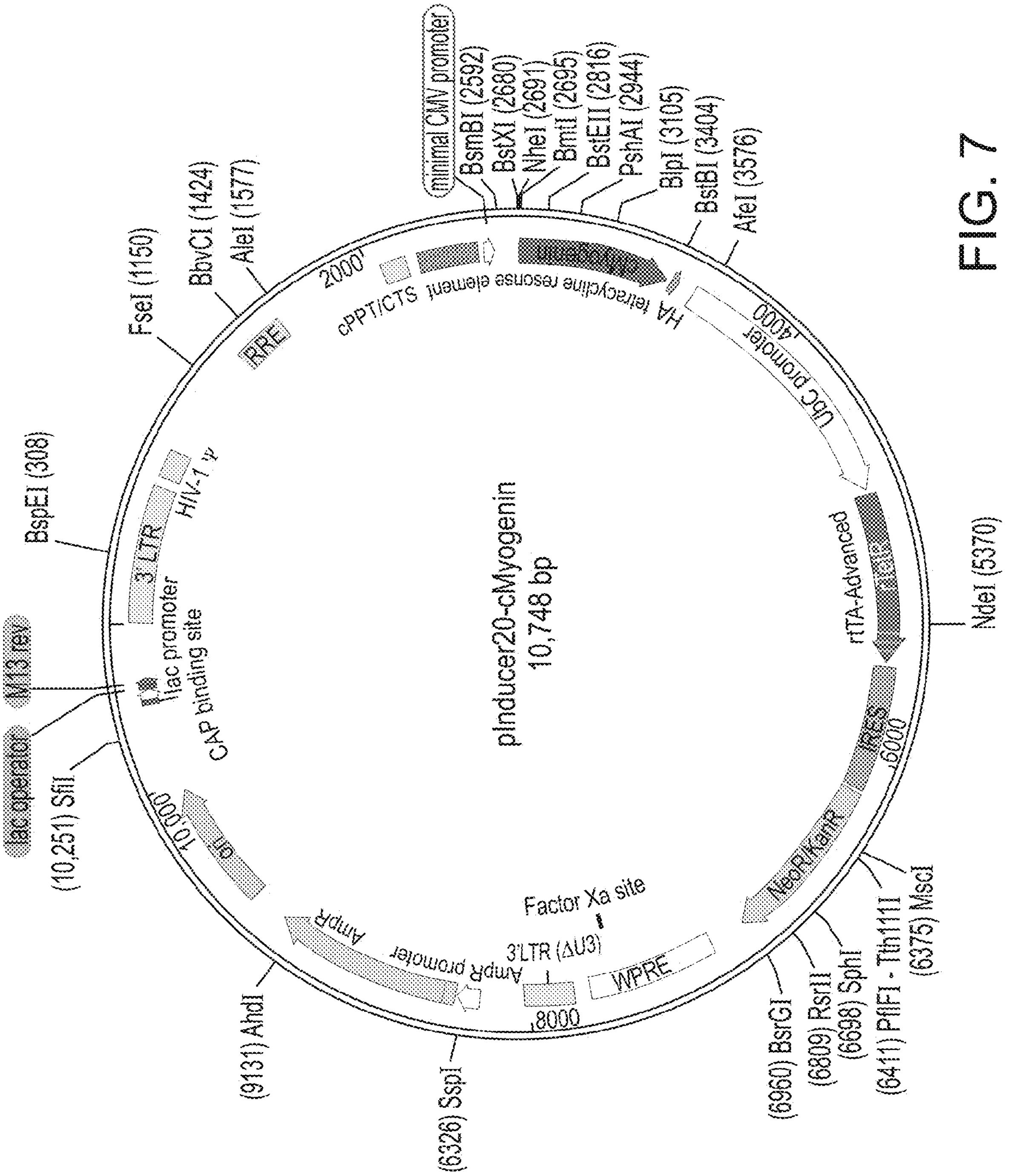
FIG. 7 is a schematic illustration of the pInducer20-cMyogenin nucleic acid construct used to express the chicken myogenin in a spontaneously immortalized fibroblast under Dox-induction. Shown are the "central polypurine tract/central termination sequence" (CPPT/CTS) element (in light peach), the tetracycline response element (in Turquoise); the minimal CMV promoter (white arrow head); and the cMyogenin coding sequence (in light blue).

Primary CEF and CSIF lines were infected 3 times with the lentivirus vectors and split a day later. Cells were cultured in standard DMEM/F12 medium containing 15% serum. CEF and CSIF cultures were induced by doxycycline and were followed for 30 days. While non-induced cultures were negative for GFP (Data not shown), both CEF and CSIF show strong expression of MLC3 by day 11 of culture with cells forming distinct fibers maintained to day 30 of culture (FIGS. 5B and 5C). Immunofluorescence analysis showed F-actin organization and multinucleated (syncytia) fiber formation (FIG. 5D). Staining showed clear induction of α1-skeletal muscle actin (ACTA1) and Troponin T shows a clear muscle phenotype as early as day 7 of induction (FIG. 5E).

As described above in Example 3 hereinabove, a small molecule screen aiming to identify small molecules that can transdifferentiate fibroblasts to muscle cells in the absence of Dox-inducible MyoD1 is carried out using the a GFP reporter construct (lentiviral reporter construct) for the rat myosin light chain-3 promoter-enhancer (FIG. 8). Thus, the present inventor uses variants of small molecule cocktails recently shown to transdifferentiate mouse and human fibroblasts to cardiomyocytes (Cao et al 2016; Fu et al. 2015). A GFP-linked MLC reporter ensures a rapid detection of successful conversion as shown in FIGS. 5B-C.

It should be noted that there are regulatory concerns regarding the use of some small molecules that can affect DNA structure in the reprogramming step. Regulatory agencies are already looking at this issue for human regenerative medicine, while other groups are rapidly producing alternative small molecules for conversion. In contrast to regenerative medicine approaches, the perfusion system of some embodiments of the invention can rapidly flush the system and remove any residual small molecules before the process terminates. Additionally or alternatively, a Dox-inducible differentiation method can be used as shown in FIGS. 5A-E.

Metabolomic analysis of the perfusate and tissue is carried out over time to identify which nutrients are rate limiting (i.e. missing). A metabolic flux balance model of the tissue is established (as described in Levy et al. 2016) which allows to see changing fluxes and determine the metabolic requirements of the cells. Growth factors are introduced in access and their removal is determined by protein array analysis, as small molecules are to replace them. Metabolic analysis using Jobst Technologies (Freiburg, German) metabolic sensors and an oxygen sensor, showed proliferating CSIF consume oxygen at a rate of 2.4 nmol/min/$10^6$ cells, consume glucose at a rate of 1.8 nmol/min/$10^6$ cells and produce lactate at a rate of 198 pmol/min/$10^6$ cells during the growth phase.

Example 9

Generation of a Hybrid of Plant-Based Meat Substitute Product with Laboratory Grown Fat A meat analogue, also called a meat substitute, approximates certain aesthetic qualities (primarily texture, flavor and appearance) or chemical characteristics of specific types of meat. Many analogues are based on cereal, gluten, or legumes such as soy or pea. Global meat substitute market was $3.3 billion in 2014, and grows at a CAGR of 7.5% including products such as veggie burgers, soy hotdogs, and chicken nuggets. However, these products fail to emulate the flavor and aroma of animal meat. Recent work on plant-based meat substitutes identified fermented leghemoglobin (also called "(also leghaemoglobin or legoglobin") as a source for a metallic flavor resembling blood. Using molecular gastronomy tools companies such as Impossible Foods and Beyond Meat produced ground meat-like patty with the texture and aroma of beef. However, the cooking of protein-bound saturated fat produces the distinct flavor of meat. Current products use coconut or palm oil as a source of palmitate (16:0) that is solid at room temperature, but rapidly melts at 62.9° C. This results in an oily, dripping product that is distinct from real beef. Similarly, several companies such as Beyond Meat extrude layered legume protein to create the texture and mouth feel of chicken strips. Similar lack of animal fat results in a dry mouth feel distinct from real chicken.

To produce animal fat, CSIF are cultured in serum free medium composed of DMEM/F12 supplemented with dexamethasone (0.1 μM), bFGF (10 ng/ml), long IGF-1 (Sigma 11271) (5 ng/ml), 12 μM linoleic acid, and 2 mM of L-Analyl-L-Glutamine. Cells are cultured in fed-batch bioreactors, perfusion bioreactors, or closed-loop perfusion described above to a density of 10×$10^6$ cells/ml. Medium further supplemented with 400 μM oleic acid and 10 μM rosiglitazone. Cells acquire lipid droplets and reach a density of 100×$10^6$ cells/ml. The adipocyte slurry is concentrated and added as raw material to the plant-based matrix composed of cereal or legume-based protein isolate such as the Pea Protein Organic Powder (Now Sports). Raw material density is changed as a function of the desired end product. Chicken strips require 5 to 10% laboratory grown adipocytes, resulting in about 1.5×$10^8$ cells in final product. Hamburgers require 10 to 20% laboratory grown adipocytes, resulting in about 3×$10^8$ cells in final product.

Example 10

Generation of a Chicken Patty or Nugget in a Stirred Bioreactor

Culturing of Chicken Fibroblasts in a Stirred Bioreactor—

Chicken fibroblasts can be cultured in a stirred bioreactor (BioFlo® 320) in small single use vessels of 250-400 mL volume.

The cells are aggregated into small micro-clusters and are cultured in suspension without micro-carrier beads. This permits the high-density growth of cells reaching 4-6×$10^6$ cells/mL. Once this density is reached a chicken patty or nugget with a density of 200×$10^6$ cells/gram is prepared for a public tasting.

Alternatively, fibroblasts can be grown on collagen-coated micro-carrier beads (e.g. SoloHill Engineering) as previously described (Ang & Ma Sha 2015).

Example 11

Establishment and Isolation of Chicken Embryonic Endothelial Cells

Differentiation of Chicken Induced Pluripotent Stem Cells (iPSCs) into Endothelial Cells—

Using chicken fibroblasts (non-immortalized) the present inventor generated chicken induced pluripotent stem cells (iPSCs) essentially as described by Vodyanik et al. 2010. Then the chicken iPSCs are used for the differentiation of chicken endothelial cells in a similar manner to human and mouse derived cells (Giacomelli et al. Development 2017). The iPS-derived chicken endothelial cells can be used as is with limited population doubling (up to 20) or can be used to generate spontaneously immortalized endothelial cells as described below.

Spontaneous Immortalization of Chicken Endothelial Cells—

Chicken microvascular endothelial cells which are either obtained from a commercial source (Charles River Labs) or which are isolated from young chickens according to established protocols (Twal & Leach In Vitro Cell. Dev. Biol. Animal 1996) are then being cultured on 50 μg/ml collagen type I or 0.2% gelatin in standard culture medium, such as EGM2mv (Lonza, Switzerland) or serum free formulation (e.g. ThermoFisher #11111044) containing bFGF (20 ng/ml), EGF (10 ng/ml), and human plasma fibronectin (10 µg/ml) until a spontaneous immortalization occurs, so as to obtain a chicken endothelial cell line which is not genetically modified.

It is noted that the present inventor was able to obtain a spontaneously immortalized endothelial cell from rat cardiac microvascular endothelial cells purchased from Vec Technologies (Rensselaer, NY), reaching at least population doubling 120 (data not shown), thus proving that a spontaneous immortalization of endothelial cells is feasible.

Example 12

Generation of Chicken Muscle Using Sponges

Generation of Chicken Muscle Tissue by Co-Culturing of Spontaneously Immortalized Fibroblasts and Spontaneously Immortalized Endothelial Cells on Sponges (Scaffolds)—

The present inventor has designed generation of chicken muscle by seeding spontaneously immortalized chicken fibroblasts and spontaneously immortalized rat endothelial cells mixtures into a biodegradable large pore sponges, such as collagen hydrogel, that permits rapid vascularization and uniform distribution of nutrients. The micro-tissue is characterized by confocal and electron microscopy.

Other suitable sponges (scaffolds) include, but are not limited to, polylactic acid, polyglycolic acid, or poly(lactic-co-glycolic acid), sponges, polyglicolic acid sponges, Variotis™ (Biometic, AU) or Cellusponge™ (hydroxypropyl cellulose. Bio-Byblos Catalogue No. Z741057).

It is noted that one possible way of avoiding loss of cells by the perfusion system, is to first embed the cells in an injectable hydrogel polypeptide matrix which is then being injected into the biodegradable sponge.

The micro-tissue scaffold is cultured under perfusion and the cell proliferation and metabolic uptake of nutrients and growth factors was tracked as shown in Table 2 below. Non-specific absorption by the system is monitored, even in the absence of cells, since this could lead to loss of peptides and lipids.

TABLE 2

| Metabolic Flux | Measurement |
| --- | --- |
| Oxygen Consumption Rate | 2.4 nmol/min/$10^6$ cells |
| Glucose Uptake Rate | 1.8 nmol/min/$10^6$ cells |
| Lactate Production Rate | : 198 pmol/min/$10^6$ cells |

Growth rates and metabolic parameters are reintroduced into the model and systems parameters are adjusted.

Cell growth and the maximal cell density are determined in the absence of dialysis.

Following the successful demonstration of cell growth under perfusion the tissue organization and the proper vascular connectivity and distribution are characterized as shown in FIGS. 11A-C. Spontaneously immortalized chicken fibroblasts (CSIF) and spontaneously immortalized rat microvascular endothelial cells (RCEC) were suspended at a density of $150 \times 10^6$ CSIF/ml and $15 \times 10^6$ RCEC/ml in collagen type 1 scaffold and seeding for microscope evaluate and perfusion. High-density tissue formed overnight and compacted the collagen scaffold. As shown by sulforhodamine B stain, the cultured cells revealed high protein content (FIG. 11A). The tissue seeded in the bioreactor were sealed and perfused in serum free medium, without antibiotics for 11 days. No loss of cell mass was observed. Confocal analysis showed clear organization of vascular structures and associated tissue.

Growth factors and cytokines are used to define vascular maturation. Tissue assembly and growth are characterized by live imaging and end point microscopic evaluation. Once cell density outstrips nutrient uptake, perfusion rate through the nested dialysis circuit is increased to rapidly remove toxins while adding stable supply of nutrients to the growing tissue. The above-described model shows that the minimal perfusion rate required to support cell growth increases exponentially with time or linearly with tissue mass to supply the oxygen consumption rates of the cells. A minimal perfusion rate of 36.9 ml/s is necessary to sustain 1 kg of tissue in ambient 21% oxygen, but only 8.2 ml/s is be required if oxygen partial pressure is raised to 95% in the oxygenator. The minimal perfusion rate can decrease by increasing the oxygen carrying capacity of the medium using an oxygen carrier such as perfluorocarbon emulsion (e.g. Fluosol) or modified hemoglobin (e.g. Hemopure). Hemopure® is a hemoglobin-based oxygen carrier manufactured by HbO2 Therapeutics LLC that has an oxygen carrying capacity of 1.39 ml O2/g Hb, meaning that if we add 3.55 µg of Hemopure per ml of media we double the oxygen content, decreasing by 2 the perfusion rate needed to perfuse a large bulk of tissue.

The model also suggests that glucose is not a limiting factor for perfusion, as flow rates under 0.4 ml/sec can deliver sufficient glucose to over 1 kg of cells. However, as glucose if is not replenished, 1 kg of tissue will consume all glucose in the system within 48 minutes. A total of 140 grams of glucose are required for tissue growth. Glucose only becomes limiting when tissue passes 24 grams in mass, and will need to be added at hourly intervals on the final two days of growth.

Alternatively, tissue growth is explored in edible hollow fiber cartridge, where nutrient supply is homogenously distributed in the absence of an integrated vascular network. Here, the fibers of the cartridge are made from edible natural or synthetic polymers, such as cellulose (FiberCell, #C3008), and the cells form a mass surrounding the fibers. Cellulose is FDA approved as GRAS, and used to control moisture and stabilizer shredded cheese, bread, and various sauces.

Example 13

A prototype system as been designed, according to some embodiments of the present invention. The prototype system is illustrated schematically in FIG. 9, and is based on a closed loop dialysis bioreactor. The core circuit is a recirculating perfusion bioreactor, 1 to 5 liters in volume, that grows muscle tissue growing from 20 mg to 1000 grams, and that retains cells using a hollow fiber cartridge, packed bed design, or vascularized embedded tissue configuration. An increasing percentage of the bioreactor outflow is circulated through a counter flow dialysis, whose pores are designed to exclude albumin, about 30 kDa molecular weight cutoff. As the cells are not present during this filtration step it can occur at high pressures. This design retains the albumin and with it the growth factors and lipids is carries in the medium. Another perfusion circulates the dialysate through a filter that removes ammonia and toxins (e.g. Zeolite molecular sieve). This design can reach the volume/mass ratio of animals, nominally 100 ml per kg mass. It is estimated that about 2 liters medium can be used with per 5 liters bioreactor volume. This design can produce 2.5 kg mass every 10 days, consuming only 2 liters of medium, as it does not require a seed train. This translates to $4 per kg mass for the medium costs alone.

Capital costs are also considered. Current estimate of the bill of parts using off the shelf components is about $7,000, suggesting manufacturing costs of about $300 for a system having a 5 liter bioreactor chamber. A production facility with 5,000 such systems can cost about $1.5 million, so that an estimate of about $5 million for the entire facility. Assuming the same 10% annual depreciation and maintenance costs, a production capacity of about 450,000 kg/year is obtained with about $500,000 annual costs to maintain. This results in a capital cost of only about $1.1 per kg mass produced.

The prototype system is composed of a primary tissue perfusion circuit and a secondary dialysis circuit for nutrient and toxin exchange. The primary circuit includes culture medium perfusate that is recirculated using a peristaltic pump through a jacketed tissue growth chamber, an oxygenator, a heat exchanger, and a bubble trap. The oxygenator is gassed with a mixture of 95% $O_2$, 5% $CO_2$ and 15% $N_2$ maintaining constant pH.

A fraction of the perfusate is diverted to a secondary circuit through a hollow fiber dialyzer, such as Spectrum Labs (Rancho Dominguez, CA) with up to 790 $cm^2$ membrane area and a 30 kDa molecular weight cutoff (the total filtration surface area in a human kidney is only 516.1 $cm^2$). A particular advantage of the dialysis of the present embodiments is that albumin, with a molecular weight of 66.5 kDa, is retained in the main perfusion circuit, as further detailed hereinabove.

The secondary circuit dialyzes the perfusate using counter-flow to maximize diffusion, against a protein-free dialysate, recirculated through an ammonia filter using another peristaltic pump. Ammonia filters such as Zeolites trap clearing the ammonia from the solution. Temperature within the bioreactor are optimized between 38° C. to 40.5° C. mimicking the normal body temperature of chickens.

Perfusion and nutrient consumption rates are also considered. Under ambient conditions, partial pressure of 21% (160 mmHg) of oxygen results in a concentration of 220 nmol $O_2$/ml medium. Using a SeaHorse Bioanalyzer the Inventor showed that chicken embryonic fibroblasts consume 2.4 nmol 02/min/$10^6$ cells. Considering that 1 g of tissue contains approximately $200\times10^6$ cells, a perfusion rate of about 36.9 ml/s is sufficient to sustain 1 kg of tissue in standard incubators gas pressures. If oxygen partial pressure is raised to 95%, a perfusion rate of about 8.2 ml/s is sufficient.

Glucose consumption is additionally considered. Using online sensors, a glucose uptake rate of 1.8 nmol/min/$10^6$ cells, and lactate production rate of 198 pmol/min/$10^6$ cells were measured for chicken embryonic fibroblasts. Considering that DMEM/F12 medium contains 3.15 g/L of glucose, the perfusion rate required to sustain 1 kg of tissue would be 0.36 ml/sec. Therefore, glucose is not a limiting factor for medium perfusion. Yet, continuous addition of glucose is preferred, optionally at narrowing intervals, during late stage culture, since at this rate 1 kg tissue consumes the glucose in 1 liter medium within about 48 min.

Figure 10A:
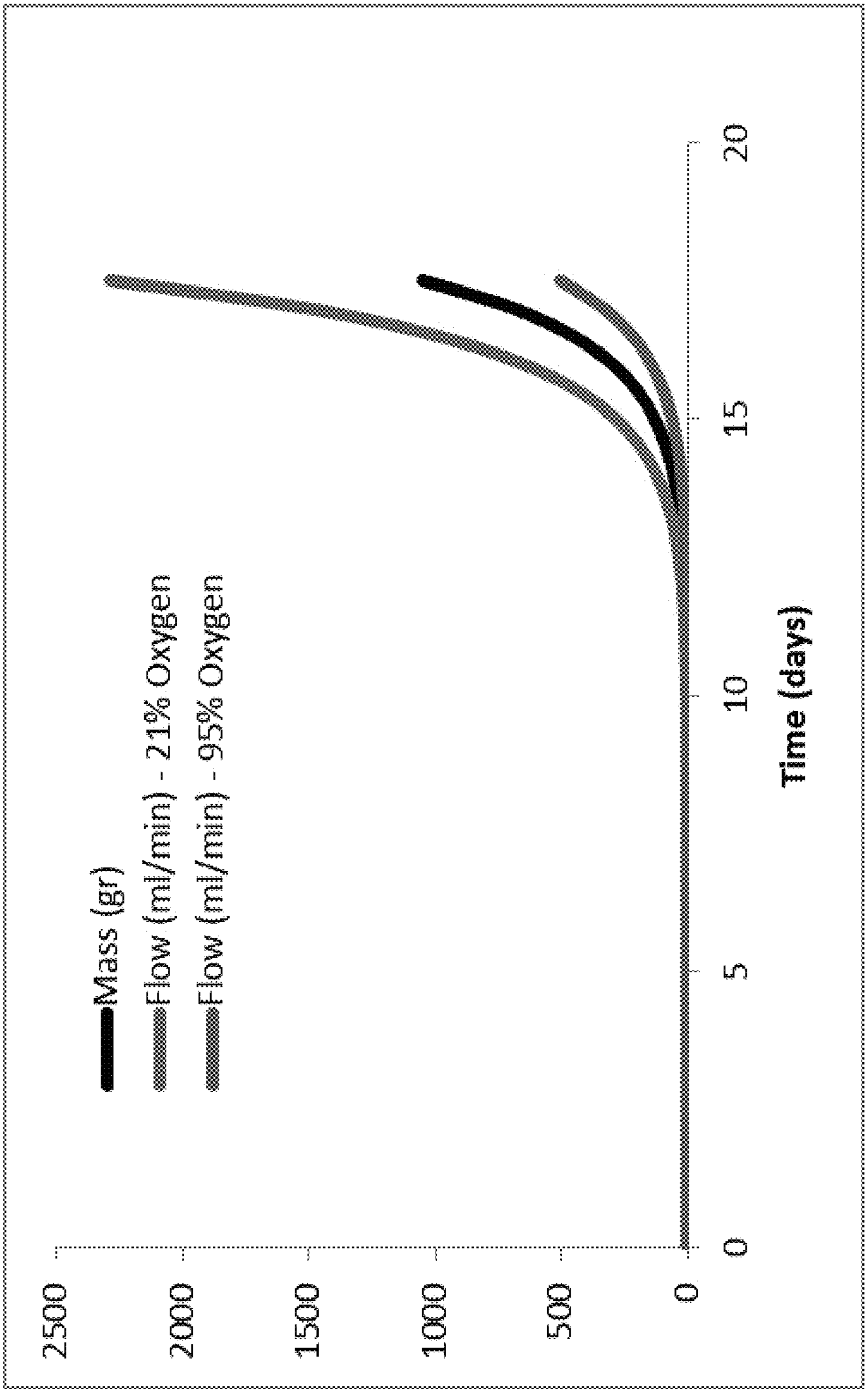
FIGS. 10A and 10B are graph showing the produce mass and applied perfusion rates (FIG. 10A), and accumulated glucose consumption (FIG. 10B), as obtained in experiments performed according to some embodiments of the present invention.
Figure 10B:
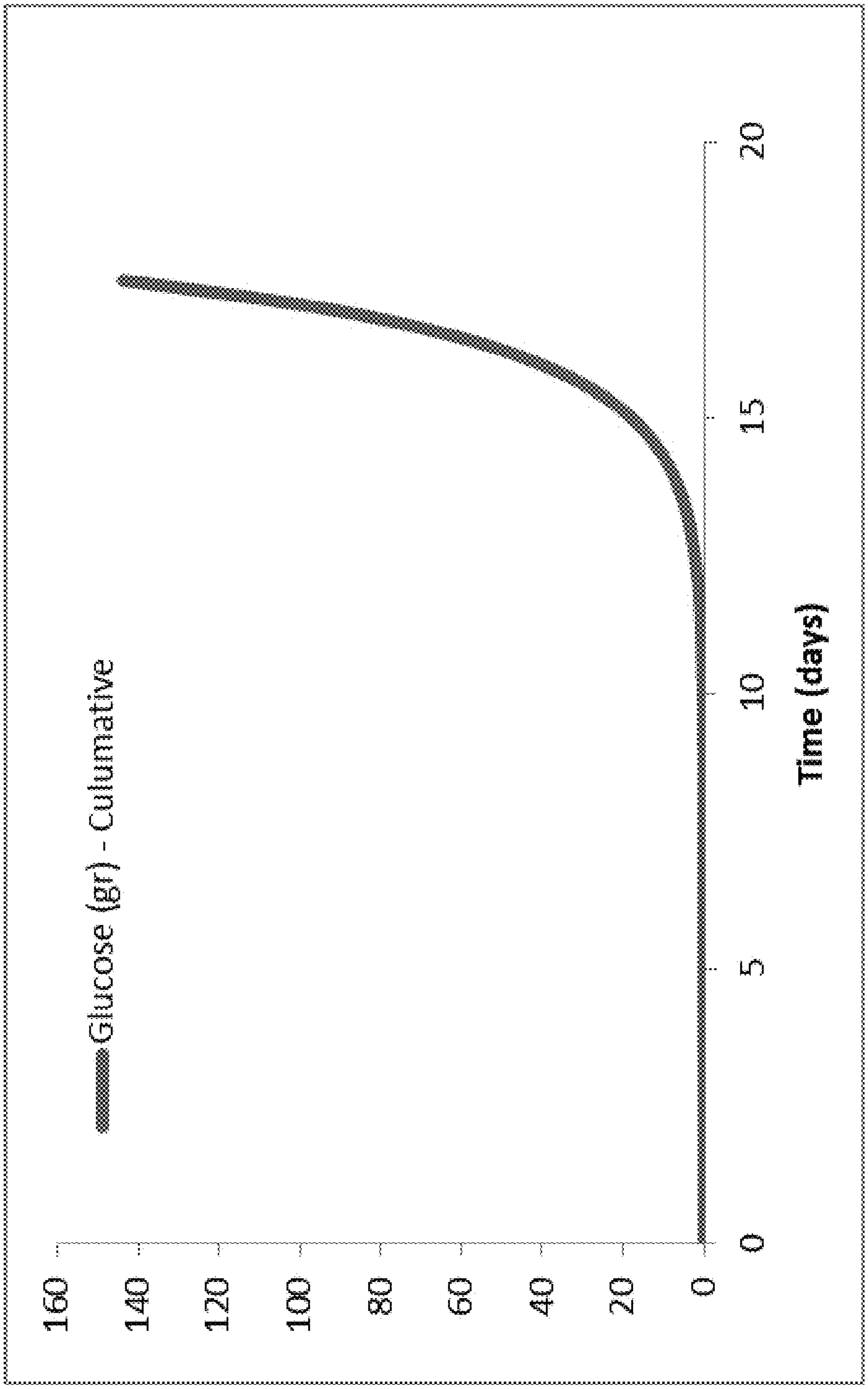

FIGS. 10A and 10B are graph showing the produce mass and applied perfusion rates (FIG. 10A), and accumulated glucose consumption (FIG. 10B). In this example, an exponential growth rate characterized by a doubling time constant of 20 h has been employed. At this growth rate, it is preferred to add glucose starting from the day 13, so as to provide the glucose demand.

The peristaltic pumps are selected to provide perfusion rate of at least 36 ml/s, particularly towards the last days of the cycle (e.g., beginning of the 13th day). Yet, this rate can be decreased using different strategies such as oxygen transporters to increase basal level of $O_2$ in the media. For example, Hemopure® is a hemoglobin-based oxygen carrier manufactured by $HbO_2$ Therapeutics LLC that has an oxygen carrying capacity of 1.39 ml $O_2$/g Hb, meaning that adding 3.55 μg of Hemopure per ml of media the oxygen content can be doubled, and the perfusion rate can be decreasing by a factor of 2.

Table 3 below provides a comparison between the fed-batch process, the concentrated perfusion process, and the technique according to exemplary embodiments of the invention.

TABLE 3

| Parameter | Fed-Batch | Circulating Perfusion | The inventive technique |
|---|---|---|---|
| Seed Train | 20 L, 80 L, 400 L, 2000 L | 20 L run for 10 days; 6 reactor volumes | None |
| Production Reactor | 10,000 L | 1,000 L | 5 L |
| Cell Density | 25 × $10^6$ | 100 × $10^6$ | 100 × $10^6$ |
| Growth Phase | 19 days | 30 days | 10 days |
| Media Consumption | 12,500 L | 2,120 L | 2 L |
| Media Cost | $20/L | $5/L | $5/L |
| Consumable Costs | +$200/kg | +$21/kg | +$4/kg |
| Facility Cost | $50M | $30M | $5M* |
| Capital Burden | $5M | $3M | $0.5M |
| Production Capacity | 24,000 kg/yr | 6,000 kg/yr | 450,000 kg/yr |
| Capital Costs | +$200/kg | +$500/kg | +$1/kg |

*5,000 small 5 L bioreactors in a factory

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

REFERENCES

Additional References are Cited in Text

1. *Long-term culture and expansion of primary human hepatocytes*. G. Levy, D. Bomze, S. Heinz, S. D. Ramachandran, A. Noerenberg, M. Cohen, O. Shibolet, E. Sklan, J. Braspenning, Y. Nahmias. 2015, Nature biotechnology, pp. 1264-1271.
2. *An active bubble trap and debubbler for microfluidic systems*. A. M. Skelley, J. Voldmana. 2008, The Royal Society of Chemistry, pp. 1733-1737.
3. *Real-time monitoring of metabolic function in liver-on-chip microdevices tracks the dynamics of mitochondrial dysfunction*. D. Bavli, S. Prill, E. Ezra, G. Levy, M. Cohen, M. Vinken, J. Vanfleteren, M. Jaeger, Y. Nahmias. E2231-E2240, s.l.: PNAS, 2016.
4. *Chick stem cells: current progress and future prospects*. S. Intarapat, C. D. Stern. 2013, Stem cell research, pp. 1378-1392.
5. *Avian-induced pluripotent stem cells derived using human reprogramming factors*. Y. Lu, F. D. West, B. J. Jordan, J. L. Mumaw, E. T. Jordan, A. Gallegos-Cardenas, R. B. Beckstead, S. L. Stice. s. l.: Stem Cells Dev., 2012, Vols. 394-403.
6. *Mammalian genes induce partially reprogrammed pluripotent stem cells in non-mammalian vertebrate and invertebrate species*. R. A. Rossello, C. C. Chen, R. Dai, J. T. Howard, U. Hochgeschwender, E. D. Jarvis. 2013, eLife 2.
7. *Pluripotent stem cells induced from mouse somatic cells by small-molecule compounds*. P. Hou, Y. Li, X. Zhang, C. Liu, J. Guan, H. Li, T. Zhao, J. Ye, W. Yang, K. Liu, J. Ge, J. Xu, Q. Zhang, Y. Zhao, H. Deng. 2013, Science, pp. 651-654.
8. *Identification of small molecules for human hepatocyte expansion and iPS differentiation*. J. Shan, R. E. Schwartz, N. T. Ross, D. J. Logan, D. Thomas, S. A. Duncan, T. E. North, W. Goessling, A. E. Carpenter, S. N. Bhatia. 2013, Nature chemical biology, pp. 514-520.
9. *Conversion of human fibroblasts into functional cardiomyocytes by small molecules*. N. Cao, Y. Huang, J. Zheng, C. I. Spencer, Y. Zhang, J. D. Fu, B. Nie, M. Xie, M. Zhang, H. Wang, T. Ma, T. Xu, G. Shi, D. Srivastava, S. Ding. 2016, Science.
10. *Direct reprogramming of mouse fibroblasts into cardiomyocytes with chemical cocktails*. Y. Fu, C. Huang, X. Xu, H. Gu, Y. Ye, C. Jiang, Z. Qiu, X. Xie. 2015, Cell research, pp. 1013-1024.
11. *Endothelium-mediated hepatocyte recruitment in the establishment of liver-like tissue in vitro*. Y. Nahmias, R. E. Schwartz, W. S. Hu, C. M. Verfaillie, D. J. Odde. 2006, Tissue engineering, pp. 1627-1638.
12. *Recovery of warm ischemic rat liver grafts by normothermic extracorporeal perfusion*. H. Tolboom, R. E. Pouw, M. L. Izamis, J. M. Milwid, N. Sharma, A. Soto-Gutierrez, Y. Nahmias, K. Uygun, F. Berthiaume, M. L. Yarmush. 2009, Transplantation, pp. 170-177.
13. *Real-time monitoring of metabolic function in liver-on-chip microdevices tracks the dynamics of mitochondrial dysfunction*. D. Bavli, S. Prill, E. Ezra, G. Levy, M. Cohen, M. Vinken, J. Vanfleteren, M. Jaeger, Y. Nahmias. 2016, Proceedings of the National Academy of Sciences of the United States of America, pp. E2231-2240.
14. *Real-time monitoring of oxygen uptake in hepatic bioreactor shows CYP450-independent mitochondrial toxicity of acetaminophen and amiodarone*. S. Prill, D. Bavli, G. Levy, E. Ezra, E. Schmalzlin, M. S. Jaeger, M. Schwarz, C. Duschl, M. Cohen, Y. Nahmias. 2016, Archives of toxicology, pp. 1181-1191.
15. *Serum free primary human fibroblast and keratinocyte coculture*. S. Mujaj, K. Manton, Z. Upton, S. Richards. 2010, Tissue engineering, pp. 1407-1420.
16. *Insulin-like growth factor I stimulates myoblast expansion and myofiber development in the limb*. P. J. Mitchell, S. E. Johnson, K. Hannon. 2002, Developmental dynamics: an official publication of the American Association of Anatomists, pp. 12-23.
17. *Screening and discovery of nitro-benzoxadiazole compounds activating epidermal growth factor receptor (EGFR) in cancer cells*. V. Sakanyan, M. Angelini, M. Le Bechec, M. F. Lecocq, F. Benaiteau, B. Rousseau, A. Gyulkhandanyan, L. Gyulkhandanyan, C. Loge, E. Reiter, C. Roussakis, F. Fleury. 2014, Scientific reports, p. 3977.
18. *Differentiation of pluripotent stem cells to muscle fiber to model Duchenne muscular dystrophy*. J. Chal, M. Oginuma, Z. Al Tanoury, B. Gobert, O. Sumara, A. Hick, F. Bousson, Y. Zidouni, C. Mursch, P. Moncuquet, O. Tassy, S. Vincent, A. Miyanari, A. Bera, J. M. Gamier, G. Guevara, M. Hestin, L. Kennedy, S. Hayashi, B. Drayton, T. Cherrier, B. Gayra. 2015, Nature biotechnology, pp. 962-969.
19. *MyoD converts primary dermal fibroblasts, chondroblasts, smooth muscle, and retinal pigmented epithelial cells into striated mononucleated myoblasts and multinucleated myotubes*. J. Choi, M. L. Costa, C. S. Mermelstein, C. Chagas, S. Holtzer, H. Holtzer. 1990, Proceedings of the National Academy of Sciences of the United States of America, pp. 7988-7992.
20. *Tet-on inducible system combined with in ovo electroporation dissects multiple roles of genes in somitogenesis of chicken embryos*. T. Watanabe, D. Saito, K. Tanabe, R. Suetsugu, Y. Nakaya, S. Nakagawa, Y. Takahashi. 2007, Developmental biology, pp. 625-636.
21. *Efficient selection for high-expression transfectants with a novel eukaryotic vector*. H. Niwa, K. Yamamura, J. Miyazaki. 1991, Gene, pp. 193-199.
22. *A zebrafish embryo culture system defines factors that promote vertebrate myogenesis across species*. C. Xu, M. Tabebordbar, S. Iovino, C. Ciarlo, J. Liu, A. Castiglioni, E. Price, M. Liu, E. R. Barton, C. R. Kahn, A. J. Wagers, L. I. Zon. 2013, Cell, pp. 909-921.
23. *Skeletal myogenesis by human embryonic stem cells*. J. K. Zheng, Y. Wang, A. Karandikar, Q. Wang, H. Gai, A. L. Liu, C. Peng, H. Z. Sheng. 2006, Cell research, pp. 713-722.
24. *Long-term in vitro culture and characterisation of avian embryonic stem cells with multiple morphogenetic potentialities*. B. Pain, M. E. Clark, M. Shen, H. Nakazawa, M. Sakurai, J. Samarut, R. J. Etches. 1996, Development, pp. 2339-2348.
25. *Identification of Small Molecules Which Induce Skeletal Muscle Differentiation in Embryonic Stem Cells via Activation of the Wnt and Inhibition of Smad2/3 and Sonic Hedgehog Pathways*. H. Lee, C. Haller, C. Manneville, T. Doll, I. Fruh, C. G. Keller, S. M. Richards, Y. Ibig-Rehm, M. Patoor, M. Goette, L. C. Bouchez, M. Mueller. 2016, Stem cells, pp. 299-310.
26. *Building muscle: molecular regulation of myogenesis*. C. F. Bentzinger, Y. X. Wang, M. A. Rudnicki. 2012, Cold Spring Harbor perspectives in biology.
27. *Glycolysis-mediated changes in acetyl-CoA and histone acetylation control the early differentiation of embryonic stem cells*. A. Moussaieff, M. Rouleau, D. Kitsberg, M.

Cohen, G. Levy, D. Barasch, A. Nemirovski, S. Shen-Orr, I. Laevsky, M. Amit, D. Bomze, B. Elena-Herrmann, T. Scherf, M. Nissim-Rafinia, S. Kempa, J. Itskovitz-Eldor, E. Meshorer, D. Aberdam, Y. Nahmias. 2015, Cell metabolism, pp. 392-402.

28. *Roxarsone, inorganic arsenic*, and *other arsenic* species *in chicken: a U.S.-based market basket sample*. K. E. Nachman, P. A. Baron, G. Raber, K. A. Francesconi, A. Navas-Acien, D. C. Love. 2013, Environmental health perspectives, pp. 818-824.

29. *Multidrug-Resistant Staphylococcus aureus in US Meat and Poultry*. A. E. Waters, T. Contente-Cuomo, J. Buchhagen, C. M. Liu, L. Watson, K. Pearce, J. T. Foster, J. Bowers, E. M. Driebe, D. M. Engelthaler, P. S. Keim, L. B. Price. 2011, Clinical infectious diseases: an official publication of the Infectious Diseases Society of America, pp. 1227-1230.

30. *Micropatterning of living cells by laser-guided direct writing: application to fabrication of hepatic-endothelial sinusoid-like structures*. Y. Nahmias, D. J. Odde. 2006, Nature protocols, pp. 2288-2296.

31. *Integration of technologies for hepatic tissue engineering*. Y. Nahmias, F. Berthiaume, M. L. Yarmush. 2007, Advances in biochemical engineering/biotechnology, pp. 309-329.

32. *Vascularized and functional human liver from an iPSC-derived organ bud transplant*. T. Takebe, K. Sekine, M. Enomura, H. Koike, M. Kimura, T. Ogaeri, R. R. Zhang, Y. Ueno, Y. W. Zheng, N. Koike, S. Aoyama, Y. Adachi, H. Taniguchi. 2013, Nature, pp. 481-484.

33. *A novel formulation of oxygen-carrying matrix enhances liver-specific function of cultured hepatocytes*. Y. Nahmias, Y. Kramvis, L. Barbe, M. Casali, F. Berthiaume, M. L. Yarmush. 2531-2533, s.l.: FASEB, 2006.

What is claimed is:

1. A system for growing cells, the system comprising:

a bioreactor chamber for growing the cells;

a delivery system configured to deliver a perfusion solution to the bioreactor chamber for perfusion of the perfusion solution through the cells at a perfusion rate;

a dialysis system having a dialyzer and a dialysate for performing a dialysis and a filter for filtering the dialysate and reducing ammonia content in the dialysate; and a computerized controller for controlling the bioreactor chamber, the delivery system, and the dialysis system, wherein the computerized controller is configured to circulate the perfusion solution out of the bioreactor chamber through the dialyzer and back into the bioreactor chamber, and to circulate the dialysate out of the dialyzer through the filter and back into the dialyzer, wherein the dialyzer is configured with a membrane that has a molecular weight cutoff of less than 30 kDa to ensure that at least one protein exiting the bioreactor chamber with the perfusion solution is circulated back into the bioreactor chamber without entering the dialysate, and wherein the bioreactor chamber is configured to maintain at least 95% of the cells in the bioreactor chamber during circulation of the perfusion solution.

2. The system according to claim 1, wherein at least 90% of a volume of the perfusion solution that exits the bioreactor chamber is circulated back into the bioreactor chamber during an entire growth period of the cells.

3. The system according to claim 1, wherein the cells form a tissue.

4. The system according to claim 1, wherein the cells form a cultured meat product.

5. The system according to claim 1, wherein the cells form a suspension cell culture.

6. The system according to claim 1, wherein the computerized controller increases the perfusion rate over time.

7. The system according to claim 1, wherein there is a plurality of bioreactor chambers, all being in fluid communication with the same dialyzer, and wherein the dialyzer applies the dialysis to perfusion solutions circulated out of each of the bioreactor chambers.

8. The system according to claim 1, wherein the at least one protein is albumin.

9. The system according to claim 1, wherein there is from about 0.1 liters to about 10 liters of the perfusion solution per one kilogram of cells in the bioreactor chamber.

10. The system according to claim 1, wherein the delivery of the perfusion solution is via a fluidic circuit constituted to enrich the perfusion solution by a culture medium and oxygen.

11. The system according to claim 10, wherein the fluidic circuit is constituted to trap or remove bubbles present in the perfusion solution.

12. The system according to claim 10, wherein the fluidic circuit is constituted to heat the perfusion solution.

13. The system according to claim 1, wherein the delivery and the circulation is without discarding the perfusion solution throughout the cell growth.

14. The system according to claim 1, wherein the cells form a cultured meat product and wherein the bioreactor chamber is at most 5 liters in volume.

15. The system according to claim 1, wherein the bioreactor chamber is at most 5 liters in volume.

16. A system for growing cells, the system comprising:

a bioreactor chamber for growing the cells;

a delivery system configured to deliver a perfusion solution to the bioreactor chamber for perfusion of the perfusion solution through the cells at a perfusion rate;

a dialysis system having a dialyzer for performing a dialysis and a filter for filtering the dialysate and reducing ammonia content in the dialysate; and a computerized controller configured to increase the perfusion rate with time, and to circulate the perfusion solution out of the bioreactor chamber, separately through the dialyzer and the delivery system, and back into the bioreactor chamber, wherein the dialyzer is configured with a membrane that has a molecular weight cutoff of less than 30 kDa to ensure that at least one protein exiting the bioreactor chamber with the perfusion solution is circulated back into the bioreactor chamber without entering the dialysate, wherein the bioreactor chamber is configured to maintain at least 95% of the cells in the bioreactor chamber during circulation of the perfusion solution, and wherein at least 90% of a volume of the perfusion solution that exits the bioreactor chamber is circulated back into the bioreactor chamber during an entire growth period of the cells.

17. A method of growing cells using the system of claim 1, the method comprising:

growing the cells in the bioreactor chamber;

delivering through the delivery system to deliver the perfusion solution to the bioreactor chamber;

circulating the perfusion solution out of the bioreactor chamber through the dialysis system having the dialyzer therein and back into the bioreactor chamber; and circulating the dialysate out of the dialyzer as controlled by the computerized controller, through the filter selected for filtering the dialysate and reducing ammonia content in the dialysate, and back into the dialyzer.

18. A method of growing cells using the system of claim 1, the method comprising:

growing the cells in the bioreactor chamber;

delivering by the delivery system the perfusion solution to the bioreactor chamber for perfusion of the perfusion solution through the cells at a perfusion rate that increases with time; and circulating the perfusion solution out of the bioreactor chamber separately through the dialysis system and the delivery system, and back into the bioreactor chamber;

wherein at least 90% of a volume of the perfusion solution that exits the bioreactor chamber is circulated back into the bioreactor chamber during an entire growth period of the cells.

19. The method according to claim 17, wherein the cells form a suspension cell culture, and wherein the computerized controller is configured to maintain at least 95% of cells forming the suspension cell culture in the bioreactor chamber.

20. An in-vitro method of generating an adipocyte cell from the system of claim 1, comprising:

culturing in the bioreactor chamber a spontaneously immortalized fibroblast in a serum-free medium, comprising oleic acid and a PPAR-gamma agonist or activator, thereby generating the adipocyte cell.

21. The method of claim 20, wherein the spontaneously immortalized fibroblast is an avian fibroblast.

22. The method of claim 20, wherein the spontaneously immortalized fibroblast is a chicken embryonic fibroblast.

23. The method of claim 20, wherein the spontaneously immortalized fibroblast is non-genetically modified.

24. The method of claim 20, wherein the PPAR-gamma agonist or activator is a small molecule.

25. The method of claim 20, wherein the serum-free medium is devoid of animal contaminants.

26. The method of claim 20, wherein the serum-free medium is devoid of human contaminants.

27. The method of claim 20, wherein the serum-free medium comprises insulin or a substitute thereof, and basic fibroblast growth factor (bFGF) or a substitute thereof, and at least one additional agent selected from the group consisting of dexamethasone, transferrin, selenium, EGF or a substitute thereof, and PGE2.

28. An adipocyte obtainable according to the method of claim 20.

29. A method of generating a cultured fat on a plant-derived protein matrix, comprising: generating the adipocyte cell from the fibroblast according to the method of claim 20, wherein the culturing is performed on the plant-derived protein matrix, thereby generating the cultured fat on the plant-derived protein matrix.

* * * * *

SEQUENCE LISTING

```
<160> NUMBER OF SEQ ID NOS: 22

<210> SEQ ID NO 1
<211> LENGTH: 10975
<212> TYPE: DNA
<213> ORGANISM: Artificial sequence
<220> FEATURE:
<223> OTHER INFORMATION: pInducer20-cMyoD1

<400> SEQUENCE: 1

tggaagggct aattcactcc caaagaagac aagatatcct tgatctgtgg atctaccaca     60

cacaaggcta cttccctgat tagcagaact acacaccagg gccaggggtc agatatccac    120

tgacctttgg atggtgctac aagctagtac cagttgagcc agataaggta gaagaggcca    180

ataaaggaga gaacaccagc ttgttacacc ctgtgagcct gcatgggatg gatgacccgg    240

agagagaagt gttagagtgg aggtttgaca gccgcctagc atttcatcac gtggcccgag    300

agctgcatcc ggagtacttc aagaactgct gatatcgagc ttgctacaag ggactttccg    360

ctggggactt tccagggagg cgtggcctgg gcgggactgg ggagtggcga gccctcagat    420

cctgcatata agcagctgct ttttgcctgt actgggtctc tctggttaga ccagatctga    480

gcctgggagc tctctggcta actagggaac ccactgctta agcctcaata aagcttgcct    540

tgagtgcttc aagtagtgtg tgcccgtctg ttgtgtgact ctggtaacta gagatccctc    600

agaccctttt agtcagtgtg gaaaatctct agcagtggcg cccgaacagg gacttgaaag    660

cgaaagggaa accagaggag ctctctcgac gcaggactcg gcttgctgaa gcgcgcacgg    720

caagaggcga ggggcggcga ctggtgagta cgccaaaaat tttgactagc ggaggctaga    780

aggagagaga tgggtgcgag agcgtcagta ttaagcgggg gagaattaga tcgcgatggg    840

aaaaaattcg gttaaggcca gggggaaaga aaaaatataa attaaaacat atagtatggg    900

caagcaggga gctagaacga ttcgcagtta atcctggcct gttagaaaca tcagaaggct    960

gtagacaaat actgggacag ctacaaccat cccttcagac aggatcagaa gaacttagat   1020

cattatataa tacagtagca accctctatt gtgtgcatca aaggatagag ataaaagaca   1080

ccaaggaagc tttagacaag atagaggaag agcaaaacaa aagtaagacc accgcacagc   1140

aagcggccgg ccgctgatct tcagacctgg aggaggagat atgagggaca attggagaag   1200

tgaattatat aaatataaag tagtaaaaat tgaaccatta ggagtagcac ccaccaaggc   1260

aaagagaaga gtggtgcaga gagaaaaaag agcagtggga ataggagctt tgttccttgg   1320

gttcttggga gcagcaggaa gcactatggg cgcagcgtca atgacgctga cggtacaggc   1380
```

-continued

```
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaaagaaaa ggggggattg gggggtacag tgcaggggaa   2100
agaatagtag acataatagc aacagacata caaactaaag aattacaaaa acaaattaca   2160
aaaattcaaa attttcgggt ttattacagg gacagcagag atccagtttg gactaggatc   2220
ctttaccact ccctatcagt gatagagaaa agtgaaagtc gagtttacca ctccctatca   2280
gtgatagaga aaagtgaaag tcgagtttac cactccctat cagtgataga gaaaagtgaa   2340
agtcgagttt accactccct atcagtgata gagaaaagtg aaagtcgagt ttaccactcc   2400
ctatcagtga tagagaaaag tgaaagtcga gtttaccact ccctatcagt gatagagaaa   2460
agtgaaagtc gagtttacca ctccctatca gtgatagaga aaagtgaaag tcgagctcgg   2520
tacccgggtc gaggtaggcg tgtacggtgg gaggcctata taagcagagc tcgtttagtg   2580
aaccgtcaga tcgcctggag acgccatcca cgctgttttg acctccatag aagacaccgg   2640
gaccgatcca gcctccgcgg ccccgaacta gtccagtgtg gtgggtcgag actagcgcta   2700
gcatggacct tttgggaccg atggaaatga ctgagggttc tctctgttct tttaccgctg   2760
cggatgattt ctatgatgac ccctgtttca acacgagcga tatgcacttt ttcgaagatc   2820
tggaccccag gctcgtccac gttggcggtc ttctgaaagc cgaagaacat cctcatcatc   2880
atgggcacca tcatggtaat cctcatgagg aggagcatgt aagggccccc agcggtcatc   2940
atcaggccgg taggtgcctg ctttgggcgt gcaaggcttg caaaaggaaa acaactaatg   3000
ctgaccggcg gaaagcagcc acgatgcgcg aacgccgcag gttgtctaaa gtcaacgaag   3060
cattcgagac gcttaagcgg tgtacaagta ctaatccaaa ccagaggctc cccaaagttg   3120
aaatccttcg gaatgcaatt cggtatatcg aaagcctgca agcgctgctc cgggaacaag   3180
aagacgcata ttaccccgtc ctcgaacact actctggaga aagtgacgcc tccagcccac   3240
gcagtaactg ctccgacggg atgatggaat attctggacc accgtgctct agccggcgca   3300
gaaattcata cgactcctct tactacacag agagcccgaa tgatccgaag cacgggaagt   3360
ctagcgtggt ctcttcactg gattgtctca gtagcattgt cgagcgcatc agtactgaca   3420
actccacctg cccgatattg ccgcccgccg aagctgttgc tgagggcagt ccatgtagcc   3480
cccaggaggg gggaaatctt tctgactccg gggctcaaat tccatccccg accaactgta   3540
ccccactgcc gcaggaatct agctccagta gttcaagcaa cccgatatat caagttcttt   3600
agtcgacgtc gagtctagag ggcccgcggt tcgaataccc atacgacgtc ccagactacg   3660
cttagtaatg attaattaaa ctagaaattc taccgggtag ggaggcgct tttcccaagg   3720
```

-continued

```
cagtctggag taacccaccc aagatctggc ctccgcgccg ggttttggcg cctcccgcgg   3780
gcgcccccct cctcacggcg agcgctgcca cgtcagacga agggcgcagc gagcgtcctg   3840
atccttccgc ccggacgctc aggacagcgg cccgctgctc ataagactcg gccttagaac   3900
cccagtatca gcagaaggac attttaggac gggacttggg tgactctagg gcactggttt   3960
tctttccaga gagcggaaca ggcgaggaaa agtagtccct tctcggcgat tctgcggagg   4020
gatctccgtg gggcggtgaa cgccgatgat tatataagga cgcgccgggt gtggcacagc   4080
tagttccgtc gcagccggga tttgggtcgc ggttcttgtt tgtggatcgc tgtgatcgtc   4140
acttggtgag tagcgggctg ctgggctggc cggggctttc gtggccgccg ggccgctcgg   4200
tgggacggaa gcgtgtggag agaccgccaa gggctgtagt ctgggtccgc gagcaaggtt   4260
gccctgaact gggggttggg gggagcgcag caaaatggcg gctgttcccg agtcttgaat   4320
ggaagacgct tgtgaggcgg gctgtgaggt cgttgaaaca aggtgggggg catggtgggc   4380
ggcaagaacc caaggtcttg aggccttcgc taatgcggga aagctcttat tcgggtgaga   4440
tgggctgggg caccatctgg ggaccctgac gtgaagtttg tcactgactg gagaactcgg   4500
tttgtcgtct gttgcggggg cggcagttat ggcggtgccg ttgggcagtg cacccgtacc   4560
tttgggagcg cgcgccctcg tcgtgtcgtg acgtcacccg ttctgttggc ttataatgca   4620
gggtggggcc acctgccggt aggtgtgcgg taggcttttc tccgtcgcag gacgcagggt   4680
tcgggcctag ggtaggctct cctgaatcga caggcgccgg acctctggtg aggggaggga   4740
taagtgaggc gtcagtttct ttggtcggtt ttatgtacct atcttcttaa gtagctgaag   4800
ctccggtttt gaactatgcg ctcggggttg gcgagtgtgt tttgtgaagt tttttaggca   4860
ccttttgaaa tgtaatcatt tgggtcaata tgtaattttc agtgttagac tagtaaattg   4920
tccgctaaat tctggccgtt tttggctttt ttgttagacg aagcttggta ccgagctcgg   4980
atctccaccc cgtaccggtc ctgcagtcga attcaccatg tctagactgg acaagagcaa   5040
agtcataaac ggagctctgg aattactcaa tggtgtcggt atcgaaggcc tgacgacaag   5100
gaaactcgct caaaagctgg gagttgagca gcctaccctg tactggcacg tgaagaacaa   5160
gcgggccctg ctcgatgccc tgccaatcga gatgctggac aggcatcata cccacttctg   5220
cccccctggaa ggcgagtcat ggcaagactt tctgcggaac aacgccaagt cataccgctg   5280
tgctctcctc tcacatcgcg acggggctaa agtgcatctc ggcacccgcc caacagagaa   5340
acagtacgaa accctggaaa atcagctcgc gttcctgtgt cagcaaggct tctccctgga   5400
gaacgcactg tacgctctgt ccgccgtggg ccactttaca ctgggctgcg tattggagga   5460
acaggagcat caagtagcaa aagaggaaag agagacacct accaccgatt ctatgccccc   5520
acttctgaga caagcaattg agctgttcga ccggcaggga gccgaacctg ccttcctttt   5580
cggcctggaa ctaatcatat gtggcctgga gaaacagcta aagtgcgaaa gcggcgggcc   5640
gaccgacgcc cttgacgatt ttgacttaga catgctccca gccgatgccc ttgacgactt   5700
tgaccttgat atgctgcctg ctgacgctct tgacgatttt gaccttgaca tgctccccgg   5760
gtaactaagt aaggatccgc ggccgcacta gaggaattcc gcccctctcc ctcccccccc   5820
cctaacgtta ctggccgaag ccgcttggaa taaggccggt gtgtgtttgt ctatatgtta   5880
ttttccacca tattgccgtc ttttggcaat gtgagggccc ggaaacctgg ccctgtcttc   5940
ttgacgagca ttcctagggg tctttcccct ctcgccaaag gaatgcaagg tctgttgaat   6000
gtcgtgaagg aagcagttcc tctggaagct tcttgaagac aaacaacgtc tgtagcgacc   6060
ctttgcaggc agcggaaccc cccacctggc gacaggtgcc tctgcggcca aaagccacgt   6120
```

-continued

```
gtataagata cacctgcaaa ggcggcacaa ccccagtgcc acgttgtgag ttggatagtt   6180
gtggaaagag tcaaatggct ctcctcaagc gtagtcaaca aggggctgaa ggatgcccag   6240
aaggtacccc attgtatggg aatctgatct ggggcctcgg tgcacatgct ttacatgtgt   6300
ttagtcgagg ttaaaaaaac gtctaggccc cccgaaccac ggggacgtgg ttttcctttg   6360
aaaaacacga tgataagctt accggtccac catgattgaa caagatggat tgcacgcagg   6420
ttctccggcc gcttgggtgg agaggctatt cggctatgac tgggcacaac agacaatcgg   6480
ctgctctgat gccgccgtgt tccggctgtc agcgcagggg cgcccggttc tttttgtcaa   6540
gaccgacctg tccggtgccc tgaatgaact gcaagacgag gcagcgcggc tatcgtggct   6600
ggccacgacg ggcgttcctt gcgcagctgt gctcgacgtt gtcactgaag cgggaaggga   6660
ctggctgcta ttgggcgaag tgccggggca ggatctcctg tcatctcacc ttgctcctgc   6720
cgagaaagta tccatcatgg ctgatgcaat gcggcggctg catacgcttg atccggctac   6780
ctgcccattc gaccaccaag cgaaacatcg catcgagcga gcacgtactc ggatggaagc   6840
cggtcttgtc gatcaggatg atctggacga agagcatcag gggctcgcgc cagccgaact   6900
gttcgccagg ctcaaggcga gcatgcccga cggcgaggat ctcgtcgtga cccatggcga   6960
tgcctgcttg ccgaatatca tggtggaaaa tggccgcttt tctggattca tcgactgtgg   7020
ccggctgggt gtggcggacc gctatcagga catagcgttg gctacccgtg atattgctga   7080
agagcttggc ggcgaatggg ctgaccgctt cctcgtgctt tacggtatcg ccgctcccga   7140
ttcgcagcgc atcgccttct atcgccttct tgacgagttc ttctgatgta caagtaaagc   7200
ggccgcgact ctagatcata atcagccata ccacatttgt agaggtttta cttgctttaa   7260
aaaacctccc acacctcccc ctgaacctga aacataaaat gaatgcaatt gttgttgttt   7320
agtccctccc aattcgatat caagcttatc gatcgataga tcctaatcaa cctctggatt   7380
acaaaatttg tgaaagattg actggtattc ttaactatgt tgctcctttt acgctatgtg   7440
gatacgctgc tttaatgcct ttgtatcatg ctattgcttc ccgtatggct ttcattttct   7500
cctccttgta taaatcctgg ttgctgtctc tttatgagga gttgtggccc gttgtcaggc   7560
aacgtggcgt ggtgtgcact gtgtttgctg acgcaacccc cactggttgg ggcattgcca   7620
ccacctgtca gctcctttcc gggactttcg ctttcccct ccctattgcc acggcggaac    7680
tcatcgccgc ctgccttgcc cgctgctgga caggggctcg gctgttgggc actgacaatt   7740
ccgtggtgtt gtcggggaaa tcatcgtcct ttccttggct gctcgcctgt gttgccacct   7800
ggattctgcg cgggacgtcc ttctgctacg tcccttcggc cctcaatcca gcggaccttc   7860
cttcccgcgg cctgctgccg gctctgcggc ctcttccgcg tcttcgcctt cgccctcaga   7920
cgagtcggat ctccctttgg gccgcctccc cgcctgagat cctttaagac caatgactta   7980
caaggcagct gtagatctta gccacttttt aaaagaaaag gggggactgg aagggctaat   8040
tcactcccaa cgaagacaag atctgctttt tgcttgtact gggtctctct ggttagacca   8100
gatctgagcc tgggagctct ctggctaact agggaaccca ctgcttaagc ctcaataaag   8160
cttgccttga gtgcttcaag tagtgtgtgc ccgtctgttg tgtgactctg gtaactagag   8220
atccctcaga cccttttagt cagtgtggaa aatctctagc agtagtagtt catgtcatct   8280
tattattcag tatttataac ttgcaaagaa atgaatatca gagagtgaga ggcccgggtt   8340
aattaaggaa agggctagat cattcttgaa gacgaaaggg cctcgtgata cgcctatttt   8400
tataggttaa tgtcatgata ataatggttt cttagacgtc aggtggcact tttcggggaa   8460
```

-continued

```
atgtgcgcgg aacccctatt tgtttatttt tctaaataca ttcaaatatg tatccgctca   8520
tgagacaata accctgataa atgcttcaat aatattgaaa aaggaagagt atgagtattc   8580
aacatttccg tgtcgccctt attccctttt ttgcggcatt ttgccttcct gtttttgctc   8640
acccagaaac gctggtgaaa gtaaaagatg ctgaagatca gttgggtgca cgagtgggtt   8700
acatcgaact ggatctcaac agcggtaaga tccttgagag ttttcgcccc gaagaacgtt   8760
ttccaatgat gagcactttt aaagttctgc tatgtggcgc ggtattatcc cgtgttgacg   8820
ccgggcaaga gcaactcggt cgccgcatac actattctca gaatgacttg gttgagtact   8880
caccagtcac agaaaagcat cttacggatg gcatgacagt aagagaatta tgcagtgctg   8940
ccataaccat gagtgataac actgcggcca acttacttct gacaacgatc ggaggaccga   9000
aggagctaac cgcttttttg cacaacatgg gggatcatgt aactcgcctt gatcgttggg   9060
aaccggagct gaatgaagcc ataccaaacg acgagcgtga caccacgatg cctgtagcaa   9120
tggcaacaac gttgcgcaaa ctattaactg gcgaactact tactctagct tcccggcaac   9180
aattaataga ctggatggag gcggataaag ttgcaggacc acttctgcgc tcggcccttc   9240
cggctggctg gtttattgct gataaatctg gagccggtga gcgtgggtct cgcggtatca   9300
ttgcagcact ggggccagat ggtaagccct cccgtatcgt agttatctac acgacgggga   9360
gtcaggcaac tatggatgaa cgaaatagac agatcgctga gataggtgcc tcactgatta   9420
agcattggta actgtcagac caagtttact catatatact ttagattgat ttaaaacttc   9480
atttttaatt taaaaggatc taggtgaaga tcctttttga taatctcatg accaaaatcc   9540
cttaacgtga gttttcgttc cactgagcgt cagaccccgt agaaaagatc aaaggatctt   9600
cttgagatcc tttttttctg cgcgtaatct gctgcttgca aacaaaaaaa ccaccgctac   9660
cagcggtggt ttgtttgccg gatcaagagc taccaactct ttttccgaag gtaactggct   9720
tcagcagagc gcagatacca aatactgttc ttctagtgta gccgtagtta ggccaccact   9780
tcaagaactc tgtagcaccg cctacatacc tcgctctgct aatcctgtta ccagtggctg   9840
ctgccagtgg cgataagtcg tgtcttaccg ggttggactc aagacgatag ttaccggata   9900
aggcgcagcg gtcgggctga acggggggtt cgtgcacaca gcccagcttg gagcgaacga   9960
cctacaccga actgagatac ctacagcgtg agctatgaga aagcgccacg cttcccgaag  10020
ggagaaaggc ggacaggtat ccggtaagcg gcagggtcgg aacaggagag cgcacgaggg  10080
agcttccagg gggaaacgcc tggtatcttt atagtcctgt cgggtttcgc cacctctgac  10140
ttgagcgtcg atttttgtga tgctcgtcag gggggcggag cctatggaaa aacgccagca  10200
acgcggcctt tttacggttc ctggcctttt gctggccttt tgctcacatg ttctttcctg  10260
cgttatcccc tgattctgtg gataaccgta ttaccgcctt tgagtgagct gataccgctc  10320
gccgcagccg aacgaccgag cgcagcgagt cagtgagcga ggaagcggaa gagcgcccaa  10380
tacgcaaacc gcctctcccc gcgcgttggc cgattcatta atgcagcaag ctcatggctg  10440
actaattttt tttatttatg cagaggccga ggccgcctcg gcctctgagc tattccagaa  10500
gtagtgagga ggcttttttg gaggcctagg cttttgcaaa aagctccccg tggcacgaca  10560
ggtttcccga ctggaaagcg ggcagtgagc gcaacgcaat taatgtgagt tagctcactc  10620
attaggcacc ccaggcttta cactttatgc ttccggctcg tatgttgtgt ggaattgtga  10680
gcggataaca atttcacaca ggaaacagct atgacatgat tacgaatttc acaaataaag  10740
catttttttc actgcattct agttgtggtt tgtccaaact catcaatgta tcttatcatg  10800
tctggatcaa ctggataact caagctaacc aaaatcatcc caaacttccc accccatacc  10860
```

-continued ctattaccac tgccaattac ctgtggtttc atttactcta aacctgtgat tcctctgaat 10920
tattttcatt ttaaagaaat tgtatttgtt aaatatgtac tacaaactta gtagt 10975

<210> SEQ ID NO 2
<211> LENGTH: 10748
<212> TYPE: DNA
<213> ORGANISM: Artificial sequence
<220> FEATURE:
<223> OTHER INFORMATION: pInducer-cMyogenin

<400> SEQUENCE: 2
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300
agctgcatcc ggagtacttc aagaactgct gatatcgagc ttgctacaag ggactttccg 360
ctggggactt tccagggagg cgtggcctgg gcgggactgg ggagtggcga gccctcagat 420
cctgcatata agcagctgct ttttgcctgt actgggtctc tctggttaga ccagatctga 480
gcctgggagc tctctggcta actagggaac ccactgctta agcctcaata aagcttgcct 540
tgagtgcttc aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagggaa accagaggag ctctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcagta ttaagcgggg gagaattaga tcgcgatggg 840
aaaaaattcg gttaaggcca gggggaaaga aaaaatataa attaaaacat atagtatggg 900
caagcaggga gctagaacga ttcgcagtta atcctggcct gttagaaaca tcagaaggct 960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920

-continued

```
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaaagaaaa ggggggattg gggggtacag tgcaggggaa   2100
agaatagtag acataatagc aacagacata caaactaaag aattacaaaa acaaattaca   2160
aaaattcaaa attttcgggt ttattacagg gacagcagag atccagtttg gactaggatc   2220
ctttaccact ccctatcagt gatagagaaa agtgaaagtc gagtttacca ctccctatca   2280
gtgatagaga aaagtgaaag tcgagtttac cactccctat cagtgataga gaaaagtgaa   2340
agtcgagttt accactccct atcagtgata gagaaaagtg aaagtcgagt ttaccactcc   2400
ctatcagtga tagagaaaag tgaaagtcga gtttaccact ccctatcagt gatagagaaa   2460
agtgaaagtc gagtttacca ctccctatca gtgatagaga aaagtgaaag tcgagctcgg   2520
tacccgggtc gaggtaggcg tgtacggtgg gaggcctata taagcagagc tcgtttagtg   2580
aaccgtcaga tcgcctggag acgccatcca cgctgttttg acctccatag aagacaccgg   2640
gaccgatcca gcctccgcgg ccccgaacta gtccagtgtg gtgggtcgag gctagcatgg   2700
agctctttga gaccaaccct tactttttcc cggagcagag gttttacgat ggggaaaact   2760
tcctgggctc ccgcttgcag ggctacgagg cggccgcgtt tcctgagcgt cccgaggtga   2820
ccctgtgccc tgaaagcaga ggggctttgg aggagaagga ctcgacgctg cccgagcact   2880
gccccgggca atgcttgcca tggcttgca aaatctgcaa gcgcaaaacc gtgtccatcg   2940
accggcgtcg ggcggccacg ctgcgggaga agcggaggct gaagaaggtg aacgaagcct   3000
tcgaggctct gaaacgcagc actctgctca accccaacca gcggctgccc aaggtggaga   3060
tcctgcgcag cgccatccag tacatcgagc gcctgcagag cctgctcagc agcctcaacc   3120
agcaggagcg tgagcagagg gagctgcgct accgccccgc tgcaccacaa cctgctgcac   3180
ccagcgagtg cggctctggc agctcatcct gcagccctga gtggagcacc cagctggagt   3240
ttggcaccaa ccccgcagat cacctcctga gcgatgacca ggcagaggac cgcaacctcc   3300
actcgctctc ctccatcgtg gagagcatcg ccgtggagga cgtggccgtg acgttcccag   3360
aggagcgggt ccaaaactga gtcgagtcta gagggcccgc ggttcgaata cccatacgac   3420
gtcccagact acgcttagta atgattaatt aaactagaaa ttctaccggg taggggaggc   3480
gcttttccca aggcagtctg gagtaaccca cccaagatct ggcctccgcg ccgggttttg   3540
gcgcctcccg cgggcgcccc cctcctcacg gcgagcgctg ccacgtcaga cgaagggcgc   3600
agcgagcgtc ctgatccttc cgcccggacg ctcaggacag cggcccgctg ctcataagac   3660
tcggccttag aaccccagta tcagcagaag gacattttag gacgggactt gggtgactct   3720
agggcactgg ttttctttcc agagagcgga acaggcgagg aaaagtagtc ccttctcggc   3780
gattctgcgg agggatctcc gtggggcggt gaacgccgat gattatataa ggacgcgccg   3840
ggtgtggcac agctagttcc gtcgcagccg ggatttgggt cgcggttctt gtttgtggat   3900
cgctgtgatc gtcacttggt gagtagcggg ctgctgggct ggccggggct ttcgtggccg   3960
ccgggccgct cggtgggacg gaagcgtgtg gagagaccgc caagggctgt agtctgggtc   4020
cgcgagcaag gttgccctga actgggggtt ggggggagcg cagcaaaatg gcggctgttc   4080
ccgagtcttg aatggaagac gcttgtgagg cgggctgtga ggtcgttgaa acaaggtggg   4140
gggcatggtg ggcggcaaga acccaaggtc ttgaggcctt cgctaatgcg ggaaagctct   4200
tattcgggtg agatgggctg ggcaccatc tggggaccct gacgtgaagt ttgtcactga   4260
ctggagaact cggtttgtcg tctgttgcgg gggcggcagt tatggcggtg ccgttgggca   4320
```

```
gtgcacccgt acctttggga gcgcgcgccc tcgtcgtgtc gtgacgtcac ccgttctgtt   4380
ggcttataat gcagggtggg gccacctgcc ggtaggtgtg cggtaggctt ttctccgtcg   4440
caggacgcag ggttcgggcc tagggtaggc tctcctgaat cgacaggcgc cggacctctg   4500
gtgaggggag ggataagtga ggcgtcagtt tctttggtcg gttttatgta cctatcttct   4560
taagtagctg aagctccggt tttgaactat gcgctcgggg ttggcgagtg tgttttgtga   4620
agttttttag gcaccttttg aaatgtaatc atttgggtca atatgtaatt ttcagtgtta   4680
gactagtaaa ttgtccgcta aattctggcc gtttttggct tttttgttag acgaagcttg   4740
gtaccgagct cggatctcca ccccgtaccg gtcctgcagt cgaattcacc atgtctagac   4800
tggacaagag caaagtcata aacggagctc tggaattact caatggtgtc ggtatcgaag   4860
gcctgacgac aaggaaactc gctcaaaagc tgggagttga gcagcctacc ctgtactggc   4920
acgtgaagaa caagcgggcc ctgctcgatg ccctgccaat cgagatgctg gacaggcatc   4980
atacccactt ctgccccctg gaaggcgagt catggcaaga ctttctgcgg aacaacgcca   5040
agtcataccg ctgtgctctc ctctcacatc gcgacggggc taaagtgcat ctcggcaccc   5100
gcccaacaga gaaacagtac gaaaccctgg aaaatcagct cgcgttcctg tgtcagcaag   5160
gcttctccct ggagaacgca ctgtacgctc tgtccgccgt gggccacttt acactgggct   5220
gcgtattgga ggaacaggag catcaagtag caaaagagga aagagagaca cctaccaccg   5280
attctatgcc cccacttctg agacaagcaa ttgagctgtt cgaccggcag ggagccgaac   5340
ctgccttcct tttcggcctg gaactaatca tatgtggcct ggagaaacag ctaaagtgcg   5400
aaagcggcgg gccgaccgac gcccttgacg attttgactt agacatgctc ccagccgatg   5460
cccttgacga ctttgacctt gatatgctgc ctgctgacgc tcttgacgat tttgaccttg   5520
acatgctccc cgggtaacta agtaaggatc cgcggccgca ctagaggaat tccgcccctc   5580
tccctccccc ccccctaacg ttactggccg aagccgcttg gaataaggcc ggtgtgtgtt   5640
tgtctatatg ttattttcca ccatattgcc gtcttttggc aatgtgaggg cccggaaacc   5700
tggccctgtc ttcttgacga gcattcctag gggtctttcc cctctcgcca aaggaatgca   5760
aggtctgttg aatgtcgtga aggaagcagt tcctctggaa gcttcttgaa gacaaacaac   5820
gtctgtagcg accctttgca ggcagcggaa ccccccacct ggcgacaggt gcctctgcgg   5880
ccaaaagcca cgtgtataag atacacctgc aaaggcggca caaccccagt gccacgttgt   5940
gagttggata gttgtggaaa gagtcaaatg gctctcctca agcgtagtca acaaggggct   6000
gaaggatgcc cagaaggtac cccattgtat gggaatctga tctggggcct cggtgcacat   6060
gctttacatg tgtttagtcg aggttaaaaa aacgtctagg ccccccgaac cacggggacg   6120
tggttttcct ttgaaaaaca cgatgataag cttaccggtc caccatgatt gaacaagatg   6180
gattgcacgc aggttctccg gccgcttggg tggagaggct attcggctat gactgggcac   6240
aacagacaat cggctgctct gatgccgccg tgttccggct gtcagcgcag gggcgcccgg   6300
ttctttttgt caagaccgac ctgtccggtg ccctgaatga actgcaagac gaggcagcgc   6360
ggctatcgtg gctggccacg acgggcgttc cttgcgcagc tgtgctcgac gttgtcactg   6420
aagcgggaag ggactggctg ctattgggcg aagtgccggg gcaggatctc ctgtcatctc   6480
accttgctcc tgccgagaaa gtatccatca tggctgatgc aatgcggcgg ctgcatacgc   6540
ttgatccggc tacctgccca ttcgaccacc aagcgaaaca tcgcatcgag cgagcacgta   6600
ctcggatgga agccggtctt gtcgatcagg atgatctgga cgaagagcat caggggctcg   6660
```

-continued

```
cgccagccga actgttcgcc aggctcaagg cgagcatgcc cgacggcgag gatctcgtcg   6720
tgacccatgg cgatgcctgc ttgccgaata tcatggtgga aaatggccgc ttttctggat   6780
tcatcgactg tggccggctg ggtgtggcgg accgctatca ggacatagcg ttggctaccc   6840
gtgatattgc tgaagagctt ggcggcgaat gggctgaccg cttcctcgtg ctttacggta   6900
tcgccgctcc cgattcgcag cgcatcgcct tctatcgcct tcttgacgag ttcttctgat   6960
gtacaagtaa agcggccgcg actctagatc ataatcagcc ataccacatt tgtagaggtt   7020
ttacttgctt taaaaaacct cccacacctc cccctgaacc tgaaacataa aatgaatgca   7080
attgttgttg tttagtccct cccaattcga tatcaagctt atcgatcgat agatcctaat   7140
caacctctgg attacaaaat ttgtgaaaga ttgactggta ttcttaacta tgttgctcct   7200
tttacgctat gtggatacgc tgctttaatg cctttgtatc atgctattgc ttcccgtatg   7260
gctttcattt tctcctcctt gtataaatcc tggttgctgt ctctttatga ggagttgtgg   7320
cccgttgtca ggcaacgtgg cgtggtgtgc actgtgtttg ctgacgcaac ccccactggt   7380
tggggcattg ccaccacctg tcagctcctt tccgggactt tcgctttccc cctccctatt   7440
gccacggcgg aactcatcgc cgcctgcctt gcccgctgct ggacaggggc tcggctgttg   7500
ggcactgaca attccgtggt gttgtcgggg aaatcatcgt cctttccttg gctgctcgcc   7560
tgtgttgcca cctggattct gcgcgggacg tccttctgct acgtcccttc ggccctcaat   7620
ccagcggacc ttccttcccg cggcctgctg ccggctctgc ggcctcttcc gcgtcttcgc   7680
cttcgccctc agacgagtcg gatctccctt tgggccgcct ccccgcctga gatcctttaa   7740
gaccaatgac ttacaaggca gctgtagatc ttagccactt tttaaaagaa aaggggggac   7800
tggaagggct aattcactcc caacgaagac aagatctgct ttttgcttgt actgggtctc   7860
tctggttaga ccagatctga gcctgggagc tctctggcta actagggaac ccactgctta   7920
agcctcaata aagcttgcct tgagtgcttc aagtagtgtg tgcccgtctg ttgtgtgact   7980
ctggtaacta gagatccctc agaccctttt agtcagtgtg gaaaatctct agcagtagta   8040
gttcatgtca tcttattatt cagtatttat aacttgcaaa gaaatgaata tcagagagtg   8100
agaggcccgg gttaattaag gaaagggcta gatcattctt gaagacgaaa gggcctcgtg   8160
atacgcctat ttttataggt taatgtcatg ataataatgg tttcttagac gtcaggtggc   8220
acttttcggg gaaatgtgcg cggaacccct atttgtttat ttttctaaat acattcaaat   8280
atgtatccgc tcatgagaca ataaccctga taaatgcttc aataatattg aaaaaggaag   8340
agtatgagta ttcaacattt ccgtgtcgcc cttattccct tttttgcggc attttgcctt   8400
cctgtttttg ctcacccaga aacgctggtg aaagtaaaag atgctgaaga tcagttgggt   8460
gcacgagtgg gttacatcga actggatctc aacagcggta agatccttga gagttttcgc   8520
cccgaagaac gttttccaat gatgagcact tttaaagttc tgctatgtgg cgcggtatta   8580
tcccgtgttg acgccgggca agagcaactc ggtcgccgca tacactattc tcagaatgac   8640
ttggttgagt actcaccagt cacagaaaag catcttacgg atggcatgac agtaagagaa   8700
ttatgcagtg ctgccataac catgagtgat aacactgcgg ccaacttact tctgacaacg   8760
atcggaggac cgaaggagct aaccgctttt ttgcacaaca tgggggatca tgtaactcgc   8820
cttgatcgtt gggaaccgga gctgaatgaa gccataccaa acgacgagcg tgacaccacg   8880
atgcctgtag caatggcaac aacgttgcgc aaactattaa ctggcgaact acttactcta   8940
gcttcccggc aacaattaat agactggatg gaggcggata aagttgcagg accacttctg   9000
cgctcggccc ttccggctgg ctggtttatt gctgataaat ctggagccgg tgagcgtggg   9060
```

tctcgcggta tcattgcagc actggggcca gatggtaagc cctcccgtat cgtagttatc 9120
tacacgacgg ggagtcaggc aactatggat gaacgaaata gacagatcgc tgagataggt 9180
gcctcactga ttaagcattg gtaactgtca gaccaagttt actcatatat actttagatt 9240
gatttaaaac ttcattttta atttaaaagg atctaggtga agatcctttt tgataatctc 9300
atgaccaaaa tcccttaacg tgagttttcg ttccactgag cgtcagaccc cgtagaaaag 9360
atcaaaggat cttcttgaga tccttttttt ctgcgcgtaa tctgctgctt gcaaacaaaa 9420
aaaccaccgc taccagcggt ggtttgtttg ccggatcaag agctaccaac tctttttccg 9480
aaggtaactg gcttcagcag agcgcagata ccaaatactg ttcttctagt gtagccgtag 9540
ttaggccacc acttcaagaa ctctgtagca ccgcctacat acctcgctct gctaatcctg 9600
ttaccagtgg ctgctgccag tggcgataag tcgtgtctta ccgggttgga ctcaagacga 9660
tagttaccgg ataaggcgca gcggtcgggc tgaacggggg gttcgtgcac acagcccagc 9720
ttggagcgaa cgacctacac cgaactgaga tacctacagc gtgagctatg agaaagcgcc 9780
acgcttcccg aagggagaaa ggcggacagg tatccggtaa gcggcagggt cggaacagga 9840
gagcgcacga gggagcttcc agggggaaac gcctggtatc tttatagtcc tgtcgggttt 9900
cgccacctct gacttgagcg tcgatttttg tgatgctcgt caggggggcg gagcctatgg 9960
aaaaacgcca gcaacgcggc ctttttacgg ttcctggcct tttgctggcc ttttgctcac 10020
atgttctttc ctgcgttatc ccctgattct gtggataacc gtattaccgc ctttgagtga 10080
gctgataccg ctcgccgcag ccgaacgacc gagcgcagcg agtcagtgag cgaggaagcg 10140
gaagagcgcc caatacgcaa accgcctctc cccgcgcgtt ggccgattca ttaatgcagc 10200
aagctcatgg ctgactaatt ttttttattt atgcagaggc cgaggccgcc tcggcctctg 10260
agctattcca gaagtagtga ggaggctttt ttggaggcct aggcttttgc aaaaagctcc 10320
ccgtggcacg acaggtttcc cgactggaaa gcgggcagtg agcgcaacgc aattaatgtg 10380
agttagctca ctcattaggc accccaggct ttacacttta tgcttccggc tcgtatgttg 10440
tgtggaattg tgagcggata acaatttcac acaggaaaca gctatgacat gattacgaat 10500
ttcacaaata aagcattttt ttcactgcat tctagttgtg gtttgtccaa actcatcaat 10560
gtatcttatc atgtctggat caactggata actcaagcta accaaaatca tcccaaactt 10620
cccaccccat accctattac cactgccaat tacctgtggt ttcatttact ctaaacctgt 10680
gattcctctg aattattttc attttaaaga aattgtattt gttaaatatg tactacaaac 10740
ttagtagt 10748

<210> SEQ ID NO 3
<211> LENGTH: 11244
<212> TYPE: DNA
<213> ORGANISM: Artificial sequence
<220> FEATURE:
<223> OTHER INFORMATION: pInducer-VP64-cMyoD1

<400> SEQUENCE: 3
tggaagggct aattcactcc caaagaagac aagatatcct tgatctgtgg atctaccaca 60
cacaaggcta cttccctgat tagcagaact acacaccagg gccaggggtc agatatccac 120
tgacctttgg atggtgctac aagctagtac cagttgagcc agataaggta gaagaggcca 180
ataaaggaga gaacaccagc ttgttacacc ctgtgagcct gcatgggatg gatgacccgg 240
agagagaagt gttagagtgg aggtttgaca gccgcctagc atttcatcac gtggcccgag 300

-continued

```
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccgaa ttcacaaatg   2040
gcagtattca tccacaattt taaaagaaaa ggggggattg gggggtacag tgcaggggaa   2100
agaatagtag acataatagc aacagacata caaactaaag aattacaaaa acaaattaca   2160
aaaattcaaa attttcgggt ttattacagg gacagcagag atccagtttg gactaggatc   2220
ctttaccact ccctatcagt gatagagaaa agtgaaagtc gagtttacca ctccctatca   2280
gtgatagaga aaagtgaaag tcgagtttac cactccctat cagtgataga gaaaagtgaa   2340
agtcgagttt accactccct atcagtgata gagaaaagtg aaagtcgagt ttaccactcc   2400
ctatcagtga tagagaaaag tgaaagtcga gtttaccact ccctatcagt gatagagaaa   2460
agtgaaagtc gagtttacca ctccctatca gtgatagaga aaagtgaaag tcgagctcgg   2520
tacccgggtc gaggtaggcg tgtacggtgg gaggcctata taagcagagc tcgtttagtg   2580
aaccgtcaga tcgcctggag acgccatcca cgctgttttg acctccatag aagacaccgg   2640
gaccgatcca gcctccgcgg ccccgaacta gtccagtgtg gtgggtcgag actagcgcta   2700
```

gctgaaaacg tctgggcaag cgggtcaggc atccccgaag aagaaaagga aggtcgggag 2760
agcggacgcg ctcgatgact tcgatttgga catgctcggc tccgatgctc tggatgactt 2820
tgatctggac atgctcggtt cagatgcgct ggatgatttt gatttggata tgctcggaag 2880
cgacgcactc gacgattttg accttgacat gctcatcaat tatccgtatg atgttcccga 2940
ttatgcgtct gggggaagtg gtggggggtc catggacctt ttgggaccga tggaaatgac 3000
tgagggttct ctctgttctt ttaccgctgc ggatgatttc tatgatgacc cctgtttcaa 3060
cacgagcgat atgcactttt tcgaagatct ggaccccagg ctcgtccacg ttggcggtct 3120
tctgaaagcc gaagaacatc ctcatcatca tgggcaccat catggtaatc ctcatgagga 3180
ggagcatgta agggccccca gcggtcatca tcaggccggt aggtgcctgc tttgggcgtg 3240
caaggcttgc aaaaggaaaa caactaatgc tgaccggcgg aaagcagcca cgatgcgcga 3300
acgccgcagg ttgtctaaag tcaacgaagc attcgagacg cttaagcggt gtacaagtac 3360
taatccaaac cagaggctcc ccaaagttga aatccttcgg aatgcaattc ggtatatcga 3420
aagcctgcaa gcgctgctcc gggaacaaga agacgcatat taccccgtcc tcgaacacta 3480
ctctggagaa agtgacgcct ccagcccacg cagtaactgc tccgacggga tgatggaata 3540
ttctggacca ccgtgctcta gccggcgcag aaattcatac gactcctctt actacacaga 3600
gagcccgaat gatccgaagc acgggaagtc tagcgtggtc tcttcactgg attgtctcag 3660
tagcattgtc gagcgcatca gtactgacaa ctccacctgc ccgatattgc cgcccgccga 3720
agctgttgct gagggcagtc catgtagccc ccaggagggg ggaaatcttt ctgactccgg 3780
ggctcaaatt ccatccccga ccaactgtac cccactgccg caggaatcta gctccagtag 3840
ttcaagcaac ccgatatatc aagttcttta gtcgacgtcg agtctagagg gcccgcggtt 3900
cgaataccca tacgacgtcc cagactacgc ttagtaatga ttaattaaac tagaaattct 3960
accgggtagg ggaggcgctt ttcccaaggc agtctggagt aacccaccca agatctggcc 4020
tccgcgccgg gttttggcgc ctcccgcggg cgcccccctc ctcacggcga gcgctgccac 4080
gtcagacgaa gggcgcagcg agcgtcctga tccttccgcc cggacgctca ggacagcggc 4140
ccgctgctca taagactcgg ccttagaacc ccagtatcag cagaaggaca ttttaggacg 4200
ggacttgggt gactctaggg cactggtttt ctttccagag agcggaacag gcgaggaaaa 4260
gtagtccctt ctcggcgatt ctgcggaggg atctccgtgg ggcggtgaac gccgatgatt 4320
atataaggac gcgccgggtg tggcacagct agttccgtcg cagccgggat ttgggtcgcg 4380
gttcttgttt gtggatcgct gtgatcgtca cttggtgagt agcgggctgc tgggctggcc 4440
ggggctttcg tggccgccgg gccgctcggt gggacggaag cgtgtggaga gaccgccaag 4500
ggctgtagtc tgggtccgcg agcaaggttg ccctgaactg ggggttgggg ggagcgcagc 4560
aaaatggcgg ctgttcccga gtcttgaatg gaagacgctt gtgaggcggg ctgtgaggtc 4620
gttgaaacaa ggtggggggc atggtgggcg gcaagaaccc aaggtcttga ggccttcgct 4680
aatgcgggaa agctcttatt cgggtgagat gggctggggc accatctggg gaccctgacg 4740
tgaagtttgt cactgactgg agaactcggt ttgtcgtctg ttgcgggggc ggcagttatg 4800
gcggtgccgt tgggcagtgc acccgtacct ttgggagcgc gcgccctcgt cgtgtcgtga 4860
cgtcacccgt tctgttggct tataatgcag ggtggggcca cctgccggta ggtgtgcggt 4920
aggcttttct ccgtcgcagg acgcagggtt cgggcctagg gtaggctctc ctgaatcgac 4980
aggcgccgga cctctggtga ggggagggat aagtgaggcg tcagtttctt tggtcggttt 5040

-continued

```
tatgtaccta tcttcttaag tagctgaagc tccggttttg aactatgcgc tcggggttgg   5100
cgagtgtgtt ttgtgaagtt ttttaggcac cttttgaaat gtaatcattt gggtcaatat   5160
gtaattttca gtgttagact agtaaattgt ccgctaaatt ctggccgttt ttggcttttt   5220
tgttagacga agcttggtac cgagctcgga tctccacccc gtaccggtcc tgcagtcgaa   5280
ttcaccatgt ctagactgga caagagcaaa gtcataaacg gagctctgga attactcaat   5340
ggtgtcggta tcgaaggcct gacgacaagg aaactcgctc aaaagctggg agttgagcag   5400
cctaccctgt actggcacgt gaagaacaag cgggccctgc tcgatgccct gccaatcgag   5460
atgctggaca ggcatcatac ccacttctgc cccctggaag gcgagtcatg gcaagacttt   5520
ctgcggaaca acgccaagtc ataccgctgt gctctcctct cacatcgcga cggggctaaa   5580
gtgcatctcg gcacccgccc aacagagaaa cagtacgaaa ccctggaaaa tcagctcgcg   5640
ttcctgtgtc agcaaggctt ctccctggag aacgcactgt acgctctgtc cgccgtgggc   5700
cactttacac tgggctgcgt attggaggaa caggagcatc aagtagcaaa agaggaaaga   5760
gagacaccta ccaccgattc tatgccccca cttctgagac aagcaattga gctgttcgac   5820
cggcagggag ccgaacctgc cttccttttc ggcctggaac taatcatatg tggcctggag   5880
aaacagctaa agtgcgaaag cggcgggccg accgacgccc ttgacgattt tgacttagac   5940
atgctcccag ccgatgccct tgacgacttt gaccttgata tgctgcctgc tgacgctctt   6000
gacgattttg accttgacat gctccccggg taactaagta aggatccgcg gccgcactag   6060
aggaattccg cccctctccc tcccccccc ctaacgttac tggccgaagc cgcttggaat   6120
aaggccggtg tgtgtttgtc tatatgttat tttccaccat attgccgtct tttggcaatg   6180
tgagggcccg gaaacctggc cctgtcttct tgacgagcat tcctaggggt ctttcccctc   6240
tcgccaaagg aatgcaaggt ctgttgaatg tcgtgaagga agcagttcct ctggaagctt   6300
cttgaagaca aacaacgtct gtagcgaccc tttgcaggca gcggaacccc ccacctggcg   6360
acaggtgcct ctgcggccaa aagccacgtg tataagatac acctgcaaag gcggcacaac   6420
cccagtgcca cgttgtgagt tggatagttg tggaaagagt caaatggctc tcctcaagcg   6480
tagtcaacaa ggggctgaag gatgcccaga aggtacccca ttgtatggga atctgatctg   6540
gggcctcggt gcacatgctt tacatgtgtt tagtcgaggt taaaaaaacg tctaggcccc   6600
ccgaaccacg gggacgtggt tttcctttga aaaacacgat gataagctta ccggtccacc   6660
atgattgaac aagatggatt gcacgcaggt tctccggccg cttgggtgga gaggctattc   6720
ggctatgact gggcacaaca gacaatcggc tgctctgatg ccgccgtgtt ccggctgtca   6780
gcgcaggggc gcccggttct ttttgtcaag accgacctgt ccggtgccct gaatgaactg   6840
caagacgagg cagcgcggct atcgtggctg gccacgacgg gcgttccttg cgcagctgtg   6900
ctcgacgttg tcactgaagc gggaagggac tggctgctat tgggcgaagt gccggggcag   6960
gatctcctgt catctcacct tgctcctgcc gagaaagtat ccatcatggc tgatgcaatg   7020
cggcggctgc atacgcttga tccggctacc tgcccattcg accaccaagc gaaacatcgc   7080
atcgagcgag cacgtactcg gatggaagcc ggtcttgtcg atcaggatga tctggacgaa   7140
gagcatcagg ggctcgcgcc agccgaactg ttcgccaggc tcaaggcgag catgcccgac   7200
ggcgaggatc tcgtcgtgac ccatggcgat gcctgcttgc cgaatatcat ggtggaaaat   7260
ggccgctttt ctggattcat cgactgtggc cggctgggtg tggcggaccg ctatcaggac   7320
atagcgttgg ctacccgtga tattgctgaa gagcttggcg gcgaatgggc tgaccgcttc   7380
ctcgtgcttt acggtatcgc cgctcccgat tcgcagcgca tcgccttcta tcgccttctt   7440
```

-continued

```
gacgagttct tctgatgtac aagtaaagcg gccgcgactc tagatcataa tcagccatac   7500
cacatttgta gaggttttac ttgctttaaa aaacctccca cacctccccc tgaacctgaa   7560
acataaaatg aatgcaattg ttgttgttta gtccctccca attcgatatc aagcttatcg   7620
atcgatagat cctaatcaac ctctggatta caaaatttgt gaaagattga ctggtattct   7680
taactatgtt gctcctttta cgctatgtgg atacgctgct ttaatgcctt tgtatcatgc   7740
tattgcttcc cgtatggctt tcattttctc ctccttgtat aaatcctggt tgctgtctct   7800
ttatgaggag ttgtggcccg ttgtcaggca acgtggcgtg gtgtgcactg tgtttgctga   7860
cgcaaccccc actggttggg gcattgccac cacctgtcag ctcctttccg ggactttcgc   7920
tttccccctc cctattgcca cggcggaact catcgccgcc tgccttgccc gctgctggac   7980
aggggctcgg ctgttgggca ctgacaattc cgtggtgttg tcggggaaat catcgtcctt   8040
tccttggctg ctcgcctgtg ttgccacctg gattctgcgc gggacgtcct tctgctacgt   8100
cccttcggcc ctcaatccag cggaccttcc ttcccgcggc ctgctgccgg ctctgcggcc   8160
tcttccgcgt cttcgccttc gccctcagac gagtcggatc tccctttggg ccgcctcccc   8220
gcctgagatc ctttaagacc aatgacttac aaggcagctg tagatcttag ccacttttta   8280
aaagaaaagg ggggactgga agggctaatt cactcccaac gaagacaaga tctgcttttt   8340
gcttgtactg ggtctctctg gttagaccag atctgagcct gggagctctc tggctaacta   8400
gggaacccac tgcttaagcc tcaataaagc ttgccttgag tgcttcaagt agtgtgtgcc   8460
cgtctgttgt gtgactctgg taactagaga tccctcagac ccttttagtc agtgtggaaa   8520
atctctagca gtagtagttc atgtcatctt attattcagt atttataact tgcaaagaaa   8580
tgaatatcag agagtgagag gcccgggtta attaaggaaa gggctagatc attcttgaag   8640
acgaaagggc ctcgtgatac gcctattttt ataggttaat gtcatgataa taatggtttc   8700
ttagacgtca ggtggcactt ttcggggaaa tgtgcgcgga acccctattt gtttattttt   8760
ctaaatacat tcaaatatgt atccgctcat gagacaataa ccctgataaa tgcttcaata   8820
atattgaaaa aggaagagta tgagtattca acatttccgt gtcgccctta ttcccttttt   8880
tgcggcattt tgccttcctg tttttgctca cccagaaacg ctggtgaaag taaaagatgc   8940
tgaagatcag ttgggtgcac gagtgggtta catcgaactg gatctcaaca gcggtaagat   9000
ccttgagagt tttcgccccg aagaacgttt tccaatgatg agcactttta aagttctgct   9060
atgtggcgcg gtattatccc gtgttgacgc cgggcaagag caactcggtc gccgcataca   9120
ctattctcag aatgacttgg ttgagtactc accagtcaca gaaaagcatc ttacggatgg   9180
catgacagta agagaattat gcagtgctgc cataaccatg agtgataaca ctgcggccaa   9240
cttacttctg acaacgatcg gaggaccgaa ggagctaacc gcttttttgc acaacatggg   9300
ggatcatgta actcgccttg atcgttggga accggagctg aatgaagcca taccaaacga   9360
cgagcgtgac accacgatgc ctgtagcaat ggcaacaacg ttgcgcaaac tattaactgg   9420
cgaactactt actctagctt cccggcaaca attaatagac tggatggagg cggataaagt   9480
tgcaggacca cttctgcgct cggcccttcc ggctggctgg tttattgctg ataaatctgg   9540
agccggtgag cgtgggtctc gcggtatcat tgcagcactg gggccagatg gtaagccctc   9600
ccgtatcgta gttatctaca cgacggggag tcaggcaact atggatgaac gaaatagaca   9660
gatcgctgag ataggtgcct cactgattaa gcattggtaa ctgtcagacc aagtttactc   9720
atatatactt tagattgatt taaaacttca tttttaattt aaaaggatct aggtgaagat   9780
```

cctttttgat aatctcatga ccaaaatccc ttaacgtgag ttttcgttcc actgagcgtc 9840
agaccccgta gaaaagatca aaggatcttc ttgagatcct ttttttctgc gcgtaatctg 9900
ctgcttgcaa acaaaaaaac caccgctacc agcggtggtt tgtttgccgg atcaagagct 9960
accaactctt tttccgaagg taactggctt cagcagagcg cagataccaa atactgttct 10020
tctagtgtag ccgtagttag gccaccactt caagaactct gtagcaccgc ctacatacct 10080
cgctctgcta atcctgttac cagtggctgc tgccagtggc gataagtcgt gtcttaccgg 10140
gttggactca agacgatagt taccggataa ggcgcagcgg tcgggctgaa cggggggttc 10200
gtgcacacag cccagcttgg agcgaacgac ctacaccgaa ctgagatacc tacagcgtga 10260
gctatgagaa agcgccacgc ttcccgaagg gagaaaggcg gacaggtatc cggtaagcgg 10320
cagggtcgga acaggagagc gcacgaggga gcttccaggg ggaaacgcct ggtatcttta 10380
tagtcctgtc gggtttcgcc acctctgact tgagcgtcga tttttgtgat gctcgtcagg 10440
ggggcggagc ctatggaaaa acgccagcaa cgcggccttt ttacggttcc tggccttttg 10500
ctggcctttt gctcacatgt tctttcctgc gttatcccct gattctgtgg ataaccgtat 10560
taccgccttt gagtgagctg ataccgctcg ccgcagccga acgaccgagc gcagcgagtc 10620
agtgagcgag gaagcggaag agcgcccaat acgcaaaccg cctctccccg cgcgttggcc 10680
gattcattaa tgcagcaagc tcatggctga ctaatttttt ttatttatgc agaggccgag 10740
gccgcctcgg cctctgagct attccagaag tagtgaggag gcttttttgg aggcctaggc 10800
ttttgcaaaa agctccccgt ggcacgacag gtttcccgac tggaaagcgg gcagtgagcg 10860
caacgcaatt aatgtgagtt agctcactca ttaggcaccc caggctttac actttatgct 10920
tccggctcgt atgttgtgtg gaattgtgag cggataacaa tttcacacag gaaacagcta 10980
tgacatgatt acgaatttca caaataaagc atttttttca ctgcattcta gttgtggttt 11040
gtccaaactc atcaatgtat cttatcatgt ctggatcaac tggataactc aagctaacca 11100
aaatcatccc aaacttccca ccccataccc tattaccact gccaattacc tgtggtttca 11160
tttactctaa acctgtgatt cctctgaatt attttcattt taaagaaatt gtatttgtta 11220
aatatgtact acaaacttag tagt 11244

<210> SEQ ID NO 4
<211> LENGTH: 11109
<212> TYPE: DNA
<213> ORGANISM: Artificial sequence
<220> FEATURE:
<223> OTHER INFORMATION: rat MLC3 enhancer-promoter in pGreenfire lentiviral vector

<400> SEQUENCE: 4
acgcgtgtag tcttatgcaa tactcttgta gtcttgcaac atggtaacga tgagttagca 60
acatgcctta caaggagaga aaaagcaccg tgcatgccga ttggtggaag taaggtggta 120
cgatcgtgcc ttattaggaa ggcaacagac gggtctgaca tggattggac gaaccactga 180
attgccgcat tgcagagata ttgtatttaa gtgcctagct cgatacaata aacgggtctc 240
tctggttaga ccagatctga gcctgggagc tctctggcta actagggaac ccactgctta 300
agcctcaata aagcttgcct tgagtgcttc aagtagtgtg tgcccgtctg ttgtgtgact 360
ctggtaacta gagatccctc agaccctttt agtcagtgtg gaaaatctct agcagtggcg 420
cccgaacagg gacctgaaag cgaaagggaa accagagctc tctcgacgca ggactcggct 480
tgctgaagcg cgcacggcaa gaggcgaggg gcggcgactg gtgagtacgc caaaaatttt 540

-continued

```
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccgctga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcc tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagattgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aactttttaaa agaaaagggg ggattggggg gtacagtgca ggggaaagaa tagtagacat   1860
aatagcaaca gacatacaaa ctaaagaatt acaaaaacaa attacaaaat tcaaaatttt   1920
atcgatgaat tcgctattaa tcccagagcc cttggaagcc agaggaagat gtatctctga   1980
gtttgaggct accctactct acagaaagag ttccaggaca gacattacac gagaagccct   2040
gccccctctc taaaataaaa gtattttcag aagcataaag gtcacagtgt agagaaaatg   2100
actgctacac gtagtcttaa ttatagaggg ctcttttttt tttttttttg atctgtggtg   2160
tacatgtctt tacatttttt tcaagataga aaagcatgat gtctgtgcgg tataaattgt   2220
tcgttttgag ccttgtgtat aacgctttcc tctcaagatt ttataatagt gctttaactg   2280
tccccacggg ctaacttcag cacactgtca tgggacctaa ccttattaaa ttaccatgtg   2340
tgaaccgctc ataactcaag tcgcagcagg tgcaaaaatg gagctgcgca ggcagaagag   2400
tgatcgtcat ttttaaaatc ccccaccagct ggcgaagcaa caggtgccta attcctcatc   2460
ttttaaaaat aacttttcaa aagcctgtgc tgtataagca aatattttca agtttgtttt   2520
taaaccatct tcaagttacc ttcctcacaa aatacattat gtgctgattt ttttgtctca   2580
aaatgacatt tgaagtctaa gcatataaaa atttatttct ttttagaaat gaaattatta   2640
tttaactgga gacttaaatt gtgtcttaac tcttgctcct ccccttttcc ccttttgtcc   2700
cttctctccc cactcccctc cccttctctt cacatgctca tggcgggctc ttctctttcc   2760
tactcttctt ctttctctca tccctctccc ttgtcttgtc ctttcactaa acctttccac   2820
atggaaaaaa taaattgtat cttaaagcta ctagtcataa tgtcaggatg aagggaagcg   2880
atagaaaggg ggaccccaag ccatttttaa acttagatta tactcctgct aatactgctt   2940
```

-continued

```
gcaaaagcct aatctttaat ggcggtttgg gaacctgatc aggttgccac gtgggtgtat   3000
cctaaccagt ccccagagca cgcattgccc tttcaagacc tcagaacttt accataaggg   3060
gcccagcttt ggagactgtt ctttctacac cagttactat ttcaaacctc aacccagttc   3120
catccacgaa gctccattaa tacccaggct tgctgactag acacttgcaa ggtctgtaat   3180
tacgcatcag aagccagtcg tagatgaatc ccacgttttc cacgagcaaa gcaatgtctt   3240
aagcacagtt gcagggaaca tctcagagat gaagaccata aaagtaccga caggcttcag   3300
tctcaccagg gctgttcacg tctggacgct ggattcctaa aaatagccct agggtacatg   3360
tctctctttc tctttgccct aagaaagcta aagaactcct ccaggaggag tggcaactgc   3420
cctgtgaaat ccgatactag atatgaggtc agtttgccca gaaataaaag gaagccaccg   3480
agaggtagga tccgccacca tgcccgccat gaagatcgag tgccgcatca ccggcaccct   3540
gaacggcgtg gagttcgagc tggtgggcgg cggagagggc acccccgagc agggccgcat   3600
gaccaacaag atgaagagca ccaaaggcgc cctgaccttc agcccctacc tgctgagcca   3660
cgtgatgggc tacggcttct accacttcgg cacctacccc agcggctacg agaacccctt   3720
cctgcacgcc atcaacaacg gcggctacac caacacccgc atcgagaagt acgaggacgg   3780
cggcgtgctg cacgtgagct tcagctaccg ctacgaggcc ggccgcgtga tcggcgactt   3840
caaggtggtg ggcaccggct tccccgagga cagcgtgatc ttcaccgaca agatcatccg   3900
cagcaacgcc accgtggagc acctgcaccc catgggcgat aacgtgctgg tgggcagctt   3960
cgcccgcacc ttcagcctgc gcgacggcgg ctactacagc ttcgtggtgg acagccacat   4020
gcacttcaag agcgccatcc accccagcat cctgcagaac gggggcccca tgttcgcctt   4080
ccgccgcgtg gaggagctgc acagcaacac cgagctgggc atcgtggagt accagcacgc   4140
cttcaagacc cccatcgcct tcgccagatc tcgagatatc agccatggct tcccgccggc   4200
ggtggcggcg caggatgatg gcacgctgcc catgtcttgt gcccaggaga gcgggatgga   4260
ccgtcaccct gcagcctgtg cttctgctag gatcaatgtg accggtgagg gcagaggaag   4320
tcttctaaca tgcggtgacg tggaggagaa tcccggccct tccggtatgg aagacgccaa   4380
aaacataaag aaaggcccgg cgccattcta tccgctagag gatggaaccg ctggagagca   4440
actgcataag gctatgaaga gatacgccct ggttcctgga acaattgctt ttacagatgc   4500
acatatcgag gtgaacatca cgtacgcgga atacttcgaa atgtccgttc ggttggcaga   4560
agctatgaaa cgatatgggc tgaatacaaa tcacagaatc gtcgtatgca gtgaaaactc   4620
tcttcaattc tttatgccgg tgttgggcgc gttatttatc ggagttgcag ttgcgcccgc   4680
gaacgacatt tataatgaac gtgaattgct caacagtatg aacatttcgc agcctaccgt   4740
agtgtttgtt tccaaaaagg ggttgcaaaa aattttgaac gtgcaaaaaa aattaccaat   4800
aatccagaaa attattatca tggattctaa aacggattac cagggatttc agtcgatgta   4860
cacgttcgtc acatctcatc tacctcccgg ttttaatgaa tacgattttg taccagagtc   4920
ctttgatcgt gacaaaacaa ttgcactgat aatgaactcc tctggatcta ctgggttacc   4980
taagggtgtg gcccttccgc atagaactgc ctgcgtcaga ttctcgcatg ccagagatcc   5040
tatttttggc aatcaaatca ttccggatac tgcgatttta agtgttgttc cattccatca   5100
cggttttgga atgtttacta cactcggata tttgatatgt ggatttcgag tcgtcttaat   5160
gtatagattt gaagaagagc tgtttttacg atcccttcag gattacaaaa ttcaaagtgc   5220
gttgctagta ccaaccctat tttcattctt cgccaaaagc actctgattg acaaatacga   5280
```

-continued

```
tttatctaat ttacacgaaa ttgcttctgg gggcgcacct ctttcgaaag aagtcgggga   5340
agcggttgca aaacgcttcc atcttccagg gatacgacaa ggatatgggc tcactgagac   5400
tacatcagct attctgatta cacccgaggg ggatgataaa ccgggcgcgg tcggtaaagt   5460
tgttccattt tttgaagcga aggttgtgga tctggatacc gggaaaacgc tgggcgttaa   5520
tcagagaggc gaattatgtg tcagaggacc tatgattatg tccggttatg taaacaatcc   5580
ggaagcgacc aacgccttga ttgacaagga tggatggcta cattctggag acatagctta   5640
ctgggacgaa gacgaacact tcttcatagt tgaccgcttg aagtctttaa ttaaatacaa   5700
aggataccag gtggccccg ctgaattgga gtcgatattg ttacaacacc ccaacatctt   5760
cgacgcgggc gtggcaggtc ttcccgacga tgacgccggt gaacttcccg ccgccgttgt   5820
tgttttggag cacggaaaga cgatgacgga aaaagagatc gtggattacg tcgccagtca   5880
agtaacaacc gcgaaaaagt tgcgcggagg agttgtgttt gtggacgaag taccgaaagg   5940
tcttaccgga aaactcgacg caagaaaaat cagagagatc ctcataaagg ccaagaaggg   6000
cggaaagtcc aaattgtaat cgactcgaca atcaacctct ggattacaaa atttgtgaaa   6060
gattgactgg tattcttaac tatgttgctc cttttacgct atgtggatac gctgctttaa   6120
tgcctttgta tcatgctatt gcttcccgta tggctttcat tttctcctcc ttgtataaat   6180
cctggttgct gtctctttat gaggagttgt ggcccgttgt caggcaacgt ggcgtggtgt   6240
gcactgtgtt tgctgacgca acccccactg gttggggcat tgccaccacc tgtcagctcc   6300
tttccgggac tttcgctttc cccctcccta ttgccacggc ggaactcatc gccgcctgcc   6360
ttgcccgctg ctggacaggg gctcggctgt tgggcactga caattccgtg gtgttgtcgg   6420
ggaagctgac gtcctttcca tggctgctcg cctgtgttgc cacctggatt ctgcgcggga   6480
cgtccttctg ctacgtccct tcggccctca atccagcgga ccttccttcc cgcggcctgc   6540
tgccggctct gcggcctctt ccgcatcttc gccttcgccc tcagacgagt cggatctccc   6600
tttgggccgc ctccccgcct ggaattaatt cgagctcggt accaaggatc tgcgatcgct   6660
ccggtgcccg tcagtgggca gagcgcacat cgcccacagt ccccgagaag ttggggggag   6720
gggtcggcaa ttgaacgggt gcctagagaa ggtggcgcgg ggtaaactgg gaaagtgatg   6780
tcgtgtactg gctccgcctt tttcccgagg gtgggggaga accgtatata agtgcagtag   6840
tcgccgtgaa cgttcttttt cgcaacgggt ttgccgccag aacacagctg aagcttcgag   6900
gggctcgcat ctctccttca cgcgcccgcc gccctacctg aggccgccat ccacgccggt   6960
tgagtcgcgt tctgccgcct cccgcctgtg gtgcctcctg aactgcgtcc gccgtctagg   7020
taagtttaaa gctcaggtcg agaccgggcc tttgtccggc gctcccttgg agcctaccta   7080
gactcagccg gctctccacg ctttgcctga ccctgcttgc tcaactctac gtctttgttt   7140
cgttttctgt tctgcgccgt tacagatcca agctgtgacc ggcgcctacg ctagatgacc   7200
gagtacaagc ccacggtgcg cctcgccacc cgcgacgacg tccccagggc cgtacgcacc   7260
ctcgccgccg cgttcgccga ctaccccgcc acgcgccaca ccgtcgatcc ggaccgccac   7320
atcgagcggg tcaccgagct gcaagaactc ttcctcacgc gcgtcgggct cgacatcggc   7380
aaggtgtggg tcgcggacga cggcgccgcg gtggcggtct ggaccacgcc ggagagcgtc   7440
gaagcggggg cggtgttcgc cgagatcggc ccgcgcatgg ccgagttgag cggttcccgg   7500
ctggccgcgc agcaacagat ggaaggcctc ctggcgccgc accggcccaa ggagcccgcg   7560
tggttcctgg ccaccgtcgg cgtctcgccc gaccaccagg gcaagggtct gggcagcgcc   7620
gtcgtgctcc ccggagtgga ggcggccgag cgcgccgggg tgcccgcctt cctggagacc   7680
```

-continued

```
tccgcgcccc gcaacctccc cttctacgag cggctcggct tcaccgtcac cgccgacgtc   7740
gaggtgcccg aaggaccgcg cacctggtgc atgacccgca agcccggtgc ctgaggtacc   7800
tttaagacca atgacttaca aggcagctgt agatcttagc cactttttaa aagaaaaggg   7860
gggactggaa gggctaattc actcccaacg aaaataagat ctgctttttg cttgtactgg   7920
gtctctctgg ttagaccaga tctgagcctg ggagctctct ggctaactag ggaacccact   7980
gcttaagcct caataaagct tgccttgagt gcttcaagta gtgtgtgccc gtctgttgtg   8040
tgactctggt aactagagat ccctcagacc cttttagtca gtgtggaaaa tctctagcag   8100
tagtagttca tgtcatctta ttattcagta tttataactt gcaaagaaat gaatatcaga   8160
gagtgagagg aacttgttta ttgcagctta taatggttac aaataaagca atagcatcac   8220
aaatttcaca aataaagcat ttttttcact gcattctagt tgtggtttgt ccaaactcat   8280
caatgtatct tatcatgtct ggctctagct atcccgcccc taactccgcc cagttccgcc   8340
cattctccgc cccatggctg actaattttt tttatttatg cagaggccga ggccgcctcg   8400
gcctctgagc tattccagaa gtagtgagga ggcttttttg gaggcctaga cttttgcaga   8460
gacggcccaa attcgtaatc atggtcatag ctgtttcctg tgtgaaattg ttatccgctc   8520
acaattccac acaacatacg agccggaagc ataaagtgta aagcctgggg tgcctaatga   8580
gtgagctaac tcacattaat tgcgttgcgc tcactgcccg ctttccagtc gggaaacctg   8640
tcgtgccagc tgcattaatg aatcggccaa cgcgcgggga gaggcggttt gcgtattggg   8700
cgctcttccg cttcctcgct cactgactcg ctgcgctcgg tcgttcggct gcggcgagcg   8760
gtatcagctc actcaaaggc ggtaatacgg ttatccacag aatcagggga taacgcagga   8820
aagaacatgt gagcaaaagg ccagcaaaag gccaggaacc gtaaaaaggc cgcgttgctg   8880
gcgtttttcc ataggctccg cccccctgac gagcatcaca aaaatcgacg ctcaagtcag   8940
aggtggcgaa acccgacagg actataaaga taccaggcgt ttccccctgg aagctccctc   9000
gtgcgctctc ctgttccgac cctgccgctt accggatacc tgtccgcctt tctcccttcg   9060
ggaagcgtgg cgctttctca tagctcacgc tgtaggtatc tcagttcggt gtaggtcgtt   9120
cgctccaagc tgggctgtgt gcacgaaccc cccgttcagc ccgaccgctg cgccttatcc   9180
ggtaactatc gtcttgagtc caacccggta agacacgact tatcgccact ggcagcagcc   9240
actggtaaca ggattagcag agcgaggtat gtaggcggtg ctacagagtt cttgaagtgg   9300
tggcctaact acggctacac tagaaggaca gtatttggta tctgcgctct gctgaagcca   9360
gttaccttcg gaaaaagagt tggtagctct tgatccggca aacaaaccac cgctggtagc   9420
ggtggttttt ttgtttgcaa gcagcagatt acgcgcagaa aaaaaggatc tcaagaagat   9480
cctttgatct tttctacggg gtctgacgct cagtggaacg aaaactcacg ttaagggatt   9540
ttggtcatga gattatcaaa aaggatcttc acctagatcc ttttaaatta aaaatgaagt   9600
tttaaatcaa tctaaagtat atatgagtaa acttggtctg acagttacca atgcttaatc   9660
agtgaggcac ctatctcagc gatctgtcta tttcgttcat ccatagttgc ctgactcccc   9720
gtcgtgtaga taactacgat acgggagggc ttaccatctg gccccagtgc tgcaatgata   9780
ccgcgagacc cacgctcacc ggctccagat ttatcagcaa taaaccagcc agccggaagg   9840
gccgagcgca gaagtggtcc tgcaacttta tccgcctcca tccagtctat taattgttgc   9900
cgggaagcta gagtaagtag ttcgccagtt aatagtttgc gcaacgttgt tgccattgct   9960
acaggcatcg tggtgtcacg ctcgtcgttt ggtatggctt cattcagctc cggttcccaa  10020
```

-continued cgatcaaggc gagttacatg atcccccatg ttgtgcaaaa aagcggttag ctccttcggt 10080
cctccgatcg ttgtcagaag taagttggcc gcagtgttat cactcatggt tatggcagca 10140
ctgcataatt ctcttactgt catgccatcc gtaagatgct tttctgtgac tggtgagtac 10200
tcaaccaagt cattctgaga atagtgtatg cggcgaccga gttgctcttg cccggcgtca 10260
atacgggata ataccgcgcc acatagcaga actttaaaag tgctcatcat tggaaaacgt 10320
tcttcggggc gaaaactctc aaggatctta ccgctgttga gatccagttc gatgtaaccc 10380
actcgtgcac ccaactgatc ttcagcatct tttactttca ccagcgtttc tgggtgagca 10440
aaaacaggaa ggcaaaatgc cgcaaaaaag ggaataaggg cgacacggaa atgttgaata 10500
ctcatactct tcctttttca atattattga agcatttatc agggttattg tctcatgagc 10560
ggatacatat ttgaatgtat ttagaaaaat aaacaaatag gggttccgcg cacatttccc 10620
cgaaaagtgc cacctgacgt ctaagaaacc attattatca tgacattaac ctataaaaat 10680
aggcgtatca cgaggccctt tcgtctcgcg cgtttcggtg atgacggtga aaacctctga 10740
cacatgcagc tcccggagac ggtcacagct tgtctgtaag cggatgccgg gagcagacaa 10800
gcccgtcagg gcgcgtcagc gggtgttggc gggtgtcggg gctggcttaa ctatgcggca 10860
tcagagcaga ttgtactgag agtgcaccat atgcggtgtg aaataccgca cagatgcgta 10920
aggagaaaat accgcatcag gcgccattcg ccattcaggc tgcgcaactg ttgggaaggg 10980
cgatcggtgc gggcctcttc gctattacgc cagctggcga aagggggatg tgctgcaagg 11040
cgattaagtt gggtaacgcc agggttttcc cagtcacgac gttgtaaaac gacggccagt 11100
gccaagctg 11109

<210> SEQ ID NO 5
<211> LENGTH: 900
<212> TYPE: DNA
<213> ORGANISM: Artificial sequence
<220> FEATURE:
<223> OTHER INFORMATION: chicken MyoD1 gene

<400> SEQUENCE: 5
atggaccttt tgggaccgat ggaaatgact gagggttctc tctgttcttt taccgctgcg 60
gatgatttct atgatgaccc ctgtttcaac acgagcgata tgcacttttt cgaagatctg 120
gaccccaggc tcgtccacgt tggcggtctt ctgaaagccg aagaacatcc tcatcatcat 180
gggcaccatc atggtaatcc tcatgaggag gagcatgtaa gggcccccag cggtcatcat 240
caggccggta ggtgcctgct ttgggcgtgc aaggcttgca aaaggaaaac aactaatgct 300
gaccggcgga aagcagccac gatgcgcgaa cgccgcaggt tgtctaaagt caacgaagca 360
ttcgagacgc ttaagcggtg tacaagtact aatccaaacc agaggctccc caaagttgaa 420
atccttcgga atgcaattcg gtatatcgaa agcctgcaag cgctgctccg ggaacaagaa 480
gacgcatatt accccgtcct cgaacactac tctggagaaa gtgacgcctc cagcccacgc 540
agtaactgct ccgacgggat gatggaatat tctggaccac cgtgctctag ccggcgcaga 600
aattcatacg actcctctta ctacacagag agcccgaatg atccgaagca cgggaagtct 660
agcgtggtct cttcactgga ttgtctcagt agcattgtcg agcgcatcag tactgacaac 720
tccacctgcc cgatattgcc gcccgccgaa gctgttgctg agggcagtcc atgtagcccc 780
caggaggggg gaaatctttc tgactccggg gctcaaattc catccccgac caactgtacc 840
ccactgccgc aggaatctag ctccagtagt tcaagcaacc cgatatatca agttctttag 900

<210> SEQ ID NO 6
<211> LENGTH: 173
<212> TYPE: DNA
<213> ORGANISM: Artificial sequence
<220> FEATURE:
<223> OTHER INFORMATION: VP64 transcriptional activator

<400> SEQUENCE: 6
tgaaaacgtc tgggcaagcg ggtcaggcat ccccgaagaa gaaaaggaag gtcgggagag 60
cggacgcgct cgatgacttc gatttggaca tgctcggctc cgatgctctg gatgactttg 120
atctggacat gctcggttca gatgcgctgg atgattttga tttggatatg ctc 173

<210> SEQ ID NO 7
<211> LENGTH: 684
<212> TYPE: DNA
<213> ORGANISM: Artificial sequence
<220> FEATURE:
<223> OTHER INFORMATION: cMyogenin coding sequence

<400> SEQUENCE: 7
atggagctct ttgagaccaa cccttacttt ttcccggagc agaggtttta cgatggggaa 60
aacttcctgg gctcccgctt gcagggctac gaggcggccg cgtttcctga gcgtcccgag 120
gtgaccctgt gccctgaaag cagaggggct ttggaggaga aggactcgac gctgcccgag 180
cactgccccg ggcaatgctt gccatgggct tgcaaaatct gcaagcgcaa aaccgtgtcc 240
atcgaccggc gtcgggcggc cacgctgcgg gagaagcgga ggctgaagaa ggtgaacgaa 300
gccttcgagg ctctgaaacg cagcactctg ctcaacccca accagcggct gcccaaggtg 360
gagatcctgc gcagcgccat ccagtacatc gagcgcctgc agagcctgct cagcagcctc 420
aaccagcagg agcgtgagca gagggagctg cgctaccgcc ccgctgcacc acaacctgct 480
gcacccagcg agtgcggctc tggcagctca tcctgcagcc ctgagtggag cacccagctg 540
gagtttggca ccaaccccgc agatcacctc ctgagcgatg accaggcaga ggaccgcaac 600
ctccactcgc tctcctccat cgtggagagc atcgccgtgg aggacgtggc cgtgacgttc 660
ccagaggagc gggtccaaaa ctga 684

<210> SEQ ID NO 8
<211> LENGTH: 39
<212> TYPE: DNA
<213> ORGANISM: Artificial sequence
<220> FEATURE:
<223> OTHER INFORMATION: minimal CMV promoter sequence

<400> SEQUENCE: 8
ggtaggcgtg tacggtggga ggcctatata agcagagct 39

<210> SEQ ID NO 9
<211> LENGTH: 2341
<212> TYPE: DNA
<213> ORGANISM: Artificial sequence
<220> FEATURE:
<223> OTHER INFORMATION: rat myosin light chain-3 promoter-enhancer
(rMLC3-GFP)

<400> SEQUENCE: 9
gctattaatc ccagagccct tggaagccag aggaagatgt atctctgagt ttgaggctac 60
cctactctac agaaagagtt ccaggacaga cattacacga gaagccctgc cccctctcta 120
aaataaaagt attttcagaa gcataaaggt cacagtgtag agaaaatgac tgctacacgt 180
agtcttaatt atagagggct cttttttttt ttttttgat ctgtggtgta catgtcttta 240

```
catttttttc aagatagaaa agcatgatgt ctgtgcggta taaattgttc gttttgagcc    300
ttgtgtataa cgctttcctc tcaagatttt ataatagtgc tttaactgtc cccacgggct    360
aacttcagca cactgtcatg ggacctaacc ttattaaatt accatgtgtg aaccgctcat    420
aactcaagtc gcagcaggtg caaaaatgga gctgcgcagg cagaagagtg atcgtcattt    480
ttaaaatccc caccagctgg cgaagcaaca ggtgcctaat tcctcatctt ttaaaaataa    540
cttttcaaaa gcctgtgctg tataagcaaa tattttcaag tttgttttta aaccatcttc    600
aagttacctt cctcacaaaa tacattatgt gctgattttt ttgtctcaaa atgacatttg    660
aagtctaagc atataaaaat ttatttcttt ttagaaatga aattattatt taactggaga    720
cttaaattgt gtcttaactc ttgctcctcc ccttttcccc ttttgtccct tctctcccca    780
ctcccctccc cttctcttca catgctcatg gcgggctctt ctctttccta ctcttcttct    840
ttctctcatc cctctccctt gtcttgtcct ttcactaaac ctttccacat ggaaaaaata    900
aattgtatct taaagctcat aatgtcagga tgaagggaag cgatagaaag gggacccca     960
agccattttt aaacttagat tatactcctg ctaatactgc ttgcaaaagc ctaatcttta   1020
atggcggttt gggaacctga tcaggttgcc acgtgggtgt atcctaacca gtccccagag   1080
cacgcattgc cctttcaaga cctcagaact ttaccataag gggcccagct ttggagactg   1140
ttctttctac accagttact atttcaaacc tcaacccagt tccatccacg aagctccatt   1200
aatacccagg cttgctgact agacacttgc aaggtctgta attacgcatc agaagccagt   1260
cgtagatgaa tcccacgttt tccacgagca aagcaatgtc ttaagcacag ttgcagggaa   1320
catctcagag atgaagacca taaaagtacc gacaggcttc agtctcacca gggctgttca   1380
cgtctggacg ctggattcct aaaaatagcc ctagggtaca tgtctctctt tctctttgcc   1440
ctaagaaagc taaagaactc ctccaggagg agtggcaact gccctgtgaa atccgatact   1500
agatatgagg tcagtttgcc cagaaataaa aggaagccac cgagaggtaa tgaagatcga   1560
gtgccgcatc accggcaccc tgaacggcgt ggagttcgag ctggtgggcg gcggagaggg   1620
cacccccgag cagggccgca tgaccaacaa gatgaagagc accaaaggcg ccctgacctt   1680
cagcccctac ctgctgagcc acgtgatggg ctacggcttc taccacttcg gcacctaccc   1740
cagcggctac gagaacccct tcctgcacgc catcaacaac ggcggctaca ccaacacccg   1800
catcgagaag tacgaggacg gcggcgtgct gcacgtgagc ttcagctacc gctacgaggc   1860
cggccgcgtg atcggcgact tcaaggtggt gggcaccggc ttccccgagg acagcgtgat   1920
cttcaccgac aagatcatcc gcagcaacgc caccgtggag cacctgcacc ccatgggcga   1980
taacgtgctg gtgggcagct tcgcccgcac cttcagcctg cgcgacggcg gctactacag   2040
cttcgtggtg gacagccaca tgcacttcaa gagcgccatc caccccagca tcctgcagaa   2100
cgggggcccc atgttcgcct tccgccgcgt ggaggagctg cacagcaaca ccgagctggg   2160
catcgtggag taccagcacg ccttcaagac ccccatcgcc ttcgccagat ctcgagatat   2220
cagccatggc ttcccgccgg cggtggcggc gcaggatgat ggcacgctgc ccatgtcttg   2280
tgcccaggag agcgggatgg accgtcaccc tgcagcctgt gcttctgcta ggatcaatgt   2340
g                                                                   2341
```

<210> SEQ ID NO 10
<211> LENGTH: 917
<212> TYPE: DNA
<213> ORGANISM: Artificial sequence
<220> FEATURE:

-continued

<223> OTHER INFORMATION: rat MLC3 enhancer

<400> SEQUENCE: 10
gctattaatc ccagagccct tggaagccag aggaagatgt atctctgagt ttgaggctac 60
cctactctac agaaagagtt ccaggacaga cattacacga gaagccctgc cccctctcta 120
aaataaaagt attttcagaa gcataaaggt cacagtgtag agaaaatgac tgctacacgt 180
agtcttaatt atagagggct cttttttttt tttttttgat ctgtggtgta catgtcttta 240
catttttttc aagatagaaa agcatgatgt ctgtgcggta taaattgttc gttttgagcc 300
ttgtgtataa cgctttcctc tcaagatttt ataatagtgc tttaactgtc cccacgggct 360
aacttcagca cactgtcatg ggacctaacc ttattaaatt accatgtgtg aaccgctcat 420
aactcaagtc gcagcaggtg caaaaatgga gctgcgcagg cagaagagtg atcgtcattt 480
ttaaaatccc caccagctgg cgaagcaaca ggtgcctaat tcctcatctt ttaaaaataa 540
cttttcaaaa gcctgtgctg tataagcaaa tattttcaag tttgttttta aaccatcttc 600
aagttacctt cctcacaaaa tacattatgt gctgattttt ttgtctcaaa atgacatttg 660
aagtctaagc atataaaaat ttatttcttt ttagaaatga aattattatt taactggaga 720
cttaaattgt gtcttaactc ttgctcctcc ccttttcccc ttttgtccct tctctcccca 780
ctcccctccc cttctcttca catgctcatg gcgggctctt ctctttccta ctcttcttct 840
ttctctcatc cctctccctt gtcttgtcct ttcactaaac ctttccacat ggaaaaaata 900
aattgtatct taaagct 917

<210> SEQ ID NO 11
<211> LENGTH: 632
<212> TYPE: DNA
<213> ORGANISM: Artificial sequence
<220> FEATURE:
<223> OTHER INFORMATION: rat MLC3 promoter sequence

<400> SEQUENCE: 11
cataatgtca ggatgaaggg aagcgataga aaggggggacc ccaagccatt tttaaactta 60
gattatactc ctgctaatac tgcttgcaaa agcctaatct ttaatggcgg tttgggaacc 120
tgatcaggtt gccacgtggg tgtatcctaa ccagtcccca gagcacgcat tgccctttca 180
agacctcaga actttaccat aaggggccca gctttggaga ctgttctttc tacaccagtt 240
actatttcaa acctcaaccc agttccatcc acgaagctcc attaataccc aggcttgctg 300
actagacact tgcaaggtct gtaattacgc atcagaagcc agtcgtagat gaatcccacg 360
ttttccacga gcaaagcaat gtcttaagca cagttgcagg gaacatctca gagatgaaga 420
ccataaaagt accgacaggc ttcagtctca ccagggctgt tcacgtctgg acgctggatt 480
cctaaaaata gccctagggt acatgtctct ctttctcttt gccctaagaa agctaaagaa 540
ctcctccagg aggagtggca actgccctgt gaaatccgat actagatatg aggtcagttt 600
gcccagaaat aaaaggaagc caccgagagg ta 632

<210> SEQ ID NO 12
<211> LENGTH: 792
<212> TYPE: DNA
<213> ORGANISM: Artificial sequence
<220> FEATURE:
<223> OTHER INFORMATION: COP-GFP sequence

<400> SEQUENCE: 12

```
atgaagatcg agtgccgcat caccggcacc ctgaacggcg tggagttcga gctggtgggc     60
ggcggagagg gcacccccga gcagggccgc atgaccaaca agatgaagag caccaaaggc    120
gccctgacct tcagccccta cctgctgagc cacgtgatgg gctacggctt ctaccacttc    180
ggcacctacc ccagcggcta cgagaacccc ttcctgcacg ccatcaacaa cggcggctac    240
accaacaccc gcatcgagaa gtacgaggac ggcggcgtgc tgcacgtgag cttcagctac    300
cgctacgagg ccggccgcgt gatcggcgac ttcaaggtgg tgggcaccgg cttccccgag    360
gacagcgtga tcttcaccga caagatcatc cgcagcaacg ccaccgtgga gcacctgcac    420
cccatgggcg ataacgtgct ggtgggcagc ttcgcccgca ccttcagcct gcgcgacggc    480
ggctactaca gcttcgtggt ggacagccac atgcacttca agagcgccat ccaccccagc    540
atcctgcaga acgggggccc catgttcgcc ttccgccgcg tggaggagct gcacagcaac    600
accgagctgg gcatcgtgga gtaccagcac gccttcaaga cccccatcgc cttcgccaga    660
tctcgagata tcagccatgg cttcccgccg gcggtggcgg cgcaggatga tggcacgctg    720
cccatgtctt gtgcccagga gagcgggatg gaccgtcacc ctgcagcctg tgcttctgct    780
aggatcaatg tg                                                        792
```

<210> SEQ ID NO 13
<211> LENGTH: 469
<212> TYPE: DNA
<213> ORGANISM: homo sapiens

<400> SEQUENCE: 13

```
agccctccag gacaggctgc atcagaagag gccatcaagc agatcactgt ccttctgcca     60
tggccctgtg gatgcgcctc ctgcccctgc tggcgctgct ggccctctgg ggacctgacc    120
cagccgcagc ctttgtgaac caacacctgt gcggctcaca cctggtggaa gctctctacc    180
tagtgtgcgg ggaacgaggc ttcttctaca cacccaagac ccgccgggag gcagaggacc    240
tgcaggtggg gcaggtggag ctgggcgggg gccctggtgc aggcagcctg cagcccttgg    300
ccctggaggg gtccctgcag aagcgtggca ttgtggaaca atgctgtacc agcatctgct    360
ccctctacca gctggagaac tactgcaact agacgcagcc cgcaggcagc cccacacccg    420
ccgcctcctg caccgagaga gatggaataa agcccttgaa ccagcaaaa                469
```

<210> SEQ ID NO 14
<211> LENGTH: 110
<212> TYPE: PRT
<213> ORGANISM: homo sapiens

<400> SEQUENCE: 14

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80
```

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 15
<211> LENGTH: 495
<212> TYPE: DNA
<213> ORGANISM: homo sapiens

<400> SEQUENCE: 15
agccctccag gacaggctgc atcagaagag gccatcaagc aggtctgttc caagggcctt 60
tgcgtcagat cactgtcctt ctgccatggc cctgtggatg cgcctcctgc ccctgctggc 120
gctgctggcc ctctggggac ctgacccagc cgcagccttt gtgaaccaac acctgtgcgg 180
ctcacacctg gtggaagctc tctacctagt gtgcggggaa cgaggcttct tctacacacc 240
caagacccgc cgggaggcag aggacctgca ggtggggcag gtggagctgg gcgggggccc 300
tggtgcaggc agcctgcagc ccttggccct ggaggggtcc ctgcagaagc gtggcattgt 360
ggaacaatgc tgtaccagca tctgctccct ctaccagctg gagaactact gcaactagac 420
gcagcccgca ggcagcccca cacccgccgc ctcctgcacc gagagagatg gaataaagcc 480
cttgaaccag caaaa 495

<210> SEQ ID NO 16
<211> LENGTH: 110
<212> TYPE: PRT
<213> ORGANISM: homo sapiens

<400> SEQUENCE: 16

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110

<210> SEQ ID NO 17
<211> LENGTH: 648
<212> TYPE: DNA
<213> ORGANISM: homo sapiens

<400> SEQUENCE: 17
agccctccag gacaggctgc atcagaagag gccatcaagc aggtctgttc caagggcctt 60
tgcgtcaggt gggctcagga ttccagggtg gctggacccc aggccccagc tctgcagcag 120
ggaggacgtg gctgggctcg tgaagcatgt gggggtgagc ccaggggccc caaggcaggg 180
cacctggcct tcagcctgcc tcagccctgc ctgtctccca gatcactgtc cttctgccat 240
ggccctgtgg atgcgcctcc tgcccctgct ggcgctgctg gccctctggg gacctgaccc 300

```
agccgcagcc tttgtgaacc aacacctgtg cggctcacac ctggtggaag ctctctacct    360

agtgtgcggg gaacgaggct tcttctacac acccaagacc cgccgggagg cagaggacct    420

gcaggtgggg caggtggagc tgggcggggg ccctggtgca ggcagcctgc agcccttggc    480

cctggagggg tccctgcaga agcgtggcat tgtggaacaa tgctgtacca gcatctgctc    540

cctctaccag ctggagaact actgcaacta gacgcagccc gcaggcagcc ccacacccgc    600

cgcctcctgc accgagagag atggaataaa gcccttgaac cagcaaaa                 648
```

```
<210> SEQ ID NO 18
<211> LENGTH: 110
<212> TYPE: PRT
<213> ORGANISM: homo sapiens

<400> SEQUENCE: 18

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

```
<210> SEQ ID NO 19
<211> LENGTH: 529
<212> TYPE: DNA
<213> ORGANISM: homo sapiens

<400> SEQUENCE: 19

agccctccag gacaggctgc atcagaagag gccatcaagc aggtctgttc caagggcctt     60

tgcgtcaggt gggctcagga ttccagggtg gctggacccc agatcactgt ccttctgcca    120

tggccctgtg gatgcgcctc ctgcccctgc tggcgctgct ggccctctgg ggacctgacc    180

cagccgcagc ctttgtgaac caacacctgt gcggctcaca cctggtggaa gctctctacc    240

tagtgtgcgg ggaacgaggc ttcttctaca cacccaagac ccgccgggag gcagaggacc    300

tgcaggtggg gcaggtggag ctgggcgggg gccctggtgc aggcagcctg cagcccttgg    360

ccctggaggg gtccctgcag aagcgtggca ttgtggaaca atgctgtacc agcatctgct    420

ccctctacca gctggagaac tactgcaact agacgcagcc cgcaggcagc cccacacccg    480

ccgcctcctg caccgagaga gatggaataa agcccttgaa ccagcaaaa                529
```

```
<210> SEQ ID NO 20
<211> LENGTH: 110
<212> TYPE: PRT
<213> ORGANISM: homo sapiens

<400> SEQUENCE: 20

Met Ala Leu Trp Met Arg Leu Leu Pro Leu Leu Ala Leu Leu Ala Leu
1               5                   10                  15
```

-continued

```
Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110


<210> SEQ ID NO 21
<211> LENGTH: 288
<212> TYPE: PRT
<213> ORGANISM: homo sapiens

<400> SEQUENCE: 21

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
        195                 200                 205

Gly Val Cys Ala Asn Arg Tyr Leu Ala Met Lys Glu Asp Gly Arg Leu
    210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285
```

<210> SEQ ID NO 22
<211> LENGTH: 6774
<212> TYPE: DNA
<213> ORGANISM: homo sapiens

<400> SEQUENCE: 22
cggccccaga aaacccgagc gagtaggggg cggcgcgcag gagggaggag aactgggggc 60
gcgggaggct ggtgggtgtg gggggtggag atgtagaaga tgtgacgccg cggcccggcg 120
ggtgccagat tagcggacgc ggtgcccgcg gttgcaacgg gatcccgggc gctgcagctt 180
gggaggcggc tctccccagg cggcgtccgc ggagacaccc atccgtgaac cccaggtccc 240
gggccgccgg ctcgccgcgc accaggggcc ggcggacaga agagcggccg agcggctcga 300
ggctggggga ccgcgggcgc ggccgcgcgc tgccgggcgg gaggctgggg ggccggggcc 360
ggggccgtgc cccggagcgg gtcggaggcc ggggccgggg ccgggggacg gcggctcccc 420
gcgcggctcc agcggctcgg ggatcccggc cgggccccgc agggaccatg gcagccggga 480
gcatcaccac gctgcccgcc ttgcccgagg atggcggcag cggcgccttc ccgcccggcc 540
acttcaagga ccccaagcgg ctgtactgca aaaacggggg cttcttcctg cgcatccacc 600
ccgacggccg agttgacggg gtccgggaga agagcgaccc tcacatcaag ctacaacttc 660
aagcagaaga gagaggagtt gtgtctatca aaggagtgtg tgctaaccgt tacctggcta 720
tgaaggaaga tggaagatta ctggcttcta aatgtgttac ggatgagtgt ttcttttttg 780
aacgattgga atctaataac tacaatactt accggtcaag gaaatacacc agttggtatg 840
tggcactgaa acgaactggg cagtataaac ttggatccaa aacaggacct gggcagaaag 900
ctatactttt tcttccaatg tctgctaaga gctgatttta atggccacat ctaatctcat 960
ttcacatgaa agaagaagta tattttagaa atttgttaat gagagtaaaa gaaaataaat 1020
gtgtatagct cagtttggat aattggtcaa acaatttttt atccagtagt aaaatatgta 1080
accattgtcc cagtaaagaa aaataacaaa agttgtaaaa tgtatattct cccttttata 1140
ttgcatctgc tgttacccag tgaagcttac ctagagcaat gatctttttc acgcatttgc 1200
tttattcgaa aagaggcttt taaaatgtgc atgtttagaa acaaaatttc ttcatggaaa 1260
tcatatacat tagaaaatca cagtcagatg tttaatcaat ccaaaatgtc cactatttct 1320
tatgtcattc gttagtctac atgtttctaa acatataaat gtgaatttaa tcaattcctt 1380
tcatagtttt ataattctct ggcagttcct tatgatagag tttataaaac agtcctgtgt 1440
aaactgctgg aagttcttcc acagtcaggt caattttgtc aaacccttct ctgtacccat 1500
acagcagcag cctagcaact ctgctggtga tgggagttgt attttcagtc ttcgccaggt 1560
cattgagatc catccactca catcttaagc attcttcctg gcaaaaattt atggtgaatg 1620
aatatggctt taggcggcag atgatataca tatctgactt cccaaaagct ccaggatttg 1680
tgtgctgttg ccgaatactc aggacggacc tgaattctga ttttatacca gtctcttcaa 1740
aaacttctcg aaccgctgtg tctcctacgt aaaaaaagag atgtacaaat caataataat 1800
tacactttta gaaactgtat catcaaagat tttcagttaa agtagcatta tgtaaaggct 1860
caaaacatta ccctaacaaa gtaaagtttt caatacaaat tctttgcctt gtggatatca 1920
agaaatccca aaatattttc ttaccactgt aaattcaaga agcttttgaa atgctgaata 1980
tttctttggc tgctacttgg aggcttatct acctgtacat tttggggtc agctcttttt 2040
aacttcttgc tgctcttttt cccaaaaggt aaaaatatag attgaaaagt taaaacattt 2100

-continued

```
tgcatggctg cagttccttt gtttcttgag ataagattcc aaagaactta gattcatttc   2160
ttcaacaccg aaatgctgga ggtgtttgat cagttttcaa gaaacttgga atataaataa   2220
ttttataatt caacaaaggt tttcacattt tataaggttg atttttcaat taaatgcaaa   2280
tttgtgtggc aggattttta ttgccattaa catatttttg tggctgcttt ttctacacat   2340
ccagatggtc cctctaactg ggctttctct aattttgtga tgttctgtca ttgtctccca   2400
aagtatttag gagaagccct ttaaaaagct gccttcctct accactttgc tggaaagctt   2460
cacaattgtc acagacaaag atttttgttc caatactcgt tttgcctcta tttttcttgt   2520
ttgtcaaata gtaaatgata tttgcccttg cagtaattct actggtgaaa aacatgcaaa   2580
gaagaggaag tcacagaaac atgtctcaat tcccatgtgc tgtgactgta gactgtctta   2640
ccatagactg tcttacccat cccctggata tgctcttgtt ttttccctct aatagctatg   2700
gaaagatgca tagaaagagt ataatgtttt aaaacataag gcattcgtct gccatttttc   2760
aattacatgc tgacttccct tacaattgag atttgcccat aggttaaaca tggttagaaa   2820
caactgaaag cataaaagaa aaatctaggc cgggtgcagt ggctcatgcc tatattccct   2880
gcactttggg aggccaaagc aggaggatcg cttgagccca ggagttcaag accaacctgg   2940
tgaaaccccg tctctacaaa aaaacacaaa aaatagccag gcatggtggc gtgtacatgt   3000
ggtctcagat acttgggagg ctgaggtggg agggttgatc acttgaggct gagaggtcaa   3060
ggttgcagtg agccataatc gtgccactgc agtccagcct aggcaacaga gtgagacttt   3120
gtctcaaaaa aagagaaatt ttccttaata agaaaagtaa tttttactct gatgtgcaat   3180
acatttgtta ttaaatttat tatttaagat ggtagcacta gtcttaaatt gtataaaata   3240
tcccctaaca tgtttaaatg tccattttta ttcattatgc tttgaaaaat aattatgggg   3300
aaatacatgt ttgttattaa atttattatt aaagatagta gcactagtct taaatttgat   3360
ataacatctc ctaacttgtt taaatgtcca tttttattct ttatgtttga aaataaatta   3420
tggggatcct atttagctct tagtaccact aatcaaaagt tcggcatgta gctcatgatc   3480
tatgctgttt ctatgtcgtg gaagcaccgg atgggggtag tgagcaaatc tgccctgctc   3540
agcagtcacc atagcagctg actgaaaatc agcactgcct gagtagtttt gatcagttta   3600
acttgaatca ctaactgact gaaaattgaa tgggcaaata agtgcttttg tctccagagt   3660
atgcgggaga cccttccacc tcaagatgga tatttcttcc ccaaggattt caagatgaat   3720
tgaaattttt aatcaagata gtgtgcttta ttctgttgta tttttttatta ttttaatata   3780
ctgtaagcca aactgaaata acatttgctg ttttataggt ttgaagaaca taggaaaaac   3840
taagaggttt tgtttttatt tttgctgatg aagagatatg tttaaatatg ttgtattgtt   3900
ttgtttagtt acaggacaat aatgaaatgg agtttatatt tgttatttct attttgttat   3960
atttaataat agaattagat tgaaataaaa tataatggga aataatctgc agaatgtggg   4020
ttttcctggt gtttccctct gactctagtg cactgatgat ctctgataag gctcagctgc   4080
tttatagttc tctggctaat gcagcagata ctcttcctgc cagtggtaat acgatttttt   4140
aagaaggcag tttgtcaatt ttaatcttgt ggataccttt atactcttag ggtattattt   4200
tatacaaaag ccttgaggat tgcattctat tttctatatg accctcttga tatttaaaaa   4260
acactatgga taacaattct tcatttacct agtattatga aagaatgaag gagttcaaac   4320
aaatgtgttt cccagttaac tagggtttac tgtttgagcc aatataaatg tttaactgtt   4380
tgtgatggca gtattcctaa agtacattgc atgttttcct aaatacagag tttaaataat   4440
ttcagtaatt cttagatgat tcagcttcat cattaagaat atcttttgtt ttatgttgag   4500
```

-continued

```
ttagaaatgc cttcatatag acatagtctt tcagacctct actgtcagtt ttcatttcta   4560
gctgctttca gggttttatg aattttcagg caaagcttta atttatacta agcttaggaa   4620
gtatggctaa tgccaacggc agtttttttc ttcttaattc cacatgactg aggcatatat   4680
gatctctggg taggtgagtt gttgtgacaa ccacaagcac tttttttttt tttaaagaaa   4740
aaaaggtagt gaatttttaa tcatctggac tttaagaagg attctggagt atacttaggc   4800
ctgaaattat atatatttgg cttggaaatg tgtttttctt caattacatc tacaagtaag   4860
tacagctgaa attcagagga cccataagag ttcacatgaa aaaaatcaat ttatttgaaa   4920
aggcaagatg caggagagag gaagccttgc aaacctgcag actgcttttt gcccaatata   4980
gattgggtaa ggctgcaaaa cataagctta attagctcac atgctctgct ctcacgtggc   5040
accagtggat agtgtgagag aattaggctg tagaacaaat ggccttctct ttcagcattc   5100
acaccactac aaaatcatct tttatatcaa cagaagaata agcataaact aagcaaaagg   5160
tcaataagta cctgaaacca agattggcta gagatatatc ttaatgcaat ccattttctg   5220
atggattgtt acgagttggc tatataatgt atgtatggta ttttgatttg tgtaaaagtt   5280
ttaaaaatca agctttaagt acatggacat ttttaaataa aatatttaaa gacaatttag   5340
aaaattgcct taatatcatt gttggctaaa tagaataggg gacatgcata ttaaggaaaa   5400
ggtcatggag aaataatatt ggtatcaaac aaatacattg atttgtcatg atacacattg   5460
aatttgatcc aatagtttaa ggaataggta ggaaaatttg gtttctattt ttcgatttcc   5520
tgtaaatcag tgacataaat aattcttagc ttattttata tttccttgtc ttaaatactg   5580
agctcagtaa gttgtgttag gggattattt ctcagttgag actttcttat atgacatttt   5640
actatgtttt gacttcctga ctattaaaaa taaatagtag atacaatttt cataaagtga   5700
agaattatat aatcactgct ttataactga ctttattata tttatttcaa agttcattta   5760
aaggctacta ttcatcctct gtgatggaat ggtcaggaat ttgttttctc atagtttaat   5820
tccaacaaca atattagtcg tatccaaaat aacctttaat gctaaacttt actgatgtat   5880
atccaaagct tctcattttc agacagatta atccagaagc agtcataaac agaagaatag   5940
gtggtatgtt cctaatgata ttatttctac taatggaata aactgtaata ttagaaatta   6000
tgctgctaat tatatcagct ctgaggtaat ttctgaaatg ttcagactca gtcggaacaa   6060
attggaaaat ttaaattttt attcttagct ataaagcaag aaagtaaaca cattaatttc   6120
ctcaacattt ttaagccaat taaaaatata aaagatacac accaatatct tcttcaggct   6180
ctgacaggcc tcctggaaac ttccacatat ttttcaactg cagtataaag tcagaaaata   6240
aagttaacat aactttcact aacacacaca tatgtagatt tcacaaaatc cacctataat   6300
tggtcaaagt ggttgagaat atattttta gtaattgcat gcaaaatttt tctagcttcc   6360
atcctttctc cctcgtttct tcttttttg ggggagctgg taactgatga aatcttttcc   6420
cacctttct cttcaggaaa tataagtggt tttgtttggt taacgtgata cattctgtat   6480
gaatgaaaca ttggagggaa acatctactg aatttctgta atttaaaata ttttgctgct   6540
agttaactat gaacagatag aagaatctta cagatgctgc tataaataag tagaaaatat   6600
aaatttcatc actaaaatat gctattttaa aatctatttc ctatattgta tttctaatca   6660
gatgtattac tcttattatt tctattgtat gtgttaatga ttttatgtaa aaatgtaatt   6720
gcttttcatg agtagtatga ataaaattga ttagtttgtg ttttcttgtc tccc         6774
```